United States Patent
Niijima et al.

(10) Patent No.: US 11,691,990 B2
(45) Date of Patent: Jul. 4, 2023

(54) SALTS OF COMPOUNDS AND CRYSTALS THEREOF

(71) Applicant: Eisai R&D Management Co., Ltd., Tokyo (JP)

(72) Inventors: Jun Niijima, Kamisu (JP); Hirofumi Kuroda, Kamisu (JP); So Yasui, Tsukuba (JP); Yoko Ito, Tsukuba (JP); Ikuo Kushida, Tsukuba (JP)

(73) Assignee: Eisai R&D Management Co., LTD, Tokyo (JP)

( * ) Notice: Subject to any disclaimer, the term of this patent is extended or adjusted under 35 U.S.C. 154(b) by 0 days.

(21) Appl. No.: 17/058,406

(22) PCT Filed: Aug. 14, 2019

(86) PCT No.: PCT/JP2019/031951
§ 371 (c)(1),
(2) Date: Nov. 24, 2020

(87) PCT Pub. No.: WO2020/036199
PCT Pub. Date: Feb. 20, 2020

(65) Prior Publication Data
US 2021/0198282 A1   Jul. 1, 2021

Related U.S. Application Data

(60) Provisional application No. 62/764,774, filed on Aug. 16, 2018.

(51) Int. Cl.
| C07D 519/00 | (2006.01) |
| A61P 35/00 | (2006.01) |
| C07F 9/6587 | (2006.01) |
| C07H 21/00 | (2006.01) |
| A61K 31/7084 | (2006.01) |

(52) U.S. Cl.
CPC ........ C07D 519/00 (2013.01); C07B 2200/13 (2013.01)

(58) Field of Classification Search
CPC ... C07D 519/00; C07B 2200/13; A61P 35/00; C07F 9/6587; C07H 21/00; A61K 31/7084
See application file for complete search history.

(56) References Cited

U.S. PATENT DOCUMENTS

| 5,547,941 | A | 8/1996 | Battistini et al. |
| 7,569,555 | B2 | 8/2009 | Karaolis |
| 7,592,326 | B2 | 9/2009 | Karaolis |
| 7,709,458 | B2 | 5/2010 | Karaolis et al. |
| 8,076,303 | B2 | 12/2011 | Iyer et al. |
| 9,549,944 | B2 | 1/2017 | Dubensky, Jr. et al. |
| 9,695,212 | B2 | 7/2017 | Dubensky, Jr. et al. |
| 9,718,848 | B2 | 8/2017 | Adams et al. |
| 9,724,408 | B2 | 8/2017 | Dubensky, Jr. et al. |
| 9,770,467 | B2 | 9/2017 | Dubensky, Jr. et al. |
| 9,809,597 | B2 | 11/2017 | Burai et al. |
| 10,011,630 | B2 | 7/2018 | Vemnejoul et al. |
| 10,106,574 | B2 | 10/2018 | Altman et al. |
| 2014/0329889 | A1 | 11/2014 | Vance et al. |
| 2017/0319680 | A1 | 11/2017 | Ishii et al. |
| 2017/0340658 | A1 | 11/2017 | Vemnejoul et al. |

FOREIGN PATENT DOCUMENTS

| CN | 102199183 B | 12/2013 |
| EP | 1729781 B1 | 12/2006 |
| EP | 1740192 B1 | 1/2007 |
| EP | 1968612 B1 | 3/2016 |
| JO | 20190194 P | 8/2018 |
| WO | 2009133560 A1 | 11/2009 |
| WO | 2014099824 A1 | 6/2014 |
| WO | 2014179335 A1 | 11/2014 |
| WO | 2014189805 A1 | 11/2014 |
| WO | 2015074145 A1 | 5/2015 |
| WO | 2015077354 A1 | 5/2015 |
| WO | 2015185565 A1 | 12/2015 |
| WO | 2016100261 A2 | 6/2016 |
| WO | 2016120305 A1 | 8/2016 |
| WO | 2016145102 A1 | 9/2016 |

(Continued)

OTHER PUBLICATIONS

Notification to request examination, issued in corresponding Australian Patent Application No. 2019322722 dated Oct. 3, 2021.

(Continued)

*Primary Examiner* — John M Mauro
(74) *Attorney, Agent, or Firm* — Buchanan Ingersoll & Rooney PC

(57) ABSTRACT

The present invention provides crystals of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) ammonium salts, Compound (I) sodium salts, or Compound (I), possessing a potential to be used as drug substance in pharmaceuticals.

[Chem. 1]

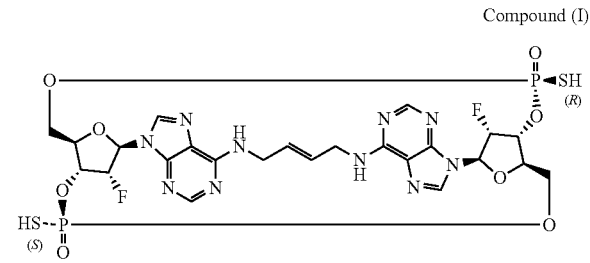

Compound (I)

12 Claims, 28 Drawing Sheets
Specification includes a Sequence Listing.

(56) References Cited

FOREIGN PATENT DOCUMENTS

| WO | 2017011622 A1 | 1/2017 |
|---|---|---|
| WO | 2017011920 A1 | 1/2017 |
| WO | 2017027645 A1 | 2/2017 |
| WO | 2017027646 A1 | 2/2017 |
| WO | 2017040670 A1 | 3/2017 |
| WO | 2017075477 A1 | 5/2017 |
| WO | 2017093933 A1 | 6/2017 |
| WO | 2017123657 A1 | 7/2017 |
| WO | 2017123669 A1 | 7/2017 |
| WO | 2017161349 A1 | 9/2017 |
| WO | 2017175156 A1 | 10/2017 |
| WO | 2018060323 A1 | 4/2018 |
| WO | 2018098203 A1 | 5/2018 |
| WO | 2018140831 A2 | 8/2018 |
| WO | 2018152450 A1 | 8/2018 |
| WO | 2018152453 A1 | 8/2018 |
| WO | 2018198076 A1 | 11/2018 |
| WO | 2018198084 A1 | 11/2018 |

OTHER PUBLICATIONS

Lioux, T., et al., "Design, Synthesis, and Biological Evaluation of Novel Cyclic Adenosine-Inosine Monophosphate cAIMP) Analogs That Activate Stimulator of Interferon Genes (STING)", J. Med. Chem., 2016,10253-10267, vol. 59 (22), American Chemical Society.

Yi, G., et al., "Single Nucleotide Polymorphisms of Human STING Can Affect Innate Immune Response to Cyclic Dinucleotides", PLoS One 8(10), 2013, e77846, doi:10.1371/journal.pone.0077846.

Xia. T., et al., "Deregulation of STING Signaling in Colorectal Carcinoma Constrains DNA Damage Responses and Correlates With Tumorigenesis", Cell Reports 14, Jan. 12, 2016, 282-297.

Woo, S.R, et al. "STING-dependent Cytosolic DNA Sensing Mediates Innate Immune Recognition of Immunogenic Tumors", Immunity 41, Nov. 20, 2014, 830-842.

Ohkuri, T., et al., "Protective Role of STING Against Gliomagenesis: Rational Use of STING Agonist in Anti-glioma Immunotherapy", Oncoimmunology 4-4, Apr. 2015, e999523.

Zhu, Q., et al., "Cutting edge: STING mediates protection against colorectal tumorigenesis by governing the magnitude of intestinal inflammation" J. Immunol. 193, Oct. 15, 2014; 4779-4782.

Corrales, L., et al., "Direct Activation of STING in the Tumor Microenvironment Leads to Potent and Systemic Tumor Regression and Immunity", Cell Reports 11, May 19, 2015, 1018-1030.

Curran, E., et al., "STING Pathway Activation Stimulates Potent Immunity against Acute Myeloid Leukemia", Cell Reports 15, Jun. 14, 2016, 2357-2366.

Corrales, L., et al., "The host STING pathway at the interface of cancer and immunity", The Journal of Clinical Investigation 126-7, Jul. 2016, 2404-2411.

Endo, T., et al., "In situ cancer vaccination with a replication-conditional HSV for the treatment of liver metastasis of colon cancer," Cancer Gene Therapy (2002) 9, 142-148, Nature Publishing Group, www.nature.com/cgt.

Kozlowski, J.M., et al., "Metastatic Behavior of Human Tumor Cell Lines Grown in the Nude Mouse," Cancer Research vol. 44, 3522-3529, Aug. 1984.

Rajendran, S., et al., "Murine Bioluminescent Hepatic Tumour Model," JOVE: Journal of Visualized Experiments, www.jove.com, 2010, pp. 1-3.

Tang, C.H., et al., "Agonist-Mediated Activation of STING Induces Apoptosis in Malignant B Cells" Cancer Research, 76(8), Mar. 7, 2016, 2137-2152.

Xia ,T., et al., "Recurrent Loss of STING Signaling in Melanoma Correlates with Susceptibility to Viral Oncolysis" Cancer Research 76(22), 6747-6759, Sep. 28, 2016.

Chandra, D, et al., "STING ligand c-di-GMP improves cancer vaccination against metastatic breast cancer", Cancer Immunol Res. Sep. 2014, 2(9), 901-910.

McManus, F.P., et al., "Preparation of Covalently Linked Complexes Between DNA and 06-Alkylguanine-DNA Alkyltransferase Using Interstrand Cross-Linked DNA," Bioconjugate Chem., 2013, vol. 24, 224-233.

Booth, J., et al., "Effect of Linker Length on DNA Duplexes Containing a Mismatched 06-2'-Deoxyguanosine-alkyl Interstrand Cross-Link," Nucleic Acids Symposium, Series. No. 52, Sep. 2008, 431-432.

Denisov, A., et al., "Structural Basis of Interstrand Cross-Link Repair by O6-alkylguanine DNA alkyltransferase," Org. Biomol. Chem., 2017, vol. 15, pp. 8361-8370.

McManus, F., et al., "O4-Alkyl-2'deoxythymidine Cross-Linked DNA to Probe Recognition and Repair by O6-alkylguanine DNA Alkyltransferases", Org. Biomol. Chem., 2012 vol. 10, 7078-7090.

Urata, H., et al., "Regio- and Diastereo-Selectivity of Montmorillonite-Catalyzed Oligomerization of Racemic Adenosine 5'-Phosphorimidazolide", Nucleosides, Nucleotides, and Nucleic Acids, 2008 vol. 27, 421-430.

Examination Report for Indian Application No. 202047052666 filed Dec. 3, 2020 dated Mar. 11, 2022.

Response to Notification Before Examination According To Section 18 Of The Law And Regulation 36, dated Jun. 20, 2021 in corresponding Israeli Patent Application No. 278485, filed on Sep. 5, 2021.

Office Action Response and Amended Claims for corresponding European Application No. 19850709.7, dated May 6, 2021.

Office Action and Search Report for corresponding Taiwanese Application No. TW 108128873 dated Sep. 21, 2020, with English translation.

Notice of Allowance for corresponding Taiwanese Application No. TW 108128873 dated Dec. 3, 2020, with English translation.

Application Submission Documents (Replacement Claims and Drawings) for Taiwanese Counterpart Patent Application No. 108128873 with English translation, Nov. 2020.

Notification Before Examination According To Section 18 Of The Law And Regulation 36, issued in corresponding Israeli Patent Application No. 278485 dated Jun. 20, 2021, and English Translation.

International Search Report (PCT/ISA/210) dated Oct. 21, 2019, by the Japanese Patent Office as the International Searching Authority for International Application No. PCT/JP2019/031951.

Notice of Allowance for corresponding Application No. JP P2019-565031 dated Sep. 8, 2020.

Office Action for corresponding Application No. JP P2019-565031 dated Aug. 11, 2020.

Written Opinion (PCT/ISA/237) dated Oct. 21, 2019, by the Japanese Patent Office as the International Searching Authority for International Application No. PCT/JP2019/031951.

Lioux et al., Design, Synthesis, and Biological Evaluation of Novel Cyclic Adenosine-Inosine Monophosphate (cAIMP) Analogs That Activate Stimulator of Interferon Genes (STING), Journal of Medicinal Chemistry, vol. 59, No. 22, 2016, pp. 10253-10267.

"Polymorphism of molecular crystals", by J. Bernstein, Moscow, Nauka, 2007, Chapter 7.3.2 Bioavailability, 2007, p. 324-p. 330 (English and Russian Translation).

"Crystalline Polymorphism of Organic Compounds" by Mino R. Caira; Topics in Current Chemistry,vol. 198; Springer Verlag Berlin Heidelberg 1998.

Russian Office Action for Application No. 2020136403 dated Feb. 28, 2022 (With English Translation).

Response to the Communication pursuant to Rules 70(2) and 70a(2) of the European Patent Convention, dated Apr. 12, 2022 in corresponding EP Application No. EP 19850709, filed on Aug. 14, 2019.

Examination Report No. 1 for Australian application No. 2019322722 dated Jul. 6, 2022.

Communication pursuant to Article 94(3) of the European Patent Convention, dated Nov. 4, 2022 in corresponding EP Application No. EP 19850709, filed on Aug. 14, 2019.

Office Action for Corresponding Application No. CN201980025277. 0, dated Jan. 13, 2023.

Letter accompanying subsequently filed items for amended description pages submitted in replacement of corresponding description pages for EP 19850709.7 dated Apr. 25, 2023.

[Fig. 1]
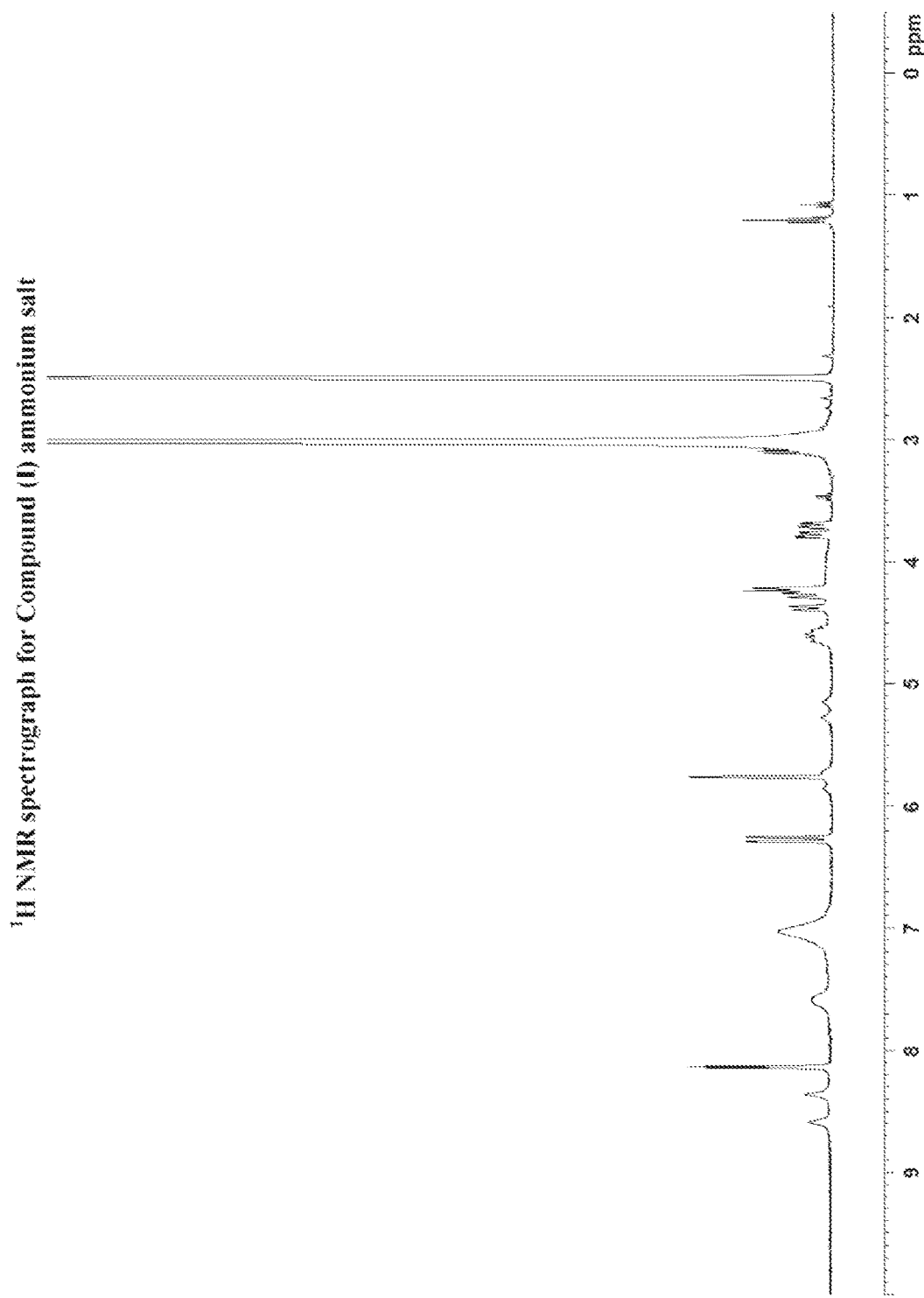

[Fig. 2A]
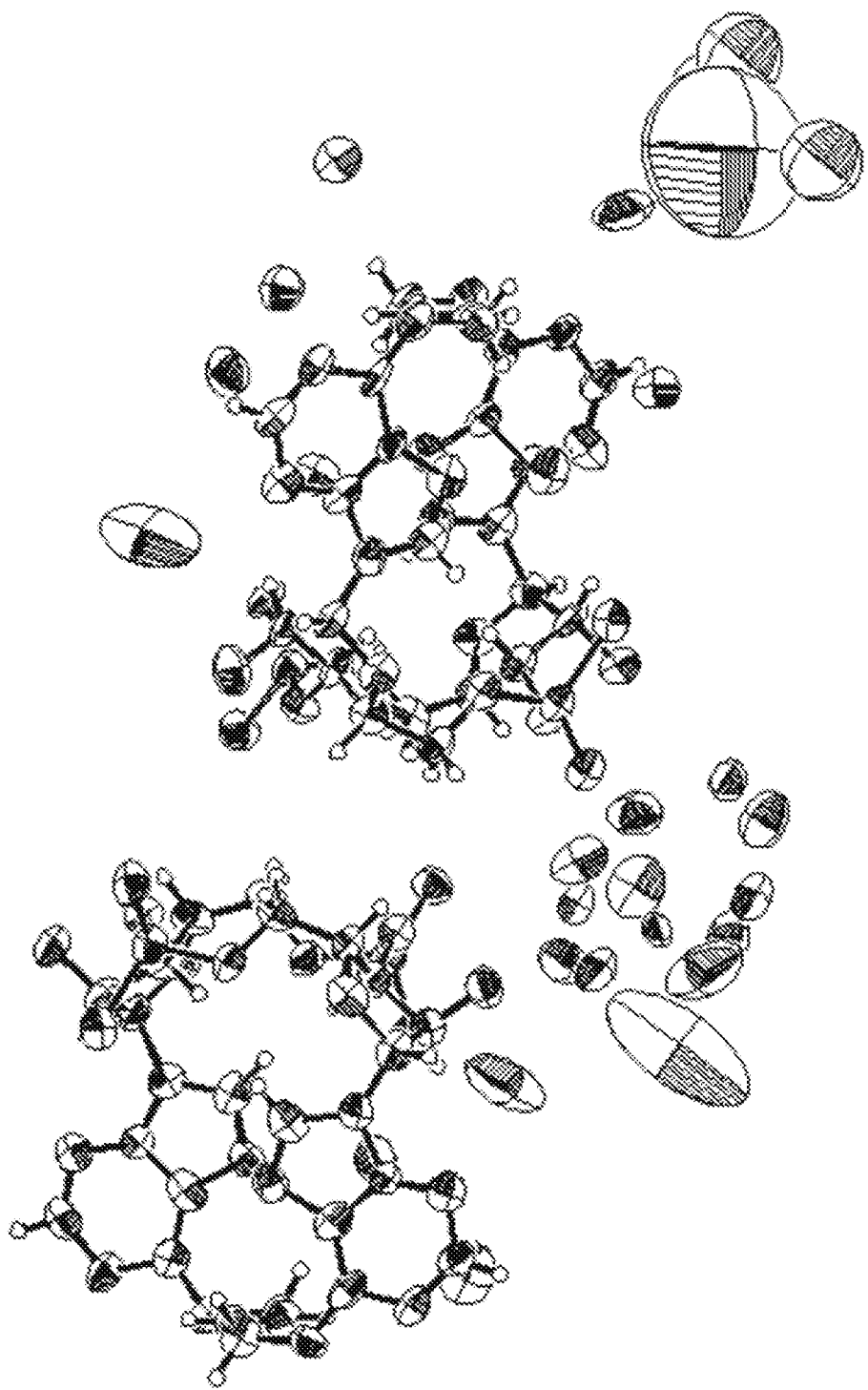
X-ray crystallography result (ORTEP drawings) for a crystal of Compound (I) ammonium salt, where two molecules are present in the assymetric crystal unit

[Fig. 2B]
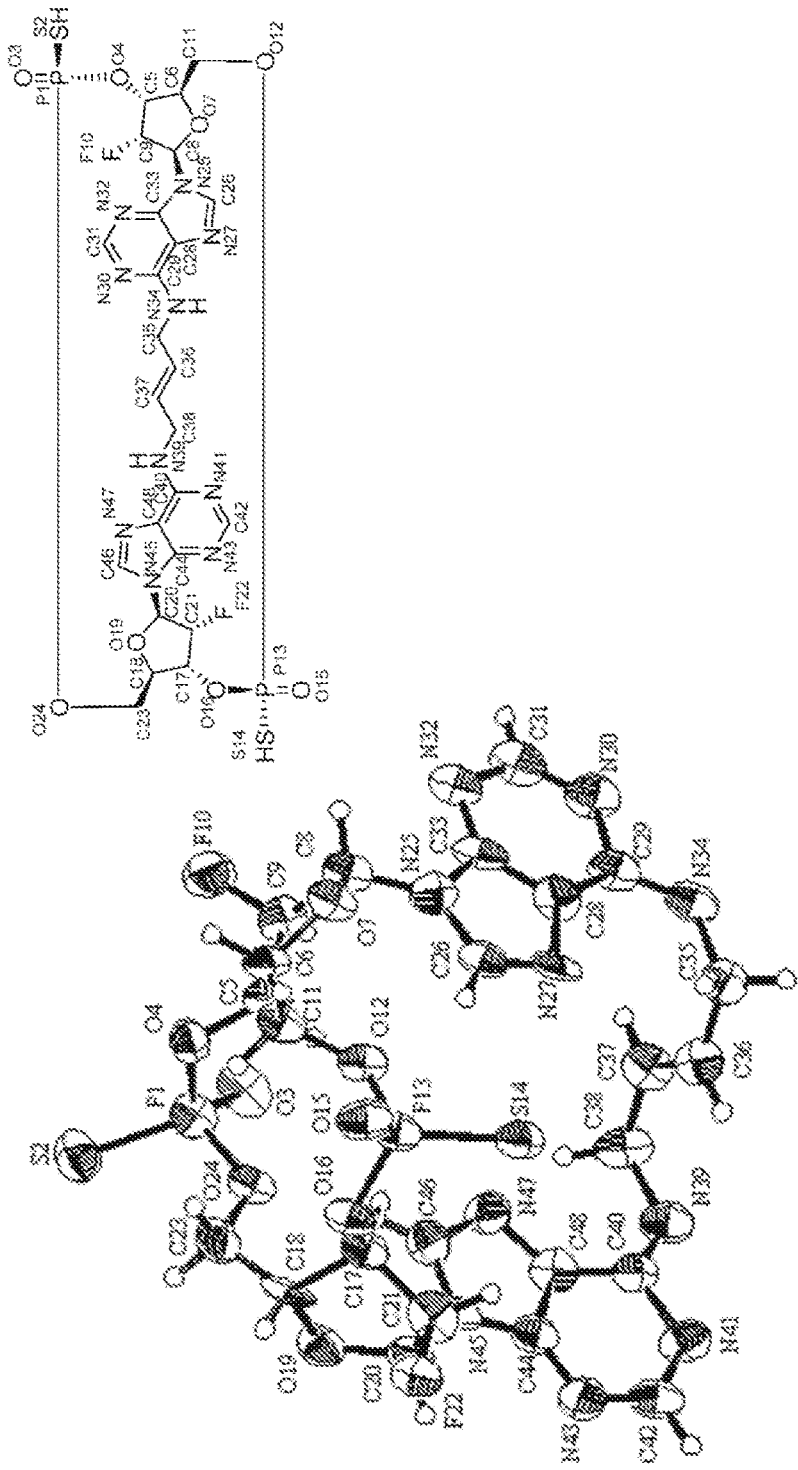

[Fig. 2C]
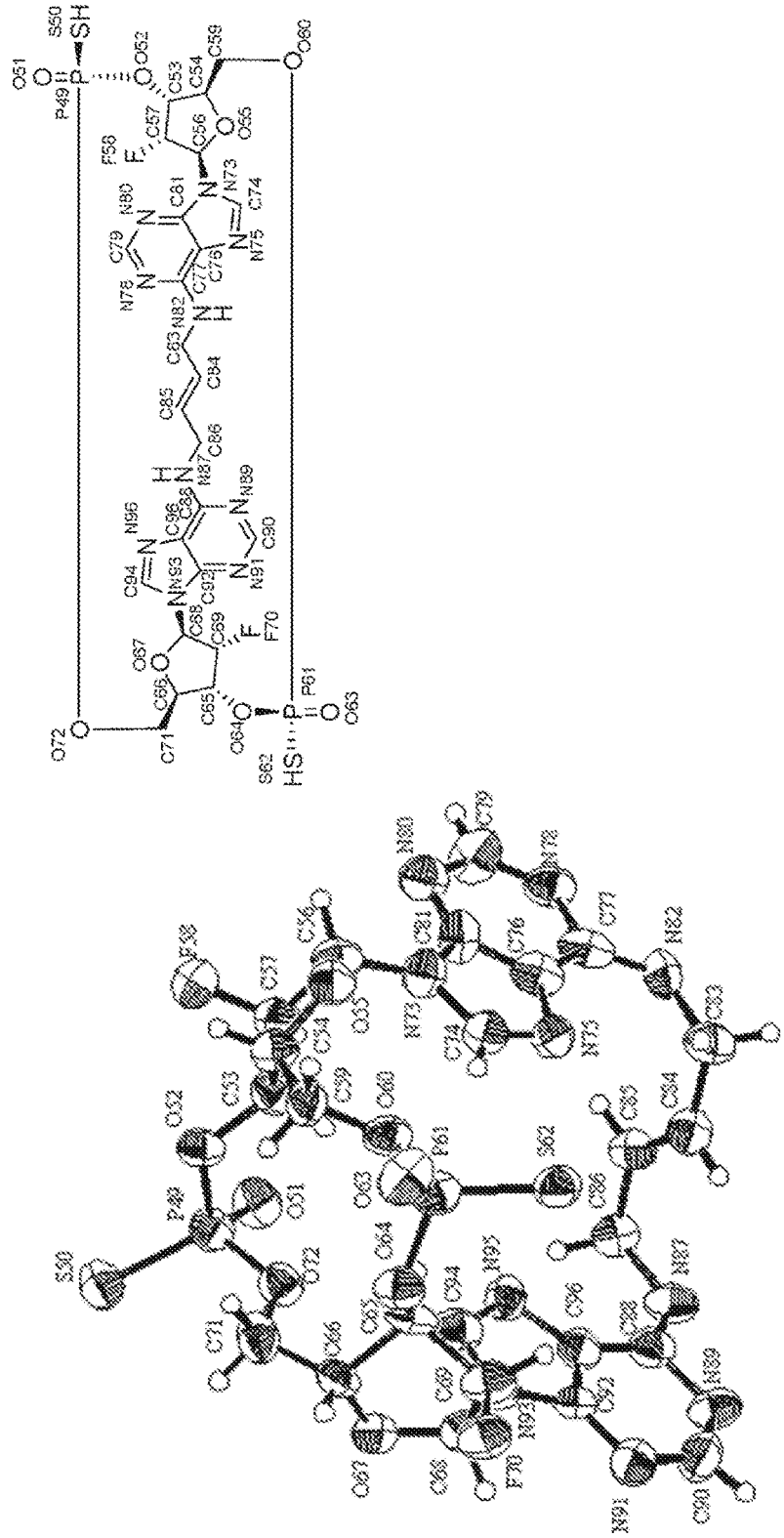

[Fig. 3]
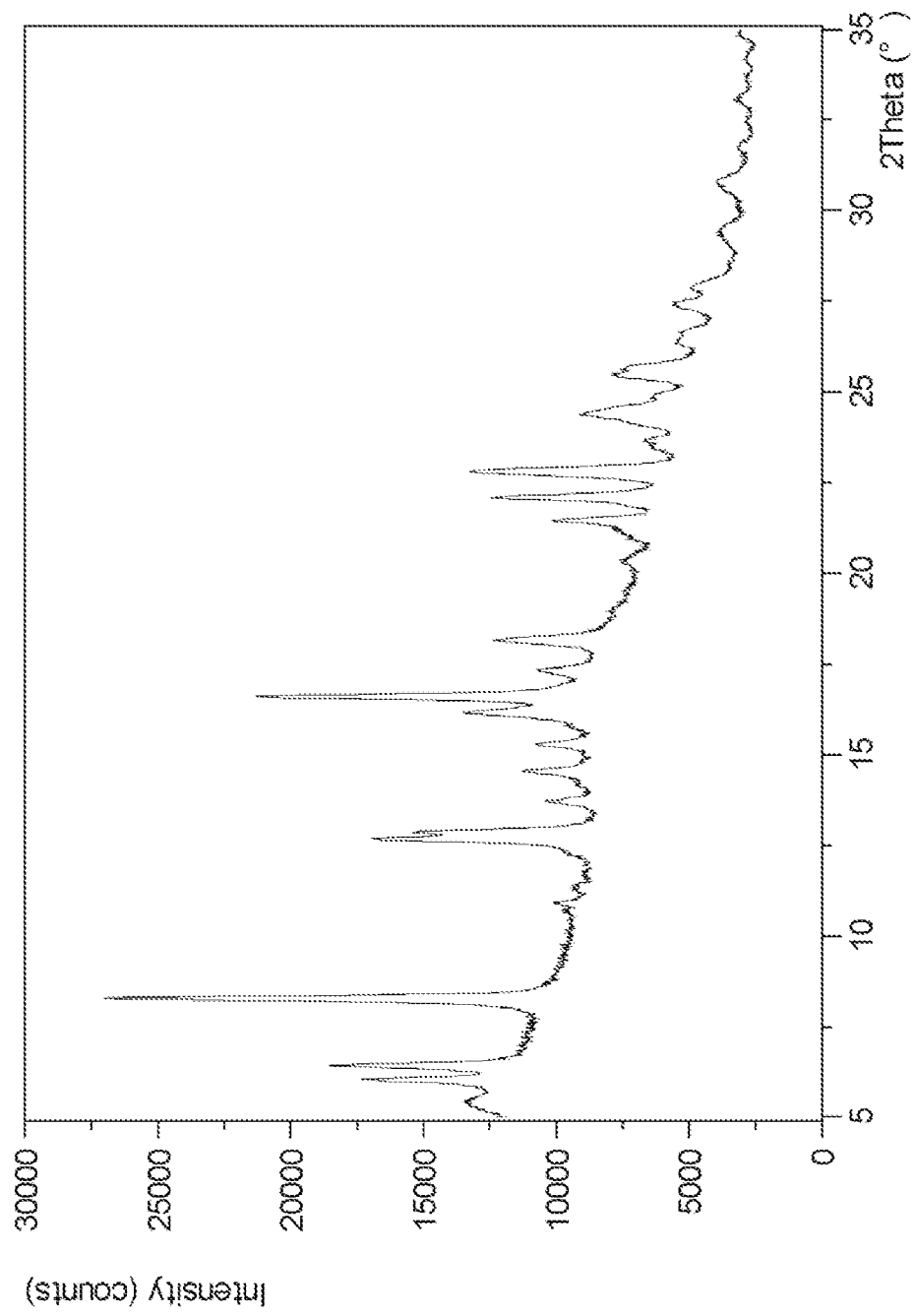

[Fig. 4]
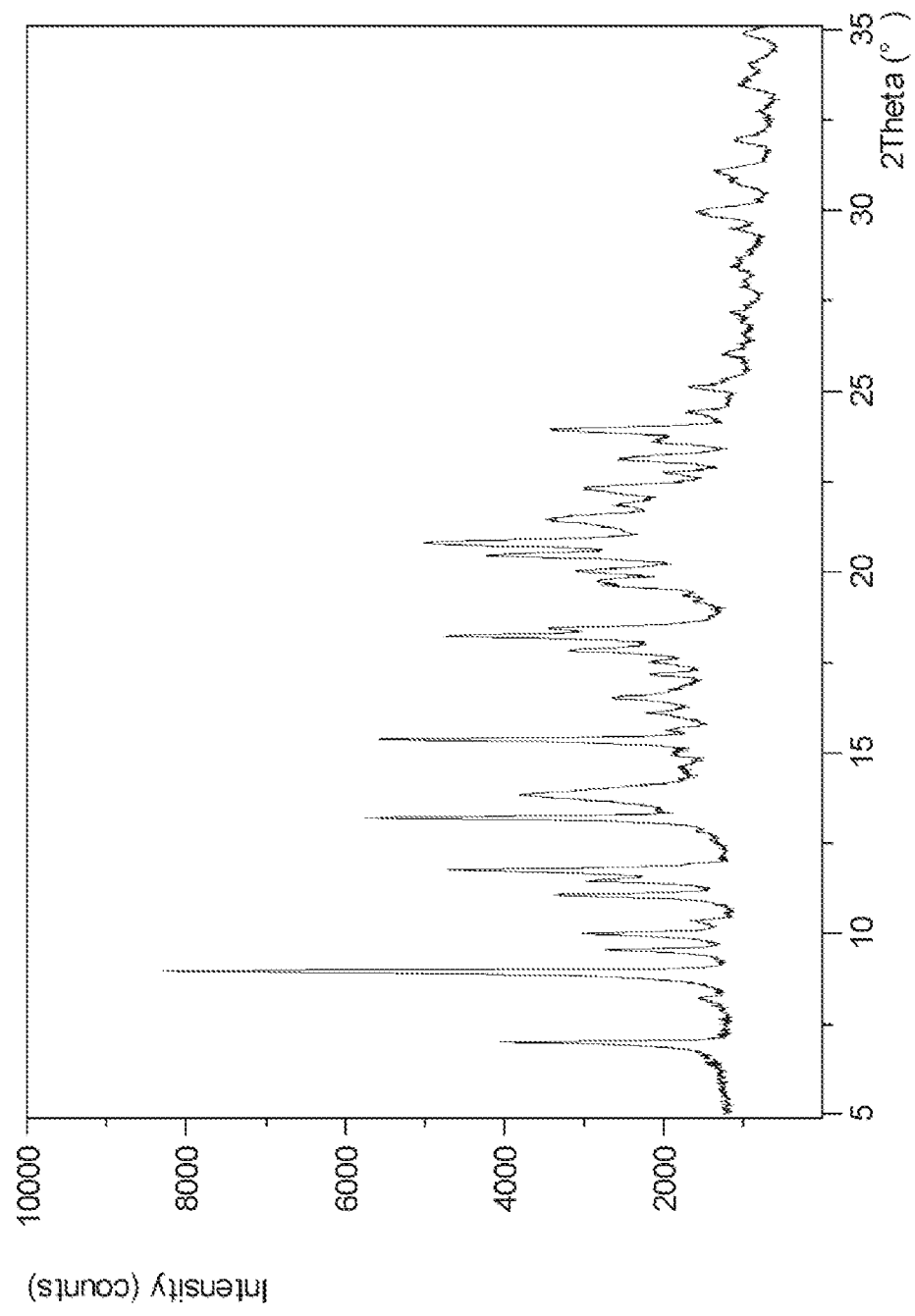

[Fig. 5]
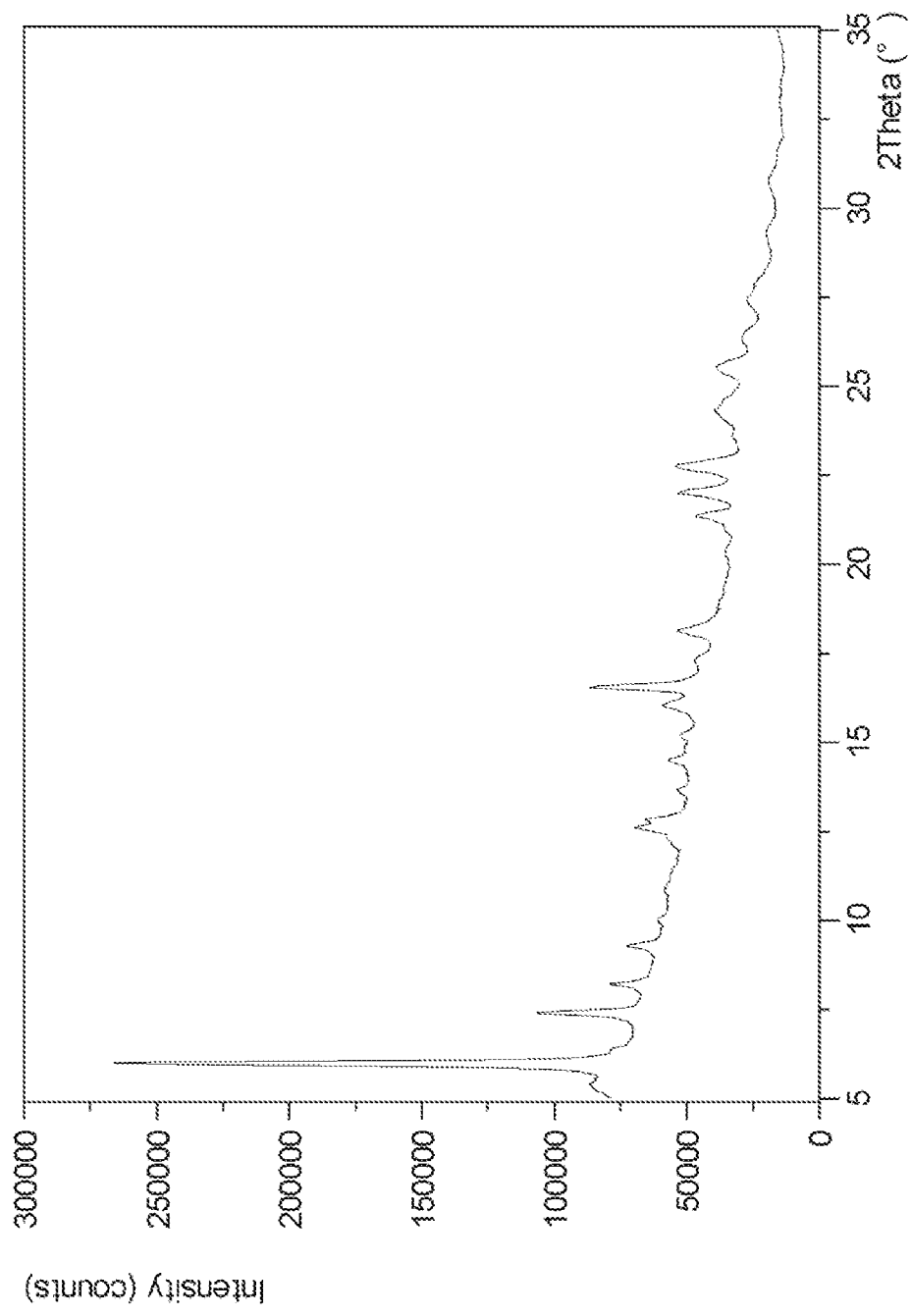

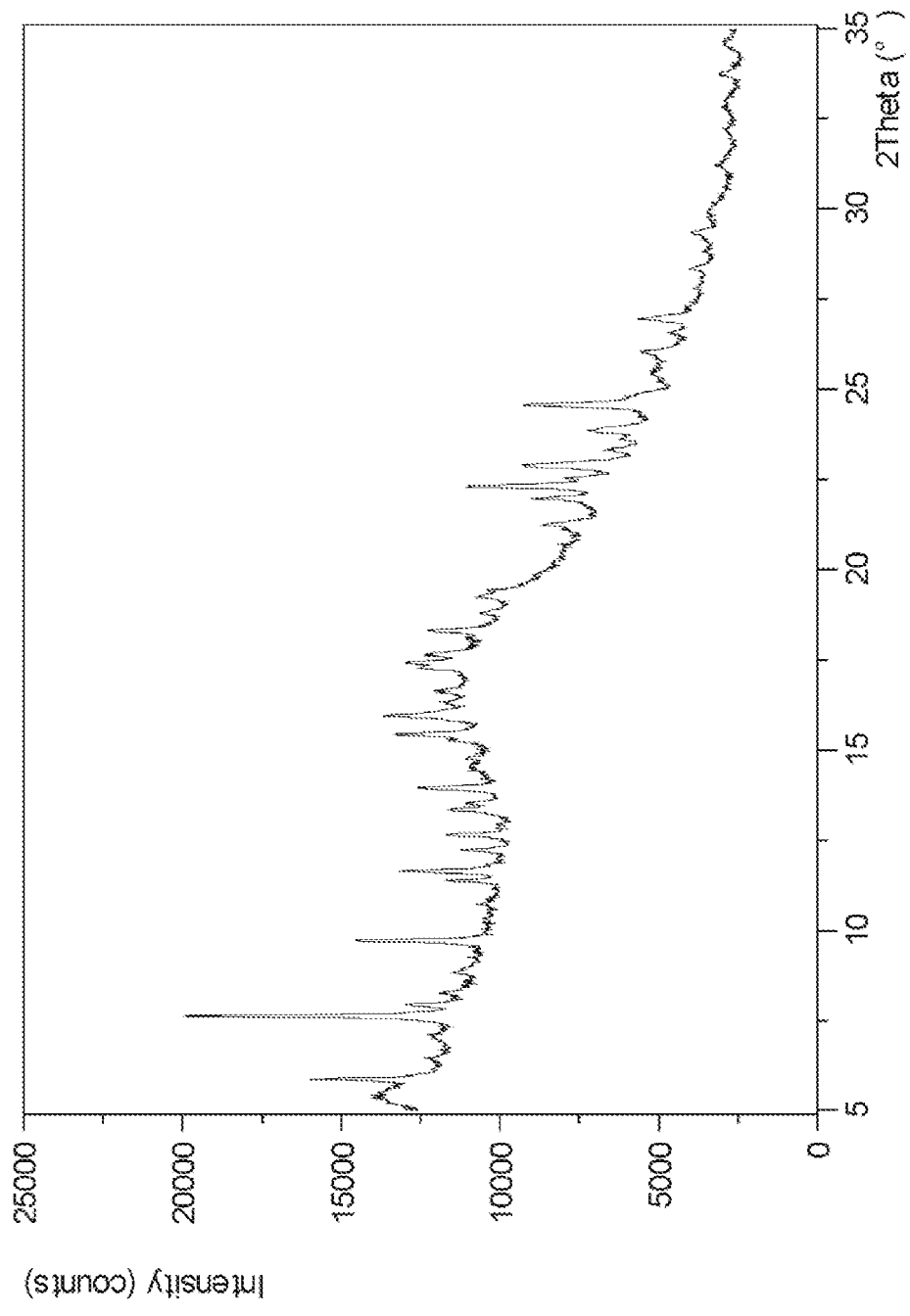
[Fig. 6] Crystal (Form 4) of the Compound (I) di-ammonium salt obtained in Example 4

[Fig. 7]
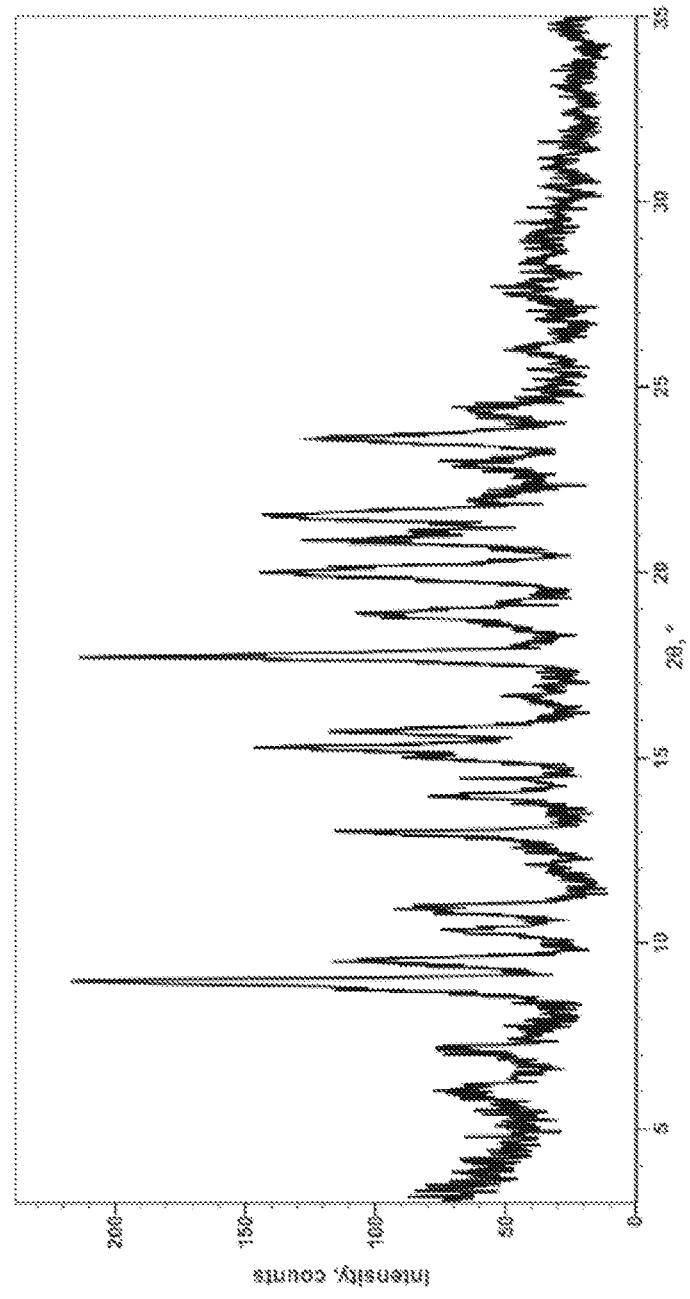

[Fig. 8]
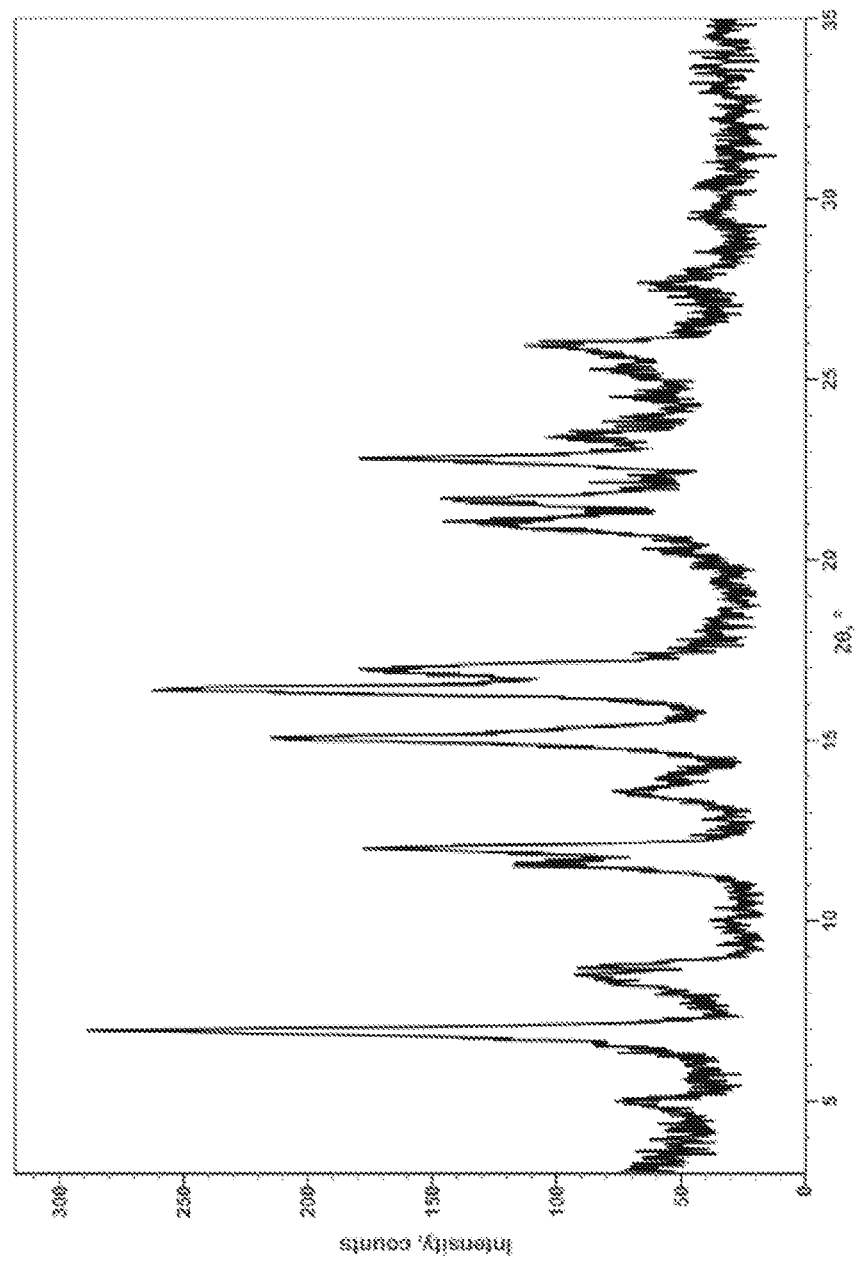

[Fig. 9]
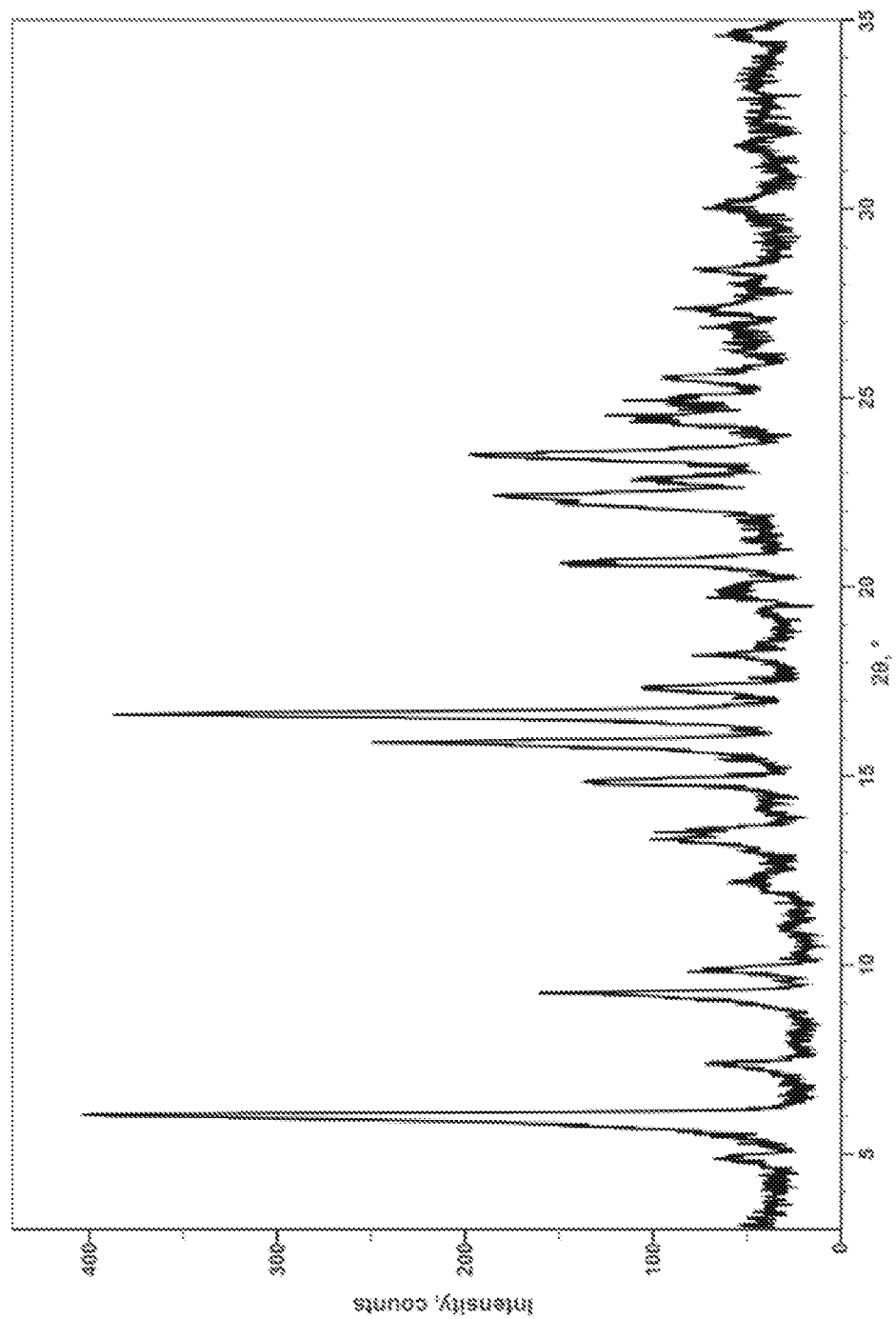

[Fig. 10]
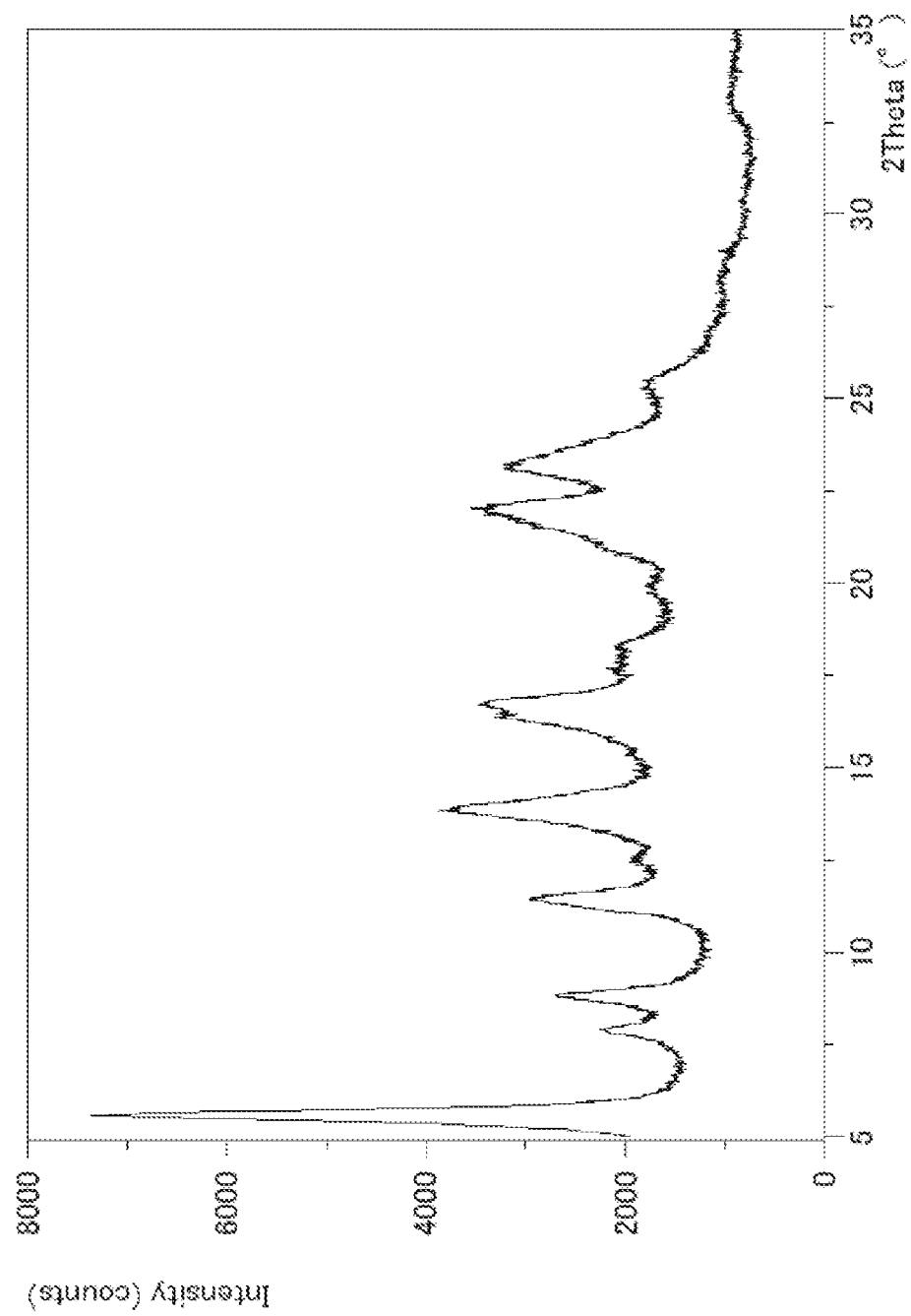

[Fig. 11]
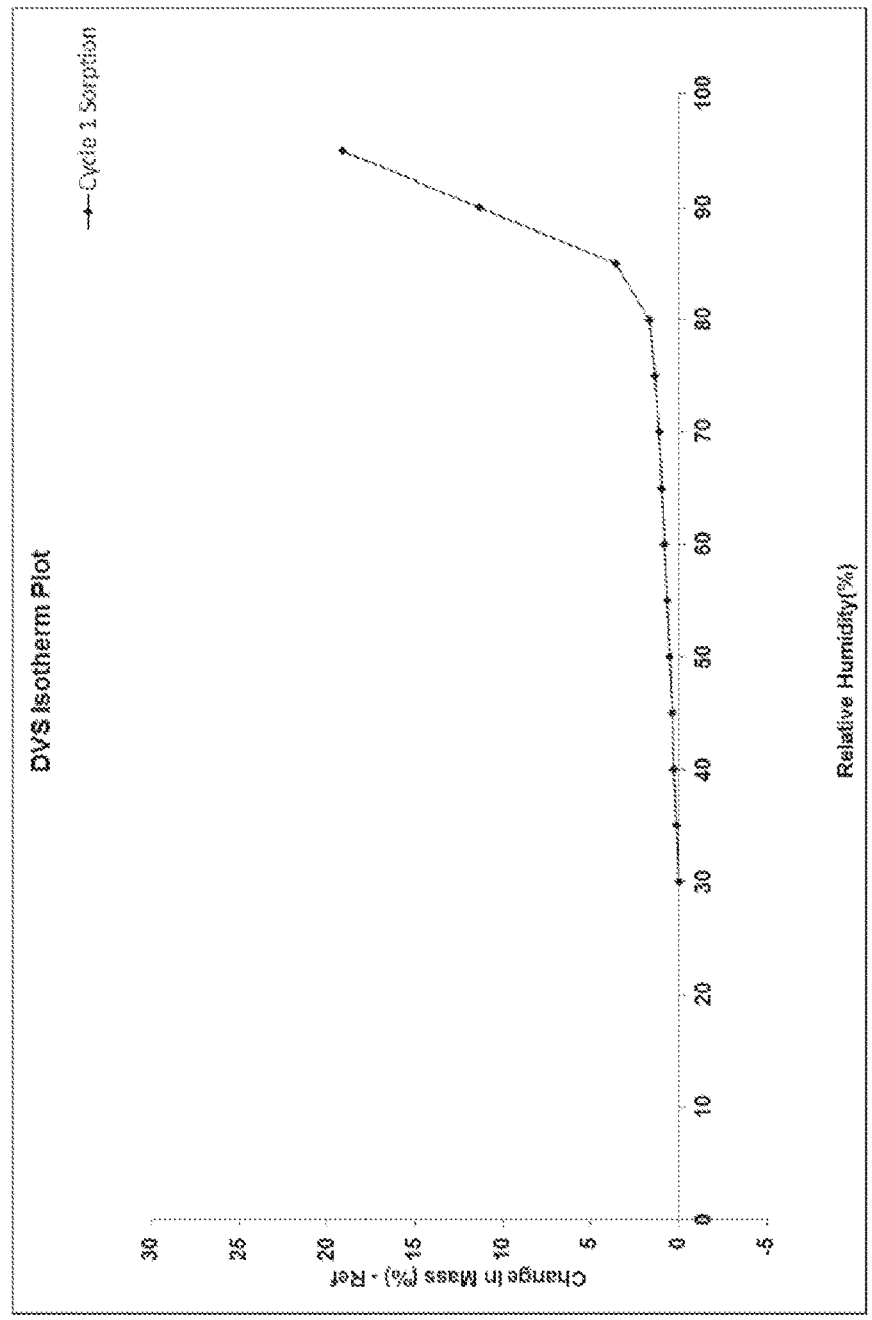

[Fig. 12]
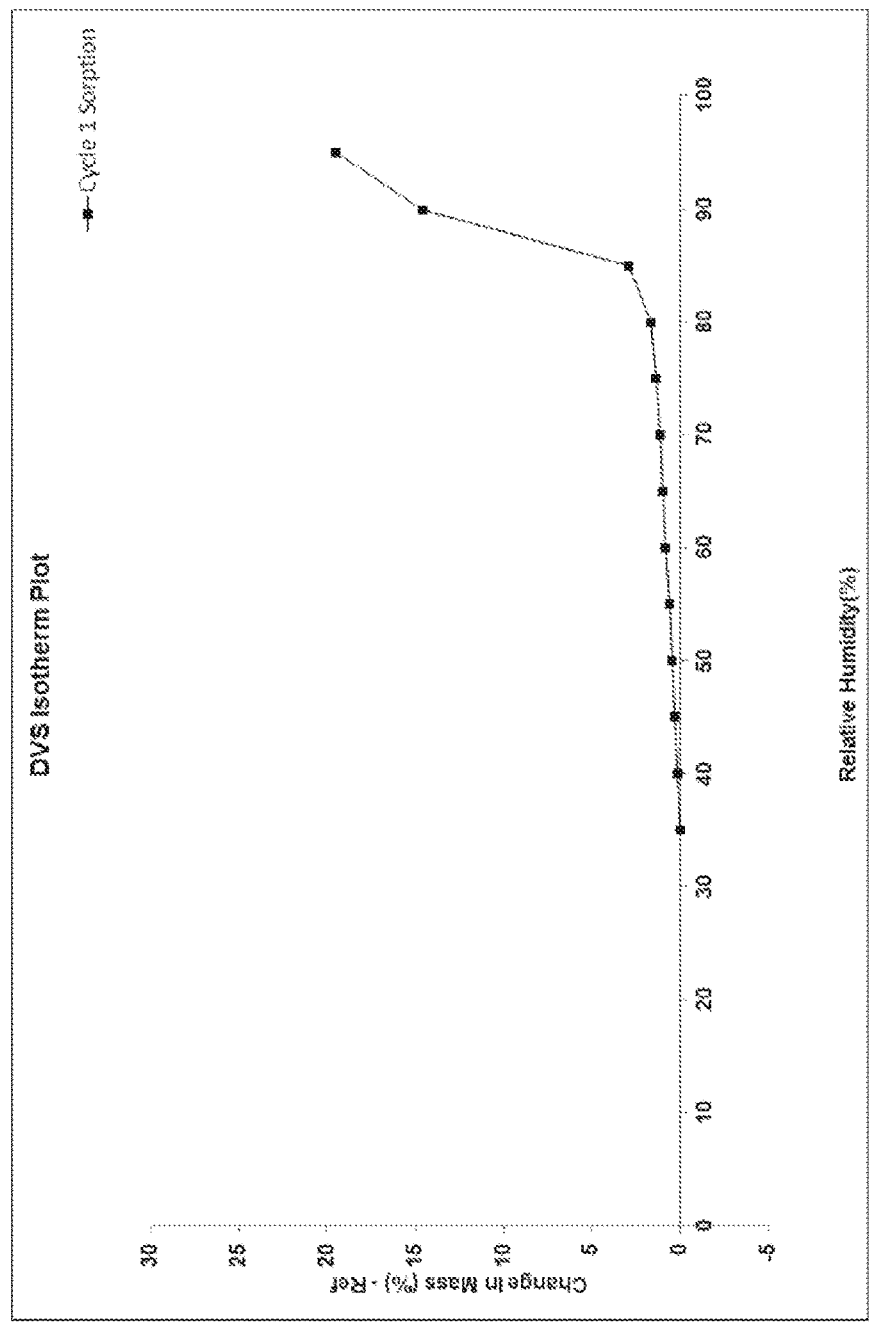

[Fig. 13]
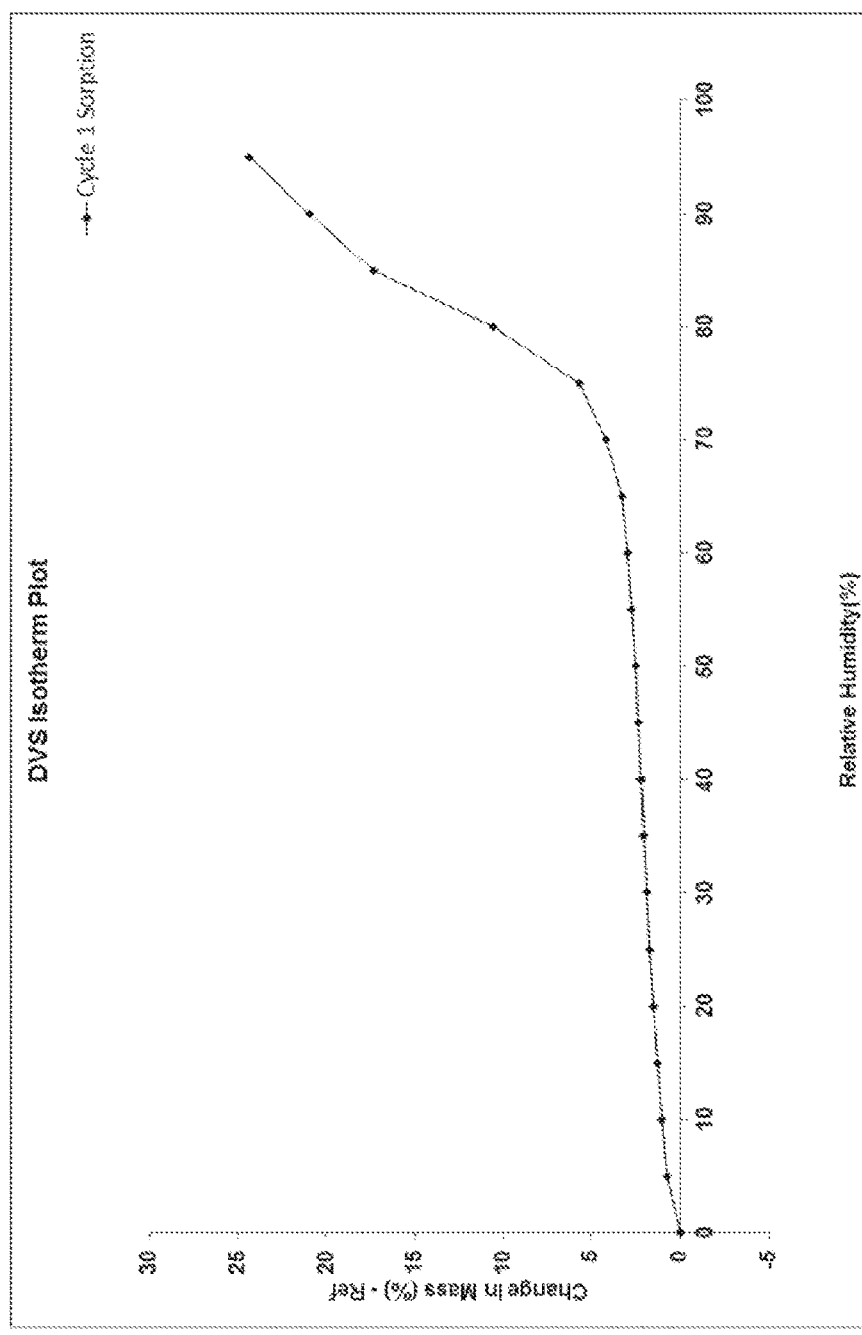

[Fig. 14]
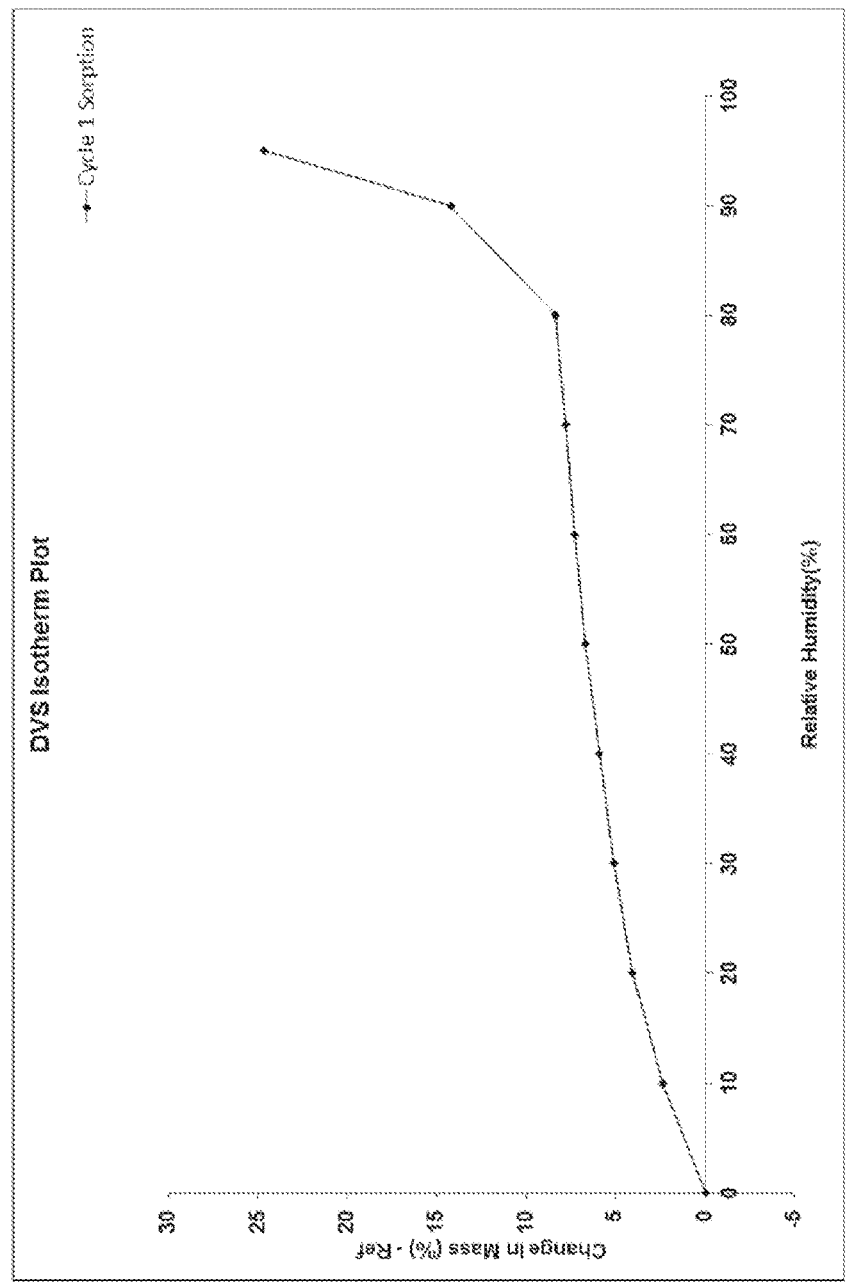
Hygroscopicity of the crystal (Form 6) of the Compound mono-ammonium salt obtained in Example 6

[Fig. 15]
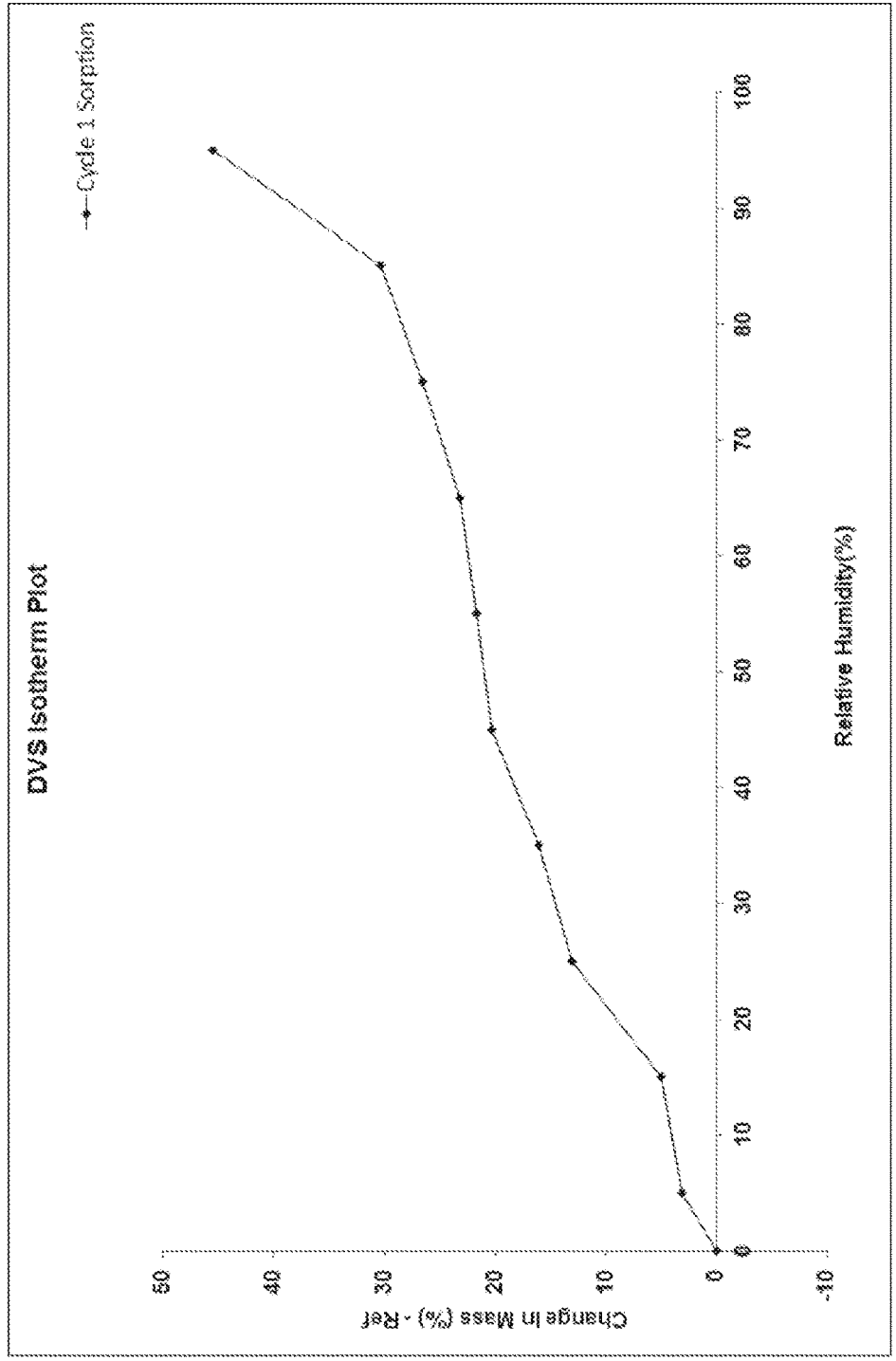

[Fig. 16]
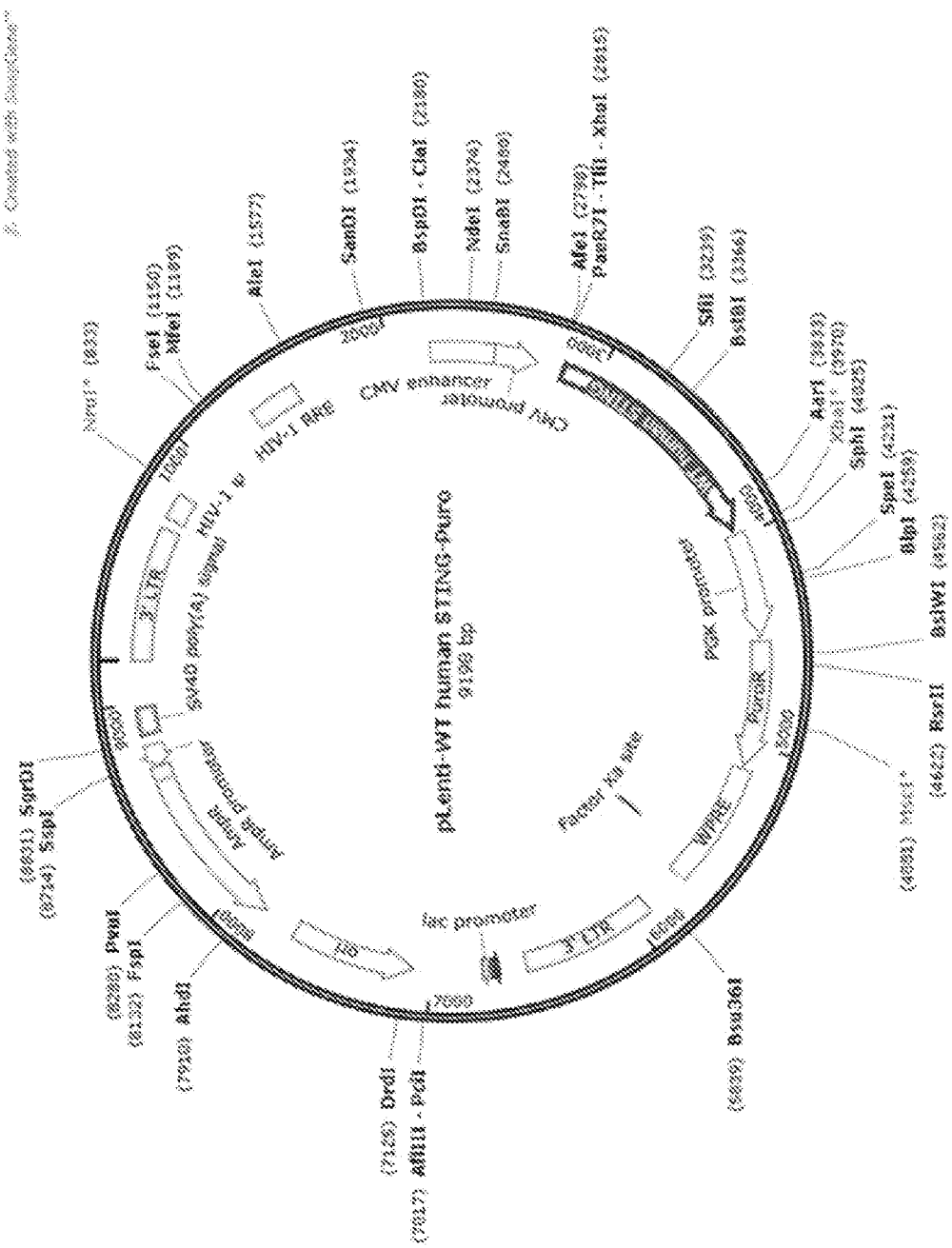

[Fig. 17]
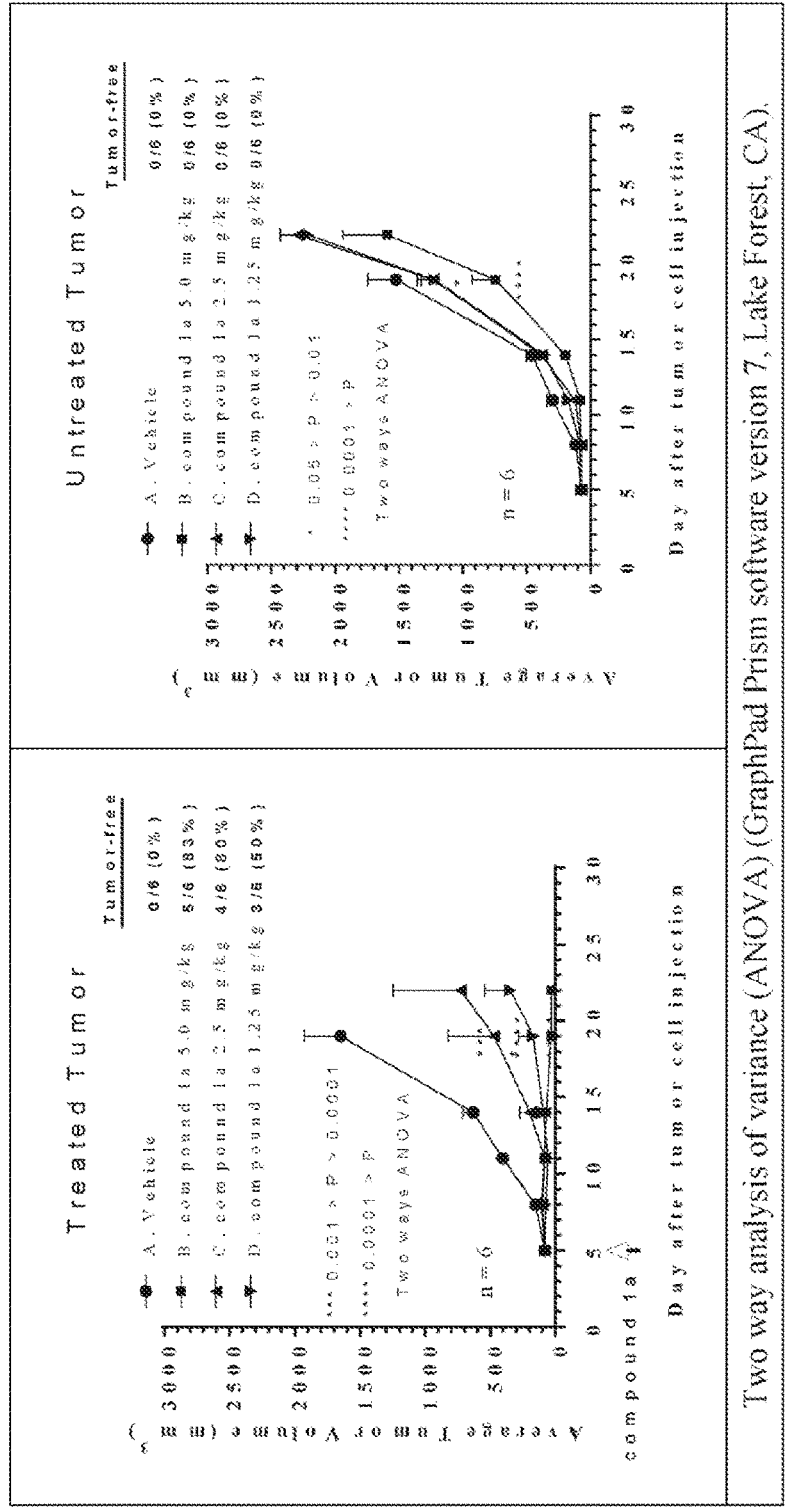
Study A tumor volume plots for treated and untreated tumors in Pharmacological Test Example 6
Two way analysis of variance (ANOVA) (GraphPad Prism software version 7, Lake Forest, CA).

[Fig. 18]
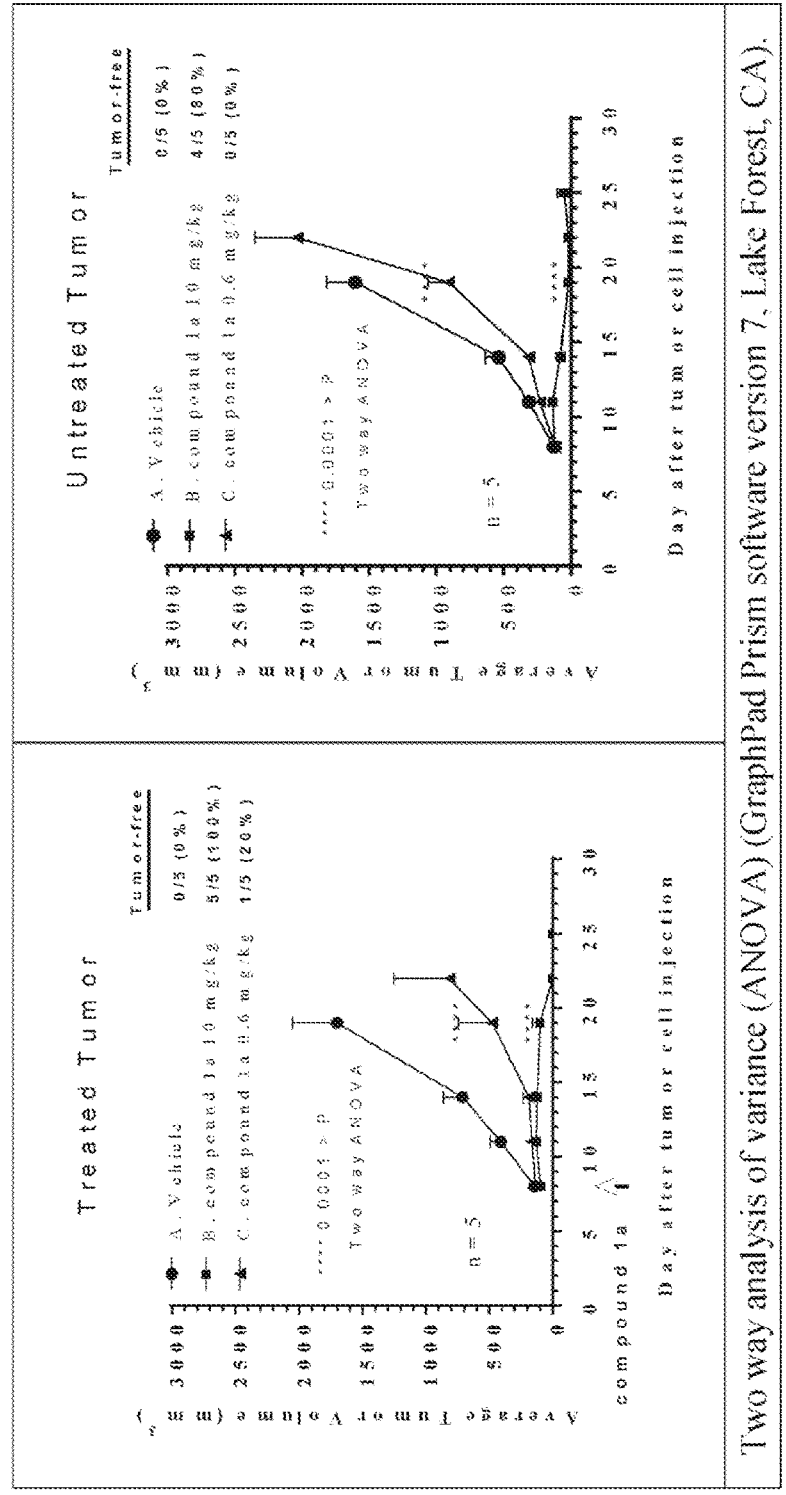
Study B tumor volume plots for treated and untreated tumors in in Pharmacological Test Example 6
Two way analysis of variance (ANOVA) (GraphPad Prism software version 7, Lake Forest, CA).

[Fig. 19]
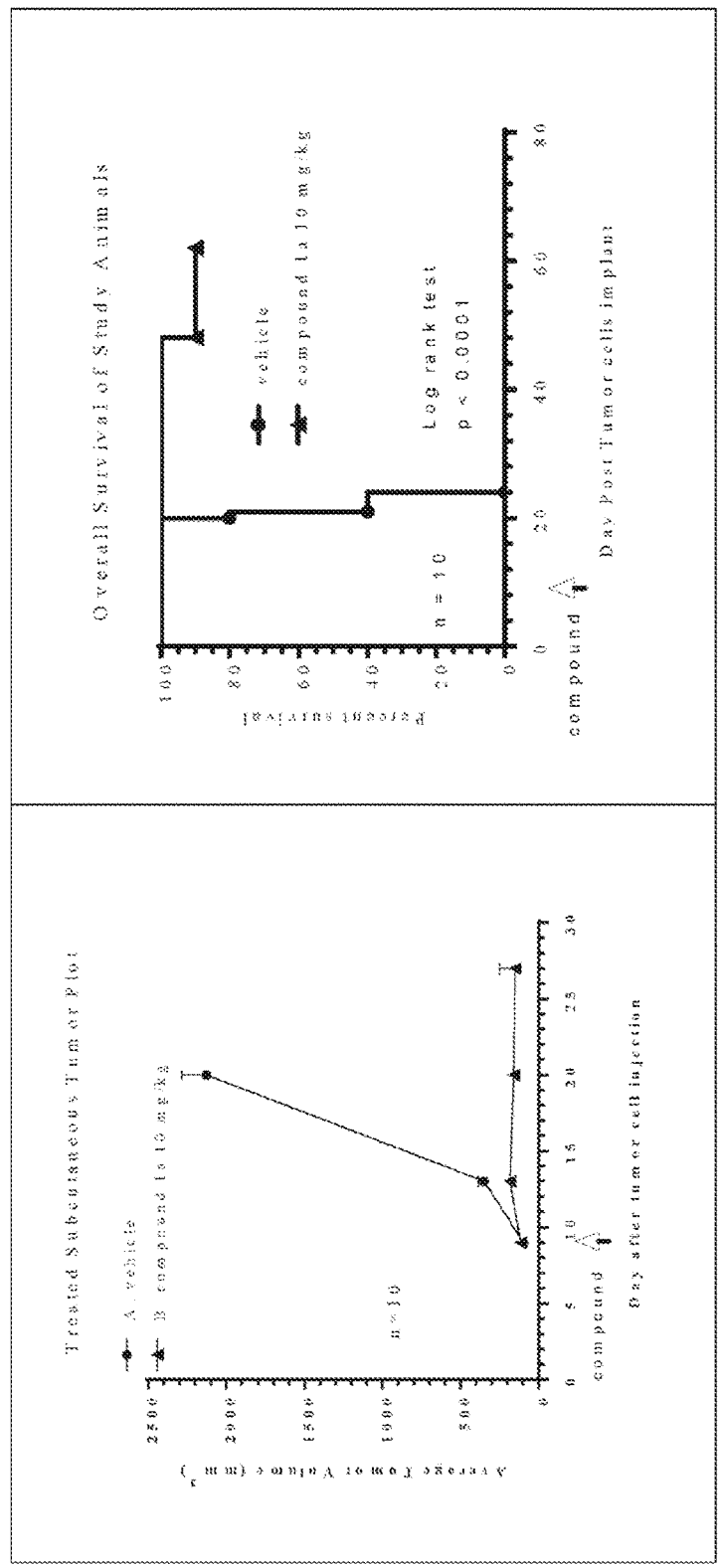

[Fig. 20]
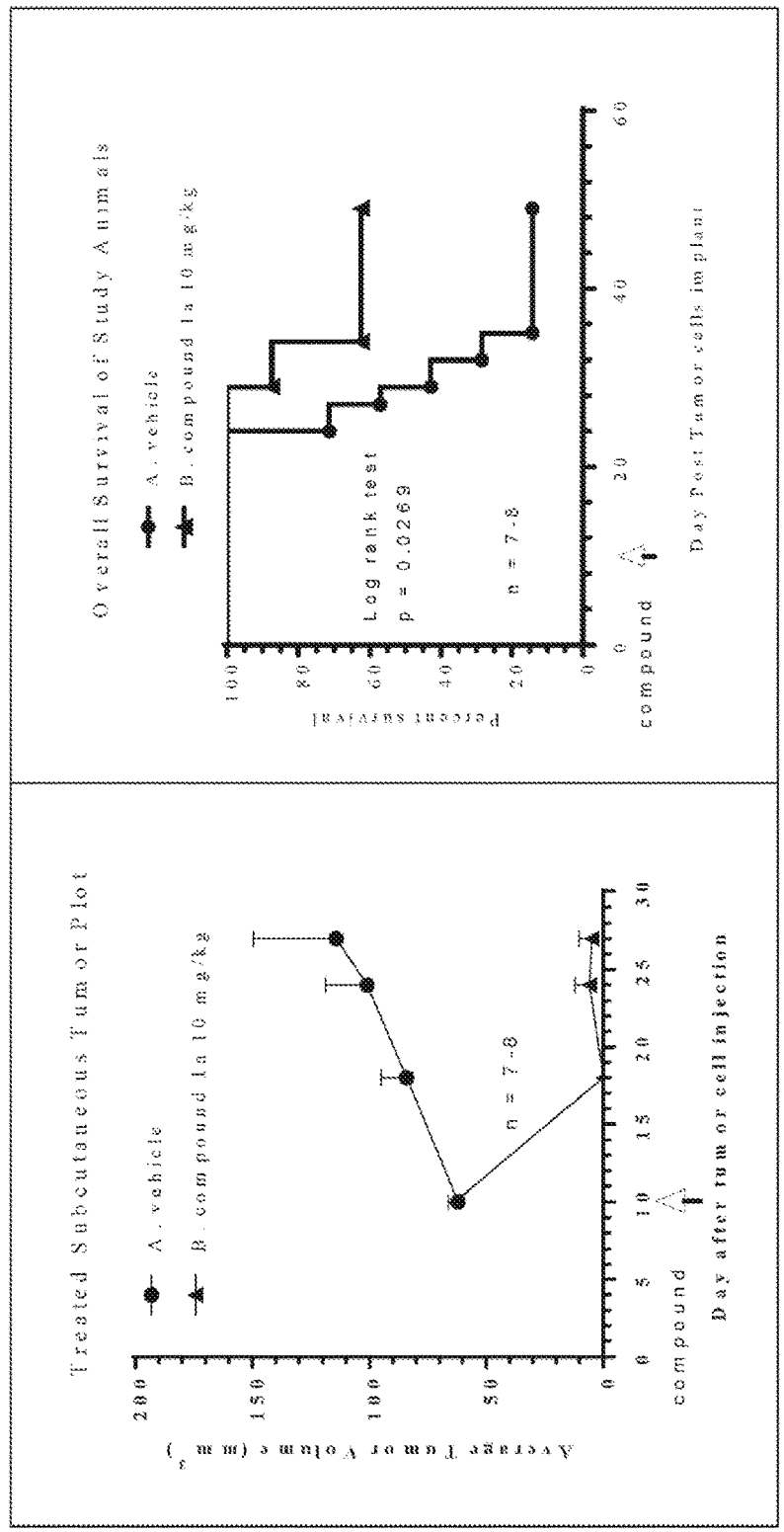

[Fig. 21]
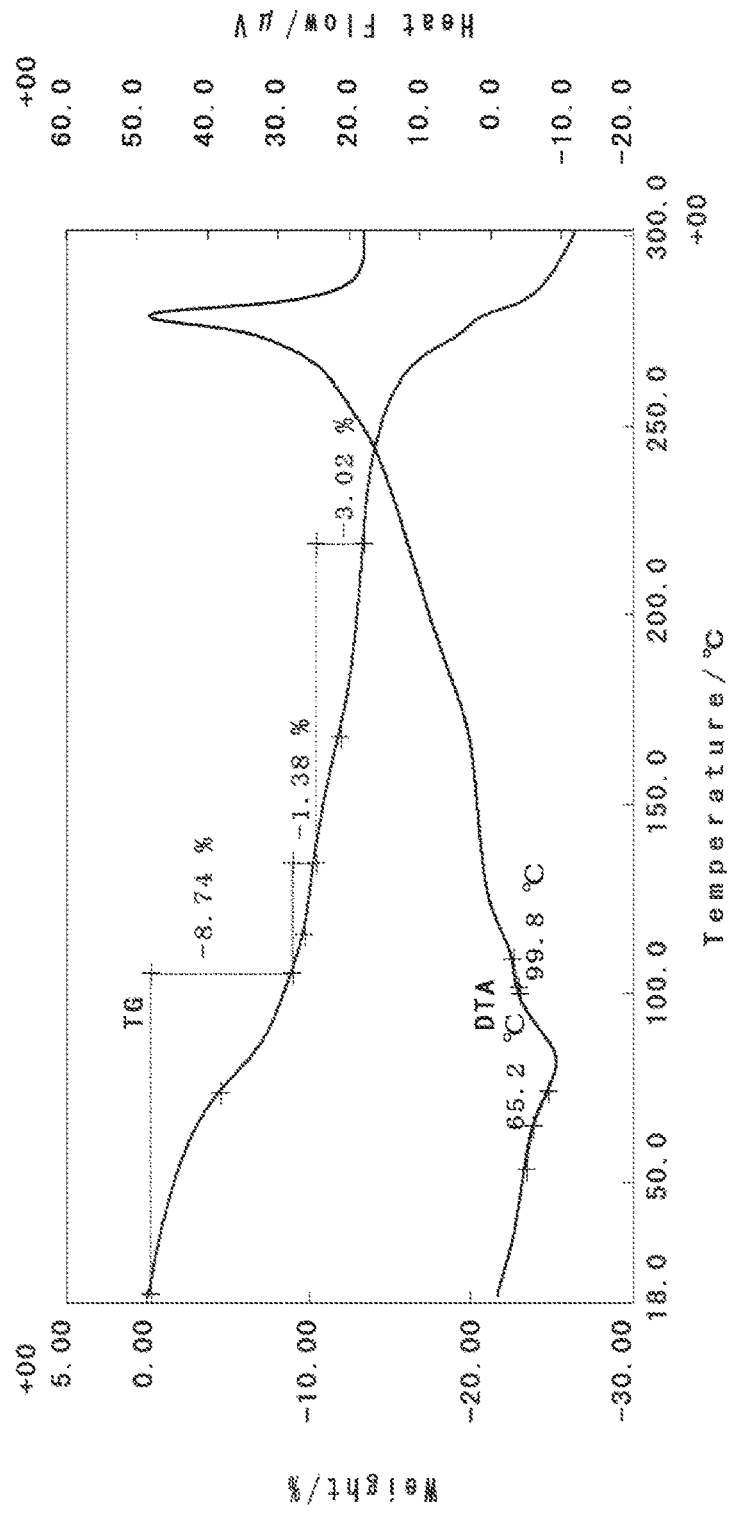

[Fig. 22]
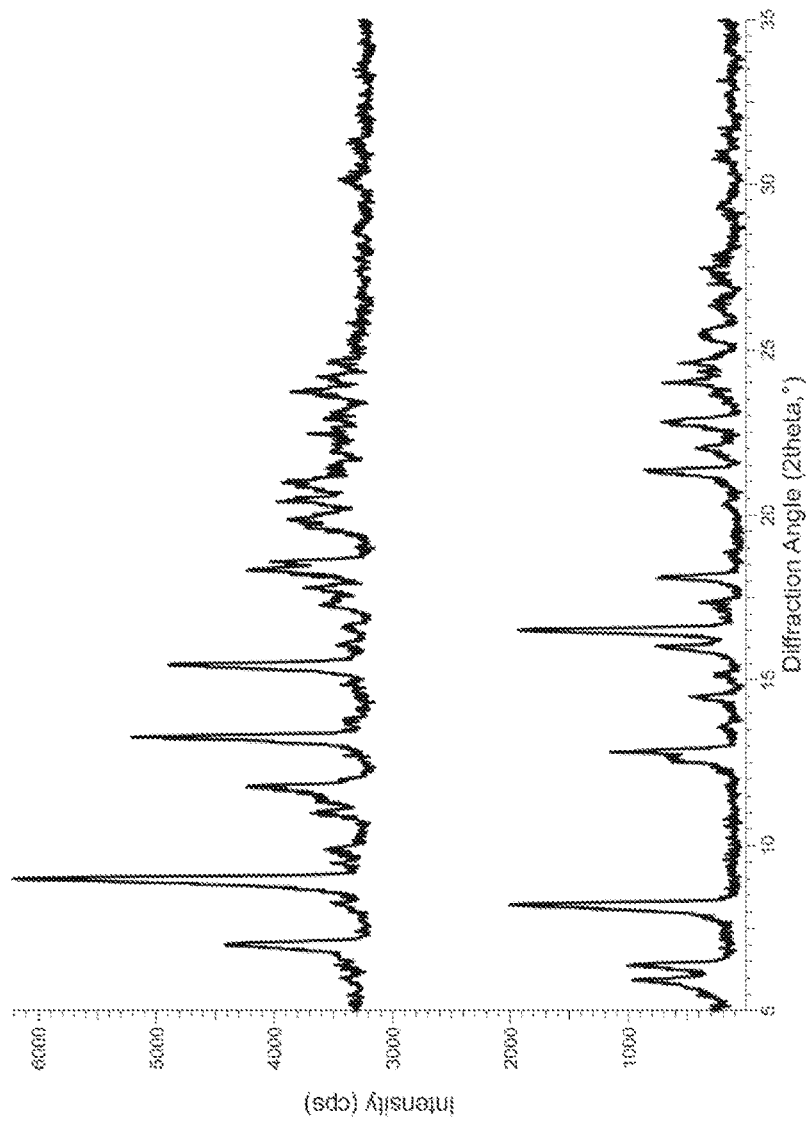
Powder X-ray diffraction patterns of the crystal (Form 1) at room temperature (the lower pattern) and above 60 °C (the upper pattern).

[Fig. 23]
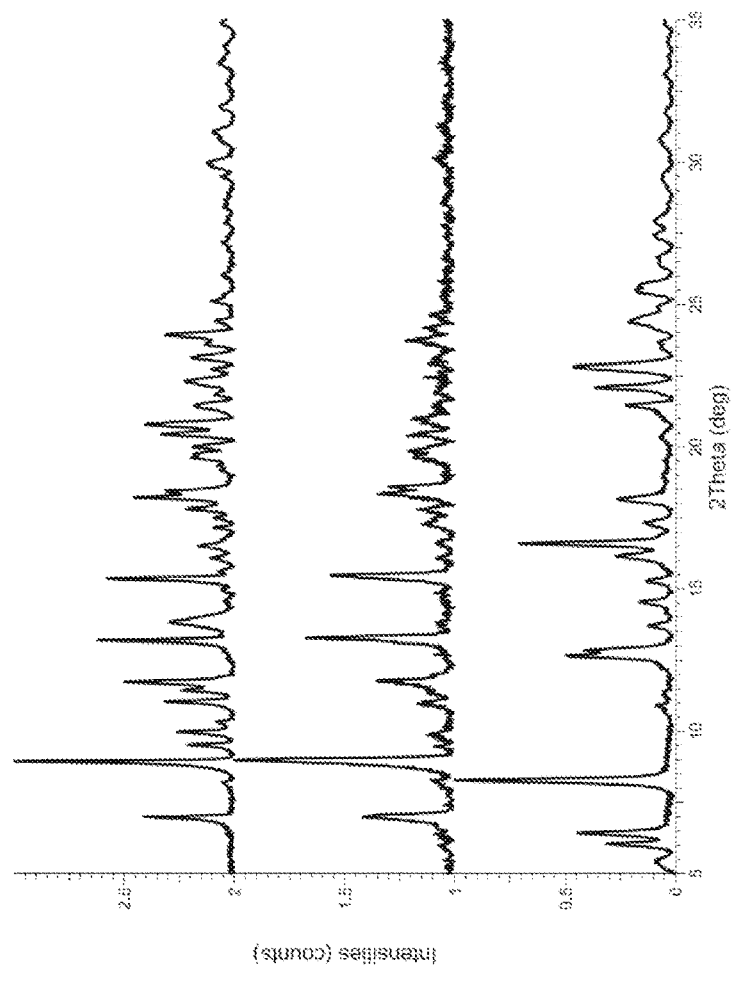
Comparison of powder X-ray diffraction patterns: 1) the crystal (Form 1) pattern analyzed by transmission method (the lower), 2) the pattern of the crystal (Form 1) sample heated above 60 °C, which is analyzed by reflection method (the middle), 3) the crystal (Form 2) pattern analyzed by transmission method (the upper).

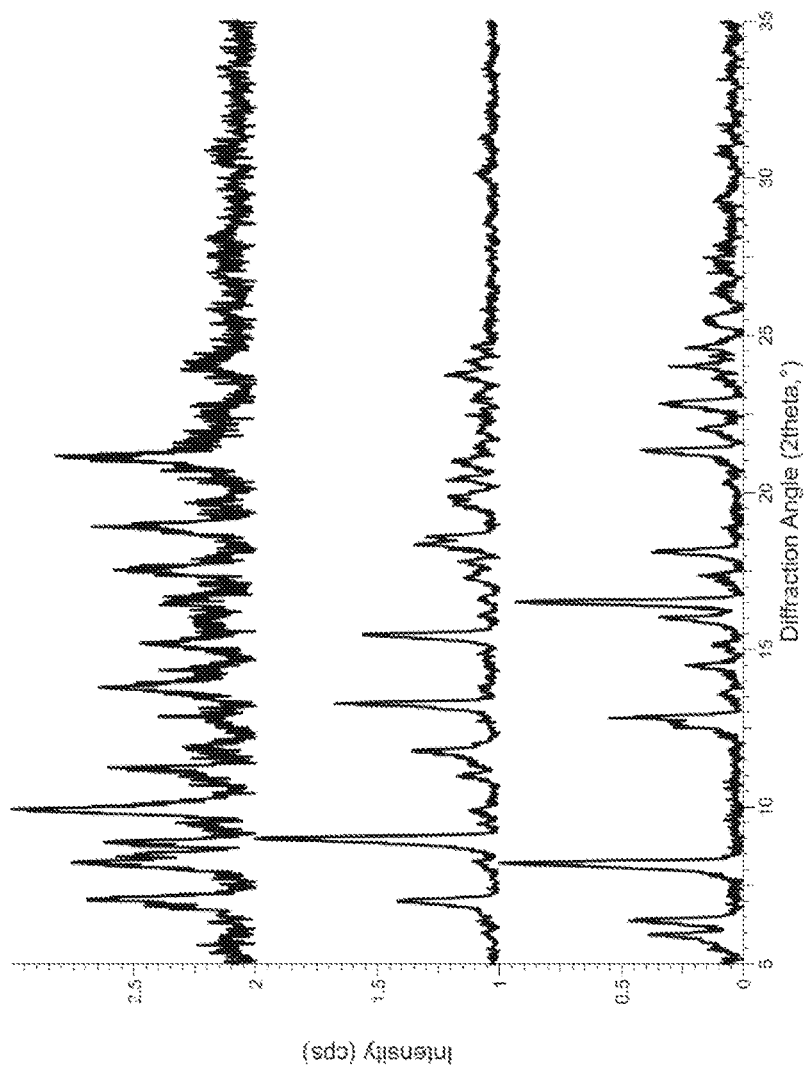
[Fig. 24] Powder X-ray diffraction patterns of the crystal (Form 1) at various temperatures: 1) room temperature (the lower pattern), 2) 61 to 71 °C (the middle pattern), 3) 125 to 134 °C (the upper pattern).

[Fig. 25]
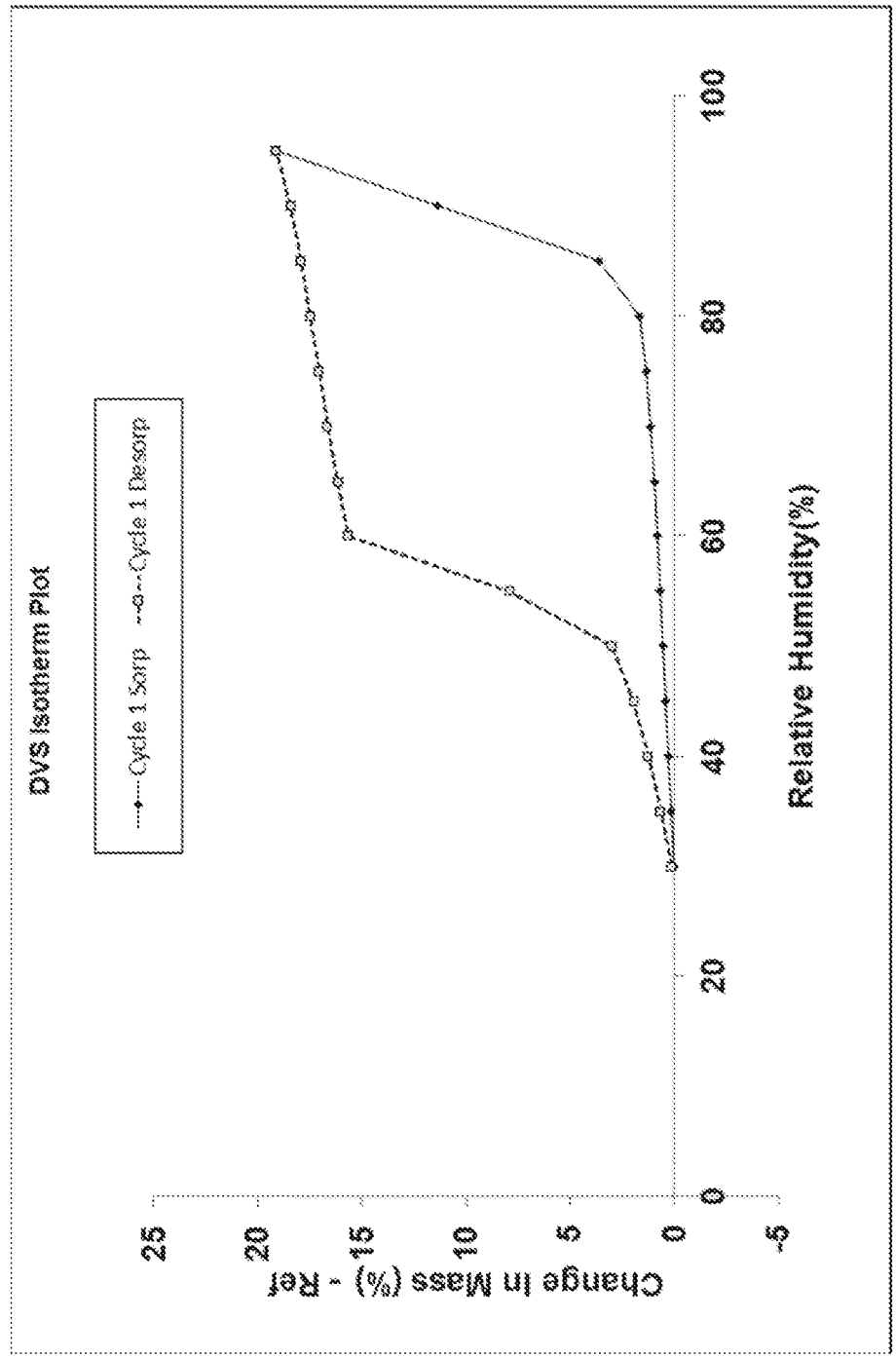

[Fig. 26]
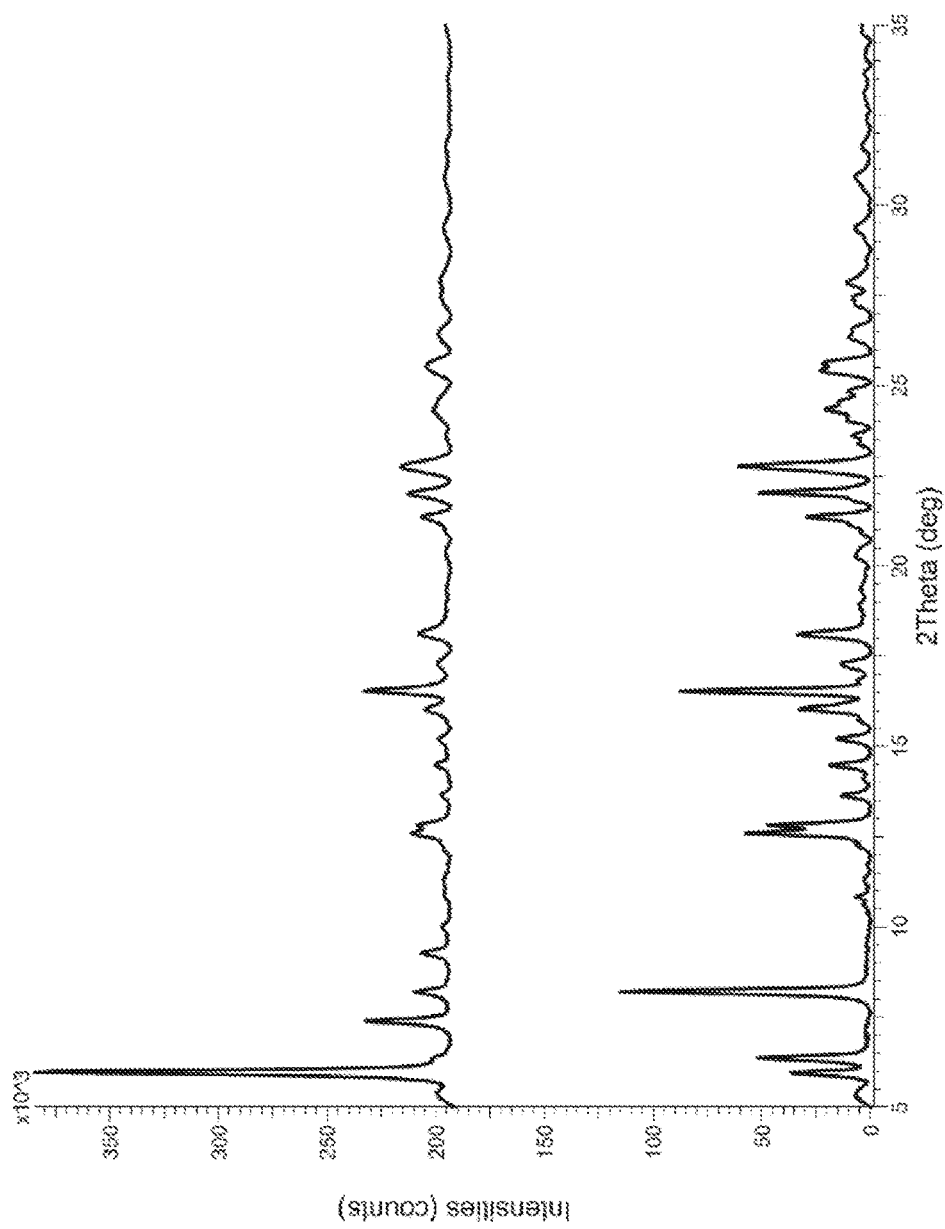

SEQUENCE LISTING

<160> NUMBER OF SEQ ID NOS: 4

<210> SEQ ID NO 1
<211> LENGTH: 1140
<212> TYPE: DNA
<213> ORGANISM: Homo sapiens

<400> SEQUENCE: 1

```
atgcccccact ccagcctgca tccatccatc ccgtgtccca ggggtcacgg ggcccagaag      60
gcagccttgg ttctgctgag tgcctgcctg gtgacccttt gggggctagg agagccacca     120
gagcacactc tccggtacct ggtgctccac ctagcctccc tgcagctggg actgctgtta     180
aacgggtct  gcagcctggc tgaggagctg cgccacatcc actccaggta ccggggcagc     240
tactggagga ctgtgcgggc ctgcctgggc tgccccctcc gcgtggggc  cctgttgctg     300
ctgtccatct atttctacta ctccctccca aatgcggtcg gcccgccctt cacttggatg     360
cttgccctcc tgggcctctc gcaggcactg aacatcctcc tgggcctcaa gggcctggcc     420
ccagctgaga tctctgcagt gtgtgaaaaa gggaatttca acgtgcccca tgggctggca     480
tggtcatatt acatcggata tctgcggctg atcctgccag agctccaggc ccggattcga     540
acttacaatc agcattacaa caacctgcta cggggtgcag tgagccagcg gctgtatatt     600
ctcctcccat ggactgtgg  ggtgcctgat aacctgagta tggctgaccc caacattcgc     660
ttcctggata aactgcccca gcagaccggt gaccgggctg gcatcaagga tcgggtttac     720
agcaacagca tctatgagct tctggagaac gggcagcggg cgggcacctg tgtcctggag     780
tacgccaccc ccttgcagac tttgtttgcc atgtcacaat acagtcaagc tggctttagc     840
cgggaggata ggcttgagca ggccaaactc ttctgccgga cacttgagga catcctggca     900
gatgcccctg agtctcagaa caactgccgc tcattgcct  accaggaacc tgcagatgac     960
agcagcttct cgctgtccca ggaggttctc cggcacctgc ggcaggagga aaaggaagag    1020
gttactgtgg gcagcttgaa gacctcagcg gtgcccagta cctccacgat gtcccaagag    1080
cctgagctcc tcatcagtgg aatggaaaag cccctccctc tccgcacgga tttctcttga    1140
```

<210> SEQ ID NO 2
<211> LENGTH: 1140

<212> TYPE: DNA
<213> ORGANISM: Homo sapiens

<400> SEQUENCE: 2

| | | | | | |
|---|---|---|---|---|---|
| atgcccact | ccagcctgca | tccatccatc | ccgtgtccca | ggggtcacgg | ggcccagaag | 60 |
| gcagccttgg | ttctgctgag | tgcctgcctg | gtgacccttt | ggggctagg | agagccacca | 120 |
| gagcacactc | tccggtacct | ggtgctccac | ctagcctccc | tgcagctggg | actgctgtta | 180 |
| aacgggtct | gcagcctggc | tgaggagctg | cgccacatcc | actccaggta | ccggggcagc | 240 |
| tactggagga | ctgtgcgggc | ctgcctgggc | tgcccctcc | gccgtggggc | cctgttgctg | 300 |
| ctgtccatct | atttctacta | ctccctccca | aatgcggtcg | gcccgccctt | cacttggatg | 360 |
| cttgccctcc | tgggcctctc | gcaggcactg | aacatcctcc | tgggcctcaa | gggcctggcc | 420 |
| ccagctgaga | tctctgcagt | gtgtgaaaaa | gggaatttca | acgtggccca | tgggctggca | 480 |
| tggtcatatt | acatcggata | tctgcggctg | atcctgccag | agctccaggc | ccggattcga | 540 |
| acttacaatc | agcattacaa | caacctgcta | cggggtgcag | tgagccagcg | gctgtatatt | 600 |
| ctcctcccat | ggactgtgg | ggtgcctgat | aacctgagta | tggctgaccc | caacattcgc | 660 |
| ttcctggata | aactgcccca | gcagaccggt | gaccatgctg | gcatcaagga | tcgggtttac | 720 |
| agcaacagca | tctatgagct | tctggagaac | gggcagcggg | cgggcacctg | tgtcctggag | 780 |
| tacgccaccc | ccttgcagac | tttgtttgcc | atgtcacaat | acagtcaagc | tggctttagc | 840 |
| cgggaggata | ggcttgagca | ggccaaactc | ttctgccgga | cacttgagga | catcctggca | 900 |
| gatgcccctg | agtctcagaa | caactgccgc | ctcattgcct | accaggaacc | tgcagatgac | 960 |
| agcagcttct | cgctgtccca | ggaggttctc | cggcacctgc | ggcaggagga | aaaggaagag | 1020 |
| gttactgtgg | gcagcttgaa | gacctcagcg | gtgcccagta | cctccacgat | gtcccaagag | 1080 |
| cctgagctcc | tcatcagtgg | aatggaaaag | cccctccctc | tccgcacgga | tttctcttga | 1140 |

<210> SEQ ID NO 3
<211> LENGTH: 1140
<212> TYPE: DNA
<213> ORGANISM: Homo sapiens

<400> SEQUENCE: 3

| | | | | | |
|---|---|---|---|---|---|
| atgcccact | ccagcctgca | tccatccatc | ccgtgtccca | ggggtcacgg | ggcccagaag | 60 |
| gcagccttgg | ttctgctgag | tgcctgcctg | gtgacccttt | ggggctagg | agagccacca | 120 |
| gagcacactc | tccggtacct | ggtgctccac | ctagcctccc | tgcagctggg | actgctgtta | 180 |
| aacgggtct | gcagcctggc | tgaggagctg | cgccacatcc | actccaggta | ccggggcagc | 240 |
| tactggagga | ctgtgcgggc | ctgcctgggc | tgcccctcc | gccgtggggc | cctgttgctg | 300 |
| ctgtccatct | atttctacta | ctccctccca | aatgcggtcg | gcccgccctt | cacttggatg | 360 |
| cttgccctcc | tgggcctctc | gcaggcactg | aacatcctcc | tgggcctcaa | gggcctggcc | 420 |
| ccagctgaga | tctctgcagt | gtgtgaaaaa | gggaatttca | acgtggccca | tgggctggca | 480 |
| tggtcatatt | acatcggata | tctgcggctg | atcctgccag | agctccaggc | ccggattcga | 540 |

```
acttacaatc agcattacaa caacctgcta cggggtgcag tgagccagcg gctgtatatt      600
ctcctcccat tggactgtgg ggtgcctgat aacctgagta tggctgaccc caacattcgc      660
ttcctggata aactgcccca gcagaccgct gaccgagctg gcatcaagga tcgggtttac      720
agcaacagca tctatgagct ctggagaaac gggcagcggg cgggcacctg tgtcctggag      780
tacgccaccc ccttgcagac tttgtttgcc atgtcacaat acagtcaagc tggctttagc      840
cgggaggata ggcttgagca ggccaaactc ttctgccaga cacttgagga catcctggca      900
gatgcccctg agtctcagaa caactgccgc ctcattgcct accaggaacc tgcagatgac      960
agcagcttct cgctgtccca ggaggttctc cggcacctgc ggcaggagga aaaggaagag      1020
gttactgtgg gcagcttgaa gacctcagcg gtgcccagta cctccacgat gtcccaagag      1080
cctgagctcc tcatcagtgg aatggaaaag cccctccctc tccgcacgga tttctcttga     1140
```

<210> SEQ ID NO 4
<211> LENGTH: 187
<212> TYPE: PRT
<213> ORGANISM: Escherichia coli

<400> SEQUENCE: 4

```
Val Ala His Gly Leu Ala Trp Ser Tyr Tyr Ile Gly Tyr Leu Arg Leu
1               5                   10                  15

Ile Leu Pro Glu Leu Gln Ala Arg Ile Arg Thr Tyr Asn Gln His Tyr
            20                  25                  30

Asn Asn Leu Leu Arg Gly Ala Val Ser Gln Arg Leu Tyr Ile Leu Leu
        35                  40                  45

Pro Leu Asp Cys Gly Val Pro Asp Asn Leu Ser Met Ala Asp Pro Asn
    50                  55                  60

Ile Arg Phe Leu Asp Lys Leu Pro Gln Gln Thr Gly Asp Arg Ala Gly
65                  70                  75                  80

Ile Lys Asp Arg Val Tyr Ser Asn Ser Ile Tyr Glu Leu Leu Glu Asn
                85                  90                  95

Gly Gln Arg Ala Gly Thr Cys Val Leu Glu Tyr Ala Thr Pro Leu Gln
            100                 105                 110

Thr Leu Phe Ala Met Ser Gln Tyr Ser Gln Ala Gly Phe Ser Arg Glu
        115                 120                 125

Asp Arg Leu Glu Gln Ala Lys Leu Phe Cys Arg Thr Leu Glu Asp Ile
    130                 135                 140

Leu Ala Asp Ala Pro Glu Ser Gln Asn Asn Cys Arg Leu Ile Ala Tyr
145                 150                 155                 160

Gln Glu Pro Ala Asp Asp Ser Ser Phe Ser Leu Ser Gln Glu Val Leu
                165                 170                 175

Arg His Leu Arg Gln Glu Glu Lys Glu Glu Val
            180                 185
```

SALTS OF COMPOUNDS AND CRYSTALS THEREOF

CROSS REFERENCE TO RELATED APPLICATIONS

This application is the United States national phase of International Application No. PCT/JP2019/031951, filed on Aug. 14, 2019, which claims the benefit of U.S. Provisional Patent Application Ser. No. 62/764,774, filed on Aug. 16, 2018.

REFERENCE TO A SEQUENCE LISTING SUBMITTED VIA EFS-WEB

The content of the ASCII text file of the sequence listing named "0099020-000003_ST25.txt", which is 6,570 bytes in size, was created on Jan. 30, 2023 and electronically submitted herewith via EFS-Web, and is hereby incorporated by reference in its entirety.

TECHNICAL FIELD

The present invention relates to salts of compounds and crystals thereof.

BACKGROUND ART

STING (stimulator of interferon genes) is a signaling molecule in the innate response to dsDNA in the cytosol. STING deletion has been reported in multiple human cancers. In addition, deregulation of STING signaling in human cancers also has been reported in melanoma (Xia T, et al., "Recurrent Loss of STING Signaling in Melanoma Correlates with Susceptibility to Viral Oncolysis" Cancer Res. 2016) and colon cancer. (Xia T, et al., "Deregulation of STING Signaling in Colorectal Carcinoma Constrains DNA Damage Responses and Correlates With Tumorigenesis" Cell Rep. 2016; 14:282-97). Interestingly, in those studies, genomic analysis results showed loss expression of STING is not due to gene deletion or mutation, but through epigenetic changes. (Xia, Cancer Res. 2016; Xia, Cell Rep. 2016). STING's cancer protection activity is also supported by evidence obtained from mouse model studies. STING knockout mice have shown defective tumor control. (Woo S R, et al. "STING-dependent cytosolic DNA sensing mediates innate immune recognition of immunogenic tumors" Immunity 2014; 41:830-42).

In addition, STING's role in protecting ontogenesis has been demonstrated in several mouse spontaneous models, including glioma (Ohkuri T, et al., "Protective role of STING against gliomagenesis: Rational use of STING agonist in anti-glioma immunotherapy" Oncoimmunology. 2015; 4:e999523), and colon cancer (Zhu Q, et al., "Cutting edge: STING mediates protection against colorectal tumorigenesis by governing the magnitude of intestinal inflammation" J. Immunol. 2014; 193:4779-82). This anti-tumor effect may be due to its ability to counter over-activation of NF-kB and STAT3. (Ohkuri 2015). Activation of STING pathway also showed potent activity in preclinical mouse tumor models. (Woo 2014; Chandra D, et al. "STING ligand c-di-GMP improves cancer vaccination against metastatic breast cancer" Cancer Immunol Res. 2014; 2:901-10; Corrales L, et al., "Direct Activation of STING in the Tumor Microenvironment Leads to Potent and Systemic Tumor Regression and Immunity" Cell Rep. 2015; 11:1018-30; Curran E, et al. "STING Pathway Activation Stimulates Potent Immunity against Acute Myeloid Leukemia" Cell Rep. 2016; 15:2357-66; Tang C H, et al. "Agonist-Mediated Activation of STING Induces Apoptosis in Malignant B Cells" Cancer Res. 2016; 76:2137-52). This anti-tumor activity is likely due to disruption of tumor vasculature and followed by induction of adaptive immune response. (Corrales L, et al., "The host STING pathway at the interface of cancer and immunity" J. Clin. Invest. 2016; 126:2404-11). Accordingly, direct stimulation of STING in a tumor microenvironment by an agonist may represent a novel approach for treating multiple cancer types.

SUMMARY OF INVENTION

Technical Problem

A compound represented by the formula (I), namely, (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (hereafter referred to as Compound (I)), suppresses the growth of tumors.

[Chem.1]

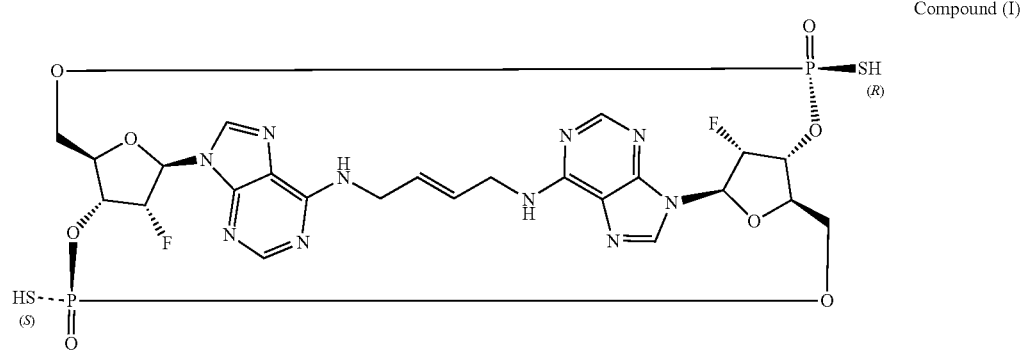

Compound (I)

Generally, the physical properties of a compound, salts thereof, and their crystals used as a pharmaceutical product largely influence on the bioavailability of a drug, the purity of an active pharmaceutical ingredient, prescription of a preparation and the like. An object of the present invention is therefore to provide salts of Compound (I) or crystals thereof with a potential to be used as drug substance in pharmaceuticals.

Solution to Problem

The present inventor has found salts of Compound (I) or crystals thereof with a potential to be used as drug substance in pharmaceuticals, thereby completing the invention.

Specifically, the present invention provides the following <1> to <50>.

<1> A crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) ammonium salt, Compound (I) sodium salt, or Compound (I).

[Chem.2]

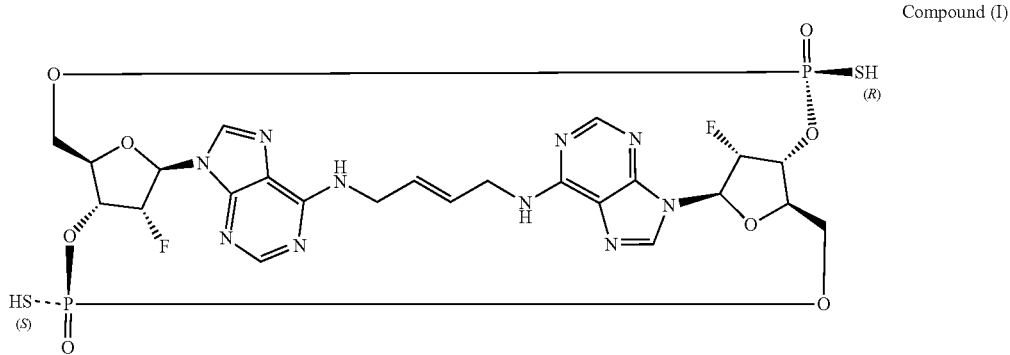

Compound (I)

<2> The crystal according to <1>, which is a crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) ammonium salt.
<3> The crystal according to <2>, which is a crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) di-ammonium salt.
<4> The crystal (Form 1) according to <3>, having a diffraction peak at a diffraction angle (2θ±0.2°) of 8.3 in a powder X-ray diffraction.
<5> The crystal (Form 1) according to <4>, having diffraction peaks at diffraction angles (2θ±0.2°) of 6.4°, 8.3° and 16.6° in a powder X-ray diffraction.
<6> The crystal (Form 1) according to <4>, having diffraction peaks at diffraction angles (2θ±0.2°) of 6.4°, 8.3°, 12.7°, 16.6° and 25.4° in a powder X-ray diffraction.
<7> The crystal (Form 1) according to <4>, having diffraction peaks at diffraction angles (2θ±0.2°) of 6.4°, 8.3°, 12.7°, 14.6°, 16.6°, 18.1°, 22.1°, 22.8°, 24.4° and 25.4° in a powder X-ray diffraction.
<8> The crystal (Form 1) according to <7>, having a powder X-ray diffraction pattern substantially the same as the powder X-ray diffraction pattern shown in FIG. 3.

<9> The crystal (Form 1) according to any one of <4> to <8>, which is a hydrate.
<10> The crystal (Form 2) according to <3>, having a diffraction peak at a diffraction angle (2θ±0.2°) of 9.0° in a powder X-ray diffraction.
<11> The crystal (Form 2) according to <10>, having diffraction peaks at diffraction angles (2θ±0.2°) of 9.0°, 15.4° and 20.8° in a powder X-ray diffraction.
<12> The crystal (Form 2) according to <10>, having diffraction peaks at diffraction angles (2θ±0.2°) of 9.0°, 15.4°, 20.8°, 24.0° and 30.0° in a powder X-ray diffraction.
<13> The crystal (Form 2) according to <10>, having diffraction peaks at diffraction angles (2θ±0.2°) of 7.0°, 9.0°, 11.8°, 13.2°, 15.4°, 19.7°, 20.8°, 24.0°, 30.0° and 31.1° in a powder X-ray diffraction.
<14> The crystal (Form 2) according to <13>, having a powder X-ray diffraction pattern substantially the same as the powder X-ray diffraction pattern shown in FIG. 4.
<15> The crystal (Form 2) according to any one of <10> to <14>, which is a hydrate.
<16> The crystal (Form 3) according to <3>, having a diffraction peak at a diffraction angle (2θ±0.2°) of 7.4° in a powder X-ray diffraction.
<17> The crystal (Form 3) according to <16>, having diffraction peaks at diffraction angles (2θ±0.2°) of 7.4°, 16.0° and 21.4° in a powder X-ray diffraction.
<18> The crystal (Form 3) according to <16>, having diffraction peaks at diffraction angles (2θ±0.2°) of 6.0°, 7.4°, 9.3°, 16.0° and 21.4° in a powder X-ray diffraction.
<19> The crystal (Form 3) according to <16>, having diffraction peaks at diffraction angles (2θ±0.2°) of 6.0°, 7.4°, 9.3°, 12.6°, 16.0°, 16.6°, 18.1, 21.4°, 22.00 and 22.8° in a powder X-ray diffraction.
<20> The crystal (Form 3) according to <19>, having a powder X-ray diffraction pattern substantially the same as the powder X-ray diffraction pattern shown in FIG. 5.
<21> The crystal (Form 3) according to any one of <16> to <20>, which is a hydrate.
<22> The crystal (Form 4) according to <3>, having a diffraction peak at a diffraction angle (2θ±0.2°) of 9.7° in a powder X-ray diffraction.
<23> The crystal (Form 4) according to <22>, having diffraction peaks at diffraction angles (2θ±0.2°) of 9.7°, 14.0° and 26.9° in a powder X-ray diffraction.
<24> The crystal (Form 4) according to <22>, having diffraction peaks at diffraction angles (2θ±0.2°) of 9.7°, 14.0°, 17.4°, 22.3° and 26.9° in a powder X-ray diffraction.

<25> The crystal (Form 4) according to <22>, having diffraction peaks at diffraction angles (2θ±0.2°) of 5.9°, 7.6°, 9.7°, 11.6°, 14.0°, 16.0°, 17.4°, 22.3°, 24.6° and 26.9° in a powder X-ray diffraction.

<26> The crystal (Form 4) according to <25>, having a powder X-ray diffraction pattern substantially the same as the powder X-ray diffraction pattern shown in FIG. 6.

<27> The crystal (Form 5) according to <3>, having a diffraction peak at a diffraction angle (2θ±0.2°) of 20.0° in a powder X-ray diffraction.

<28> The crystal (Form 5) according to <27>, having diffraction peaks at diffraction angles (2θ±0.2°) of 10.9°, 20.0° and 23.6° in a powder X-ray diffraction.

<29> The crystal (Form 5) according to <27>, having diffraction peaks at diffraction angles (2θ±0.2°) of 10.9°, 17.7°, 18.9°, 20.0° and 23.6° in a powder X-ray diffraction.

<30> The crystal (Form 5) according to <27>, having diffraction peaks at diffraction angles (2θ±0.2°) of 9.0°, 9.6°, 10.9°, 13.0°, 15.3°, 17.7°, 18.9°, 20.0°, 21.5° and 23.6° in a powder X-ray diffraction.

<31> The crystal (Form 5) according to <30>, having a powder X-ray diffraction pattern substantially the same as the powder X-ray diffraction pattern shown in FIG. 7.

<32> The crystal according to <2>, which is a crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaocta-cyclo[28.6.4.1$^{3,36}$.1$^{28,31}$.0$^{4,8}$.0$^{7,12}$.0$^{19,24}$.0$^{23,27}$] dotetraconta-5,7,9,11,15,19,21,23,25-nonaene-34,39-dione (Compound (I)) mono-ammonium salt.

<33> The crystal (Form 6) according to <32>, having a diffraction peak at a diffraction angle (2θ±0.2°) of 17.0° in a powder X-ray diffraction.

<34> The crystal (Form 6) according to <33>, having diffraction peaks at diffraction angles (2θ±0.2°) of 17.0°, 21.6° and 25.9° in a powder X-ray diffraction.

<35> The crystal (Form 6) according to <33>, having diffraction peaks at diffraction angles (2θ±0.2°) of 15.10, 16.4°, 17.0°, 21.6° and 25.9° in a powder X-ray diffraction.

<36> The crystal (Form 6) according to <33>, having diffraction peaks at diffraction angles (2θ±0.2°) of 6.9°, 8.5°, 12.0°, 15.1°, 16.4°, 17.0°, 21.0°, 21.6°, 22.8° and 25.9° in a powder X-ray diffraction.

<37> The crystal (Form 6) according to <36>, having a powder X-ray diffraction pattern substantially the same as the powder X-ray diffraction pattern shown in FIG. 8.

<38> The crystal according to <1>, which is a crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaocta-cyclo[28.6.4.1$^{3,36}$.1$^{28,31}$.0$^{4,8}$.0$^{7,12}$.0$^{19,24}$.0$^{23,27}$] dotetraconta-5,7,9,11,15,19,21,23,25-nonaene-34,39-dione (Compound (I)) sodium salt.

<39> The crystal according to <38>, having a diffraction peak at a diffraction angle (2θ±0.2°) of 6.1° in a powder X-ray diffraction.

<40> The crystal according to <39>, having diffraction peaks at diffraction angles (2θ±0.2°) of 6.10, 9.3° and 16.6° in a powder X-ray diffraction.

<41> The crystal according to <39>, having diffraction peaks at diffraction angles (2θ±0.2°) of 6.10, 9.3°, 15.9°, 16.6° and 22.3° in a powder X-ray diffraction.

<42> The crystal according to <39>, having diffraction peaks at diffraction angles (2θ±0.2°) of 6.1, 9.3°, 13.4°, 14.8°, 15.9°, 16.6°, 20.6°, 22.3°, 23.5° and 24.4° in a powder X-ray diffraction.

<43> The crystal according to <42>, having a powder X-ray diffraction pattern substantially the same as the powder X-ray diffraction pattern shown in FIG. 9.

<44> The crystal according to <1>, which is a crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaocta-cyclo[28.6.4.1$^{3,36}$.1$^{28,31}$.0$^{4,8}$.0$^{7,12}$.0$^{19,24}$.0$^{23,27}$] dotetraconta-5,7,9,11,15,19,21,23,25-nonaene-34,39-dione (Compound (I)).

<45> The crystal according to <44>, having a diffraction peak at a diffraction angle (2θ±0.2°) of 5.6° in a powder X-ray diffraction.

<46> The crystal according to <45>, having diffraction peaks at diffraction angles (2θ±0.2°) of 5.6°,13.9° and 16.8° in a powder X-ray diffraction.

<47> The crystal according to <45>, having diffraction peaks at diffraction angles (2θ±0.2°) of 5.6°, 8.9°, 11.4°, 13.9° and 16.8° in a powder X-ray diffraction.

<48> The crystal according to <45>, having diffraction peaks at diffraction angles (2θ±0.2°) of 5.6°, 7.9°, 8.9°, 11.4°, 13.9°, 16.8°, 22.1° and 23.1° in a powder X-ray diffraction.

<49> The crystal according to <48>, having a powder X-ray diffraction pattern substantially the same as the powder X-ray diffraction pattern shown in FIG. 10.

<50> A pharmaceutical composition comprising the crystal according to any one of <1> to <49>.

Advantageous Effects of Invention

The salts of Compound (I) and the crystals thereof provided by the present invention possess properties such as hygroscopicity as shown in the examples described in later and a potential to be used as drug substance in pharmaceuticals.

BRIEF DESCRIPTION OF DRAWINGS

FIG. 1 shows an $^1$H NMR spectrograph for Compound (I) ammonium salt.

FIG. 2A shows X-ray crystallography result (ORTEP drawings) for a crystal of Compound (I) ammonium salt, where two molecules are present in the asymmetric crystal unit.

FIG. 2B shows X-ray crystallography result (ORTEP drawings) for a first molecule in the asymmetric crystal unit.

FIG. 2C shows X-ray crystallography result (ORTEP drawings) for a second molecule in the asymmetric crystal unit.

FIG. 3 shows a powder X-ray diffraction pattern of the crystal (Form 1) of the Compound (I) di-ammonium salt obtained in Example 1. The abscissa shows the diffraction angle (2θ) and the ordinate shows the peak intensity.

FIG. 4 shows a powder X-ray diffraction pattern of the crystal (Form 2) of the Compound (I) di-ammonium salt obtained in Example 2. The abscissa shows the diffraction angle (2θ) and the ordinate shows the peak intensity.

FIG. 5 shows a powder X-ray diffraction pattern of the crystal (Form 3) of the Compound (I) di-ammonium salt obtained in Example 3. The abscissa shows the diffraction angle (2θ) and the ordinate shows the peak intensity.

FIG. 6 shows a powder X-ray diffraction pattern of the crystal (Form 4) of the Compound (I) di-ammonium salt obtained in Example 4. The abscissa shows the diffraction angle (2θ) and the ordinate shows the peak intensity.

FIG. 7 shows a powder X-ray diffraction pattern of the crystal (Form 5) of the Compound (I) di-ammonium salt obtained in Example 5. The abscissa shows the diffraction angle (2θ) and the ordinate shows the peak intensity.

FIG. 8 shows a powder X-ray diffraction pattern of the crystal (Form 6) of the Compound (I) mono-ammonium salt obtained in Example 6. The abscissa shows the diffraction angle (2θ) and the ordinate shows the peak intensity.

FIG. 9 shows a powder X-ray diffraction pattern of the crystal of the Compound (I) sodium salt obtained in Example 7. The abscissa shows the diffraction angle (2θ) and the ordinate shows the peak intensity.

FIG. 10 shows a powder X-ray diffraction pattern of the crystal of the Compound (I) obtained in Example 8. The abscissa shows the diffraction angle (2θ) and the ordinate shows the peak intensity.

FIG. 11 is a graph showing hygroscopicity of the crystal (Form 1) of the Compound (I) di-ammonium salt obtained in Example 1. The abscissa shows the relative humidity and the ordinate shows the weight change.

FIG. 12 is a graph showing hygroscopicity of the crystal (Form 2) of the Compound (I) di-ammonium salt obtained in Example 2. The abscissa shows the relative humidity and the ordinate shows the weight change.

FIG. 13 is a graph showing hygroscopicity of the crystal (Form 5) of the Compound (I) di-ammonium salt obtained in Example 5. The abscissa shows the relative humidity and the ordinate shows the weight change.

FIG. 14 is a graph showing hygroscopicity of the crystal (Form 6) of the Compound (I) mono-ammonium salt obtained in Example 6. The abscissa shows the relative humidity and the ordinate shows the weight change.

FIG. 15 is a graph showing hygroscopicity of the crystal of the Compound (I) sodium salt obtained in Example 7. The abscissa shows the relative humidity and the ordinate shows the weight change.

FIG. 16 shows an expression vector map for WY STING (pLenti-WT human STING-Puro).

FIG. 17 accompanies Pharmacological Test Example 6 and show curative activity of Compound (I) di-ammonium salt in a CT26 dual tumor model.

FIG. 18 accompanies Pharmacological Test Example 6 and show curative activity of Compound (I) di-ammonium salt in a CT26 dual tumor model.

FIG. 19 accompanies Pharmacological Test Example 7 and shows a tumor volume plot for treated tumors and survival curve.

FIG. 20 accompanies Pharmacological Test Example 8 and shows a tumor volume plot for treated tumors and survival curve.

FIG. 21 shows a TG-DTA thermogram of the crystal (Form 1).

FIG. 22 shows powder X-ray diffraction patterns of the crystal (Form 1) at room temperature (the lower pattern) and above 60° C. (the upper pattern).

FIG. 23 shows comparison of powder X-ray diffraction patterns: 1) the crystal (Form 1) pattern analyzed by transmission method (the lower), 2) the pattern of the crystal (Form 1) sample heated above 60° C., which is analyzed by reflection method (the middle), 3) the crystal (Form 2) pattern analyzed by transmission method (the upper).

FIG. 24 shows powder X-ray diffraction patterns of the crystal (Form 1) at various temperatures: 1) room temperature (the lower pattern), 2) 61 to 71° C. (the middle pattern), 3) 125 to 134° C. (the upper pattern).

FIG. 25 shows adsorption and desorption isotherm of Form 1 at 25° C.

FIG. 26 shows comparison of the PXRD patterns of Form 1 between before (the lower pattern) and after storage at 25° C. and 94% RH for 4 days (the upper pattern).

DESCRIPTION OF EMBODIMENTS

A salt of the Compound (I) of the present invention, a crystal thereof, and production methods thereof will be described in detail.

As used herein, a "salt" refers to a chemical entity made up of the Compound (I) as the acidic component and a specific number of equivalents of a base to the Compound (I). Here, the term "a salt of (1R,3R,15E,28R,29R,30R,31R, 34R,36R,39S,41R)-29,41-Difluoro-34,39-bis(sulfanyl)-2, 33,35,38,40,42-hexaoxa-4,6,9,11,13,18,20,22,25,27-decaaza-34$\lambda^5$,39$\lambda^5$-diphosphaoctacyclo[28.6.4.1$^{3.36}$.1$^{28.31}$.0$^4$, 8.0$^{7.12}$.0$^{19.24}$.0$^{23.27}$]dotetraconta-5,7,9,11,15,19,21,23,25-nonaene-34,39-dione (Compound (I)) represented by the formula (I), and a base selected from the group consisting of sodium hydroxide, sodium carbonate, ammonia in ethanol and ammonium hydroxide etc."is used for the same meaning as" a salt of (1R,3R,15E,28R,29R,30R,31R,34R,36R,39S, 41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3.36}$.1$^{28.31}$.0$^{4,8}$.0$^{7,12}$.0$^{19.24}$.0$^{23.27}$] dotetraconta-5,7,9,11,15,19,21,23,25-nonaene-34,39-dione (Compound (I)) represented by the formula (I) formed with a base selected from the group consisting of sodium hydroxide, sodium carbonate, ammonia in ethanol and ammonium hydroxide etc."

Examples of a "salt" used herein include salts with inorganic bases, and in particular, pharmaceutically acceptable salts are preferred.

A salt of the Compound (I) may also be a solvate or a hydrate. As used herein, a solvate or a hydrate of the salt of Compound (I) means a solid formed from the salt of the Compound (I) together with solvent molecules or water molecule. Examples of the solvent in the solvate include: a ketone solvent such as acetone, methyl ethyl ketone or cyclohexanone; an ester solvent such as ethyl acetate or methyl acetate; an ether solvent such as 1,2-dimethoxyethane or methyl-tert-butyl ether; an alcohol solvent such as methanol, ethanol, 1-propanol or isopropanol; a polar solvent such as N-methyl-2-pyrrolidone, N,N-dimethylformamide or dimethyl sulfoxide.

As used herein, a "crystal" refers to a crystal of the salt of Compound (I) or a crystal of the Compound (I). Accordingly, a crystal of Compound (I) ammonium salt, for example, means a crystal of the salt formed between Compound (I) and ammonia (or ammonium hydroxide). In addition, a crystal of Compound (I) di-ammonium salt, for example, means a crystal of the salt formed between one molecule of Compound (I) and two molecules of ammonia (or ammonium hydroxide).

Examples of crystals preferred herein include:

(a1) a crystal (Form 1) of Compound (I) di-ammonium salt, having a diffraction peak at a diffraction angle (2θ±0.2°) of 8.3° in a powder X-ray diffraction;

(a2) a crystal (Form 1) of Compound (I) di-ammonium salt, having diffraction peaks at diffraction angles (2θ±0.2°) of 8.30 and 16.6° in a powder X-ray diffraction;

(a3) a crystal (Form 1) of Compound (I) di-ammonium salt, having diffraction peaks at diffraction angles (2θ±0.2°) of 6.4°, 8.3° and 16.6° in a powder X-ray diffraction;

(a4) a crystal (Form 1) of Compound (I) di-ammonium salt, having diffraction peaks at diffraction angles (2θ±0.2°) of 6.4°, 8.3°, 12.7°, 16.6° and 25.4° in a powder X-ray diffraction;

(a5) a crystal (Form 1) of Compound (I) di-ammonium salt, having diffraction peaks at diffraction angles (2θ±0.2°) of 6.4°, 8.3°, 12.7°, 16.6°, 22.1, 22.8° and 25.4° in a powder X-ray diffraction;

(a6) a crystal (Form 1) of Compound (I) di-ammonium salt, having diffraction peaks at diffraction angles (2θ±0.2°) of 6.4°, 8.3°, 12.7°, 14.6°, 16.6°, 18.1, 22.1, 22.8°, 24.4° and 25.4° in a powder X-ray diffraction;

(b1) a crystal (Form 2) of Compound (I) di-ammonium salt, having a diffraction peaks at a diffraction angle (2θ±0.2°) of 9.0° in a powder X-ray diffraction;

(b2) a crystal (Form 2) of Compound (I) di-ammonium salt, having diffraction peaks at diffraction angles (2θ±0.2°) of 9.0° and 15.4° in a powder X-ray diffraction;

(b3) a crystal (Form 2) of Compound (I) di-ammonium salt, having diffraction peaks at diffraction angles (2θ±0.2°) of 9.0°, 15.4° and 20.8° in a powder X-ray diffraction;

(b4) a crystal (Form 2) of Compound (I) di-ammonium salt, having diffraction peaks at diffraction angles (2θ±0.2°) of 9.0°, 15.4°, 20.8°, 24.0° and 30.0° in a powder X-ray diffraction;

(b5) a crystal (Form 2) of Compound (I) di-ammonium salt, having diffraction peaks at diffraction angles (2θ±0.2°) of 9.0°, 11.8°, 15.4°, 20.8°, 24.0°, 30.0° and 31.1° in a powder X-ray diffraction;

(b6) a crystal (Form 2) of Compound (I) di-ammonium salt, having diffraction peaks at diffraction angles (2θ±0.2°) of 7.0°, 9.0°, 11.8°, 13.2°, 15.4°, 19.7°, 20.8°, 24.0°, 30.0° and 31.1° in a powder X-ray diffraction;

(c1) a crystal (Form 3) of Compound (I) di-ammonium salt, having a diffraction peak at a diffraction angle (2θ±0.2°) of 7.4° in a powder X-ray diffraction;

(c2) a crystal (Form 3) of Compound (I) di-ammonium salt, having diffraction peaks at diffraction angles (2θ±0.2°) of 7.4° and 16.0° in a powder X-ray diffraction;

(c3) a crystal (Form 3) of Compound (I) di-ammonium salt, having diffraction peaks at diffraction angles (2θ±0.2°) of 7.4°, 16.0° and 21.4° in a powder X-ray diffraction;

(c4) a crystal (Form 3) of Compound (I) di-ammonium salt, having diffraction peaks at diffraction angles (2θ±0.2°) of 6.0°, 7.4°, 9.3°, 16.0° and 21.4° in a powder X-ray diffraction;

(c5) a crystal (Form 3) of Compound (I) di-ammonium salt, having diffraction peaks at diffraction angles (2θ±0.2°) of 6.0°, 7.4°, 9.3°, 12.6°, 16.0°, 16.6° and 21.4° in a powder X-ray diffraction;

(c6) a crystal (Form 3) of Compound (I) di-ammonium salt, having diffraction peaks at diffraction angles (2θ±0.2°) of 6.0°, 7.4°, 9.3°, 12.6°, 16.0°, 16.6°, 18.10, 21.4°, 22.0° and 22.8° in a powder X-ray diffraction;

(d1) a crystal (Form 4) of Compound (I) di-ammonium salt, having a diffraction peak at a diffraction angle (2θ±0.2°) of 9.7° in a powder X-ray diffraction;

(d2) a crystal (Form 4) of Compound (I) di-ammonium salt, having diffraction peaks at diffraction angles (2θ±0.2°) of 9.7° and 14.0° in a powder X-ray diffraction;

(d3) a crystal (Form 4) of Compound (I) di-ammonium salt, having diffraction peaks at diffraction angles (2θ±0.2°) of 9.7°, 14.0° and 26.9° in a powder X-ray diffraction;

(d4) a crystal (Form 4) of Compound (I) di-ammonium salt, having diffraction peaks at diffraction angles (2θ±0.2°) of 9.7°, 14.0°, 17.4°, 22.3° and 26.9° in a powder X-ray diffraction;

(d5) a crystal (Form 4) of Compound (I) di-ammonium salt, having diffraction peaks at diffraction angles (2θ±0.2° of 7.6°, 9.7°, 14.0°, 17.4°, 22.3°, 24.6° and 26.9° in a powder X-ray diffraction;

(d6) a crystal (Form 4) of Compound (I) di-ammonium salt, having diffraction peaks at diffraction angles (2θ±0.2°) of 5.9°, 7.6°, 9.7°, 11.6°, 14.0°, 16.0°, 17.4°, 22.3°, 24.6° and 26.9° in a powder X-ray diffraction;

(e1) a crystal (Form 5) of Compound (I) di-ammonium salt, having a diffraction peaks at a diffraction angle (2θ±0.2°) of 20.0° in a powder X-ray diffraction;

(e2) a crystal (Form 5) of Compound (I) di-ammonium salt, having diffraction peaks at diffraction angles (2θ±0.2°) of 20.0° and 23.6° in a powder X-ray diffraction;

(e3) a crystal (Form 5) of Compound (I) di-ammonium salt, having diffraction peaks at diffraction angles (2θ±0.2°) of 10.9°, 20.0° and 23.6° in a powder X-ray diffraction;

(e4) a crystal (Form 5) of Compound (I) di-ammonium salt, having diffraction peaks at diffraction angles (2θ±0.2°) of 10.9°, 17.7°, 18.9°, 20.0° and 23.6° in a powder X-ray diffraction;

(e5) a crystal (Form 5) of Compound (I) di-ammonium salt, having diffraction peaks at diffraction angles (2θ±0.2°) of 10.9°, 13.0°, 17.7°, 18.9°, 20.0°, 21.5° and 23.6° in a powder X-ray diffraction;

(e6) a crystal (Form 5) of Compound (I) di-ammonium salt, having diffraction peaks at diffraction angles (2θ±0.2°) of 9.0°, 9.6°, 10.9°, 13.0°, 15.3°, 17.7°, 18.9°, 20.0°, 21.5° and 23.6° in a powder X-ray diffraction;

(f1) a crystal (Form 6) of Compound (I) mono-ammonium salt, having a diffraction peak at a diffraction angle (2θ±0.2°) of 17.0° in a powder X-ray diffraction;

(f2) a crystal (Form 6) of Compound (I) mono-ammonium salt, having diffraction peaks at diffraction angles (2θ±0.2°) of 17.0° and 25.9° in a powder X-ray diffraction;

(f3) a crystal (Form 6) of Compound (I) mono-ammonium salt, having diffraction peaks at diffraction angles (2θ±0.2°) of 17.0°, 21.6° and 25.9° in a powder X-ray diffraction;

(f4) a crystal (Form 6) of Compound (I) mono-ammonium salt, having diffraction peaks at diffraction angles (2θ±0.2°) of 15.1°, 16.4°, 17.0°, 21.6° and 25.9° in a powder X-ray diffraction;

(f5) a crystal (Form 6) of Compound (I) mono-ammonium salt, having diffraction peaks at diffraction angles (2θ±0.2°) of 12.0°, 15.1, 16.4°, 17.0°, 21.6°, 22.8° and 25.9° in a powder X-ray diffraction;

(f6) a crystal (Form 6) of Compound (I) mono-ammonium salt, having diffraction peaks at diffraction angles (2θ±0.2°) of 6.9°, 8.5°, 12.0°, 15.1°, 16.4°, 17.0°, 21.0°, 21.6°, 22.8° and 25.9° in a powder X-ray diffraction;

(g1) a crystal of sodium salt of Compound (I), having a diffraction peak at a diffraction angle (2θ±0.2° of 6.1° in a powder X-ray diffraction;

(g2) a crystal of sodium salt of Compound (I), having diffraction peaks at diffraction angles (2θ±0.2°) of 6.1 and 16.6° in a powder X-ray diffraction;

(g3) a crystal of sodium salt of Compound (I), having diffraction peaks at diffraction angles (2θ±0.2°) of 6.1, 9.3° and 16.6° in a powder X-ray diffraction;

(g4) a crystal of sodium salt of Compound (I), having diffraction peaks at diffraction angles (2θ±0.2°) of 6.10, 9.3°, 15.9°, 16.6° and 22.3° in a powder X-ray diffraction;

(g5) a crystal of sodium salt of Compound (I), having diffraction peaks at diffraction angles (2θ±0.2°) of 6.10, 9.3°, 13.4°, 15.9°, 16.6°, 20.6° and 22.3° in a powder X-ray diffraction;

(g6) a crystal of sodium salt of Compound (I), having diffraction peaks at diffraction angles (2θ±0.2°) of 6.10, 9.3°, 13.4°, 14.8°, 15.9°, 16.6°, 20.6°, 22.3°, 23.5° and 24.4° in a powder X-ray diffraction;

(h1) a crystal of Compound (I), having a diffraction peak at a diffraction angle (2θ±0.2°) of 5.6° in a powder X-ray diffraction;

(h2) a crystal of Compound (I), having diffraction peaks at diffraction angles (2θ±0.2°) of 5.6° and 13.9° in a powder X-ray diffraction;

(h3) a crystal of Compound (I), having diffraction peaks at diffraction angles (2θ±0.2°) of 5.6°, 13.9° and 16.8° in a powder X-ray diffraction;

(h4) a crystal of Compound (I), having diffraction peaks at diffraction angles (2θ±0.2°) of 5.6°, 8.9°, 11.4°, 13.9° and 16.8° in a powder X-ray diffraction; and (h5) a crystal of Compound (I), having diffraction peaks at diffraction angles (2θ±0.2°) of 5.6°, 7.9°, 8.9°, 11.4°, 13.9°, 16.8°, 22.1° and 23.1° in a powder X-ray diffraction.

The peaks in a powder X-ray diffraction, described above, are characteristic for each of the crystal (Form 1) of Compound (I) di-ammonium salt, the crystal (Form 2) of Compound (I) di-ammonium salt, the crystal (Form 3) of Compound (I) di-ammonium salt, the crystal (Form 4) of Compound (I) di-ammonium salt, the crystal (Form 5) of Compound (I) di-ammonium salt, the crystal (Form 6) of Compound (I) mono-ammonium salt, the crystal of Compound (I) sodium salt and the crystal of Compound (I).

Generally, errors in diffraction angles (2θ) within the range of ±0.2° may arise in powder X-ray diffraction, and thus the above-described values of diffraction angles need to be considered to include values within the range of approximately ±0.2°. Included in the present invention are, therefore, not only crystals with peaks at exactly the same diffraction angles in powder X-ray diffraction, but also crystals with peaks within an error range of approximately ±0.2° of the diffraction angles. Hence, "having a diffraction peak at a diffraction angle (2θ±0.2°) of 8.3° as used herein, for example, means "having a diffraction peak at a diffraction angle (2θ) of 8.10 to 8.5°. The same is also applied to other diffraction angles.

Generally, peak intensities and half-value widths of diffraction angles (2θ) in powder X-ray diffraction are different for each measurement because of differences in measurement conditions and dispersions of size and shape of each particle of powder crystal and not always stable even though forms of crystals are same. Therefore, in case of comparing a powder X-ray diffraction pattern, when diffraction angles (2θ) are the same but peak intensities, relative peak intensities and half-value widths are different, those differences does not imply that the measured forms of crystals differ from each other. Thus, a crystal of salt having a powder X-ray diffraction pattern, which has aforementioned differences with respect to characteristic diffraction peaks of a certain crystal of salt according to the present invention, means that the crystal has the same crystal form of the crystal of salt according to the present invention.

As used herein, "having a powder X-ray diffraction pattern substantially the same as the powder X-ray diffraction pattern shown in FIG. 3" means it includes not only the case of having exactly the same powder X-ray diffraction pattern as shown in FIG. 3, but also the case that peak intensities, relative peak intensities and half-value widths are different, or the case of having the characteristic peaks within an error range of approximately ±0.2° of the diffraction angles. Thus every crystal having such the powder X-ray diffraction pattern means that the crystal is identical to the crystal according to the present invention.

Methods for producing a salt of the Compound (I) and a crystal thereof will be described in detail.

(Production of Compound (I))

Compound (I) can be synthesized as described specifically in Production Example 1 or in Production Example 2 below.

(Method for Producing a Salt of the Compound (I))

A salt of the Compound (I) can be obtained by a conventional method for producing a salt. Specifically, it can be produced, for example, by suspending or dissolving Compound (I) in a solvent, with heating if necessary, then by adding a base (for example, sodium hydroxide, sodium carbonate for sodium salt; ammonia in ethanol and ammonium hydroxide for mono- or di-ammonium salt) to the obtained suspension or solution and by stirring or leaving the resultant suspension or solution for several minutes to several days at room temperature or with ice-bath cooling. A salt of the Compound (I) may be obtained as crystals or amorphous substances according to the production methods. Examples of the solvents to be used in these methods include alcohol solvents such as ethanol, 1-propanol and isopropanol; acetonitrile; ketone solvents such as acetone and 2-butanone; ester solvents such as ethyl acetate; saturated hydrocarbon solvents such as hexane and heptane; ether solvents such as t-butyl methyl ether or water. Each of these solvents may be used alone, or two or more may be mixed and used.

(Method for Producing a Crystal of the Salt of Compound (I))

A crystal of the salt of Compound (I) may be produced by the above-mentioned methods for producing a salt of the Compound (I), or by heat-dissolving a salt of the Compound (I) in a solvent and crystallizing it through cooling with stirring.

A salt of the Compound (I) to be used in the crystallization may be in any form: it may be a solvate, a hydrate, an anhydrate, an amorphous substance, a crystalline substance (including those consisting of a plurality of crystalline polymorphs) or a combination thereof.

Examples of the solvents to be used in the crystallization include alcohol solvents such as methanol, ethanol, isopropanol and 1-propanol; acetonitrile; amide solvents such as N,N-dimethylformamide; ester solvents such as ethyl acetate; saturated hydrocarbon solvents such as hexane and heptane; ketone solvents such as acetone and 2-butanone; ether solvents such as t-butyl methyl ether or water. Furthermore, each of these solvents may be used alone, or two or more may be mixed and used.

The amount of the solvent to be used may be suitably selected, provided that the lower limit is the amount with which the free form of Compound (I) or the salt thereof is dissolved by heating or the suspension can be stirred, and that the upper limit is the amount with which the yield of the crystal is not significantly reduced.

A seed crystal (e.g., the crystal of the desired salt of Compound (I)) may be added or may not be added during the crystallization. The temperature at which the seed crystal is added is not particularly limited, but is preferably 0 to 80° C.

As the temperature to be employed when the salt of Compound (I) is dissolved by heating, that at which Compound (I) dissolves may be suitably selected depending on the solvent, but it is preferably within the range between the temperature at which the recrystallization solvent starts to reflux and 50° C., and more preferably 65 to 55° C.

Cooling during the crystallization could give substances containing different forms of crystals (polymorphism) in the case of rapid cooling. It is therefore desirable to perform the cooling while controlling the cooling rate as appropriate based on the consideration of its effect on the quality, grain size and the like of the crystal. Preferred is, for example, cooling at a cooling rate of 40 to 5° C./hour. More preferred is cooling at a cooling rate of, for example, 25 to 5° C./hour.

Furthermore, the final crystallization temperature may be selected suitably for the yield, quality and the like of the crystal, but is preferably 30 to −25° C.

The target crystal can be obtained by isolating the formed crystal through a conventional filtration procedure, washing the filtered-off crystal with a solvent if necessary, and further drying it. As the solvent to be used for washing the crystal, the same solvent as in the crystallization can be used. Furthermore, each of these solvents may be used alone, or two or more may be mixed and used. Preferably, it is, for example, acetone, 2-butanone, ethyl acetate, t-butyl methyl ether, hexane or a mixed solvent of hexane/2-butanone.

The crystal isolated through the filtration procedure may be dried appropriately by leaving it in air or under nitrogen flow, or by heating.

As the drying time, the time until the amount of residual solvent becomes less than the predefined amount may be selected as appropriate depending on the amount of production, the drying apparatus, the drying temperature and the like. Furthermore, drying may be performed under airflow or under reduced pressure. The degree of pressure reduction may be selected as appropriate depending on the amount of production, the drying apparatus, the drying temperature and the like. The obtained crystal may be left in air as required after drying.

(Method for Producing a Crystal of Compound (I))

A crystal of Compound (I) can be obtained by a conventional method for producing a crystal as shown above.

A pharmaceutical composition of the present invention could be prepared by mixing pharmaceutically acceptable additives with the salt of Compound (I) or the crystal thereof. A pharmaceutical composition of the present invention could be prepared according to the known method such as a method described in the general rules for preparations of the Japanese Pharmacopoeia 17th edition.

A pharmaceutical composition of the present invention could be administered to patients appropriately depending on the dosage form.

A pharmaceutical composition of the present invention has applicability as a therapeutic agent for treating cancers since the salt of Compound (I) or the crystal thereof can potently activate STING pathway and show potent antitumor activities. Examples of cancers include glioma, melanoma and colon cancer.

The dosage of the salt of Compound (I) or the crystal thereof varies depending on the extent of the symptom, age, gender, body weight, dosage form, the type of the salt, the specific type of the disease and the like. In the case of adults, typically, about 30 g to 10 g, preferably 100 g to 5 g, and more preferably 100 g to 1 g per day is orally administered, or about 30 g to 1 g, preferably 100 g to 500 mg, and more preferably 100 g to 300 mg per day is administered by injection, in each case, in a single dose or in divided doses.

EXAMPLE

Hereinafter, the present invention will be described in detail with the production examples and examples. However, the present invention is not intended to be limited by these examples.

The following abbreviations may be used throughout the examples.

DMT: 4,4'-Dimethoxytrityl
(DMTO-:

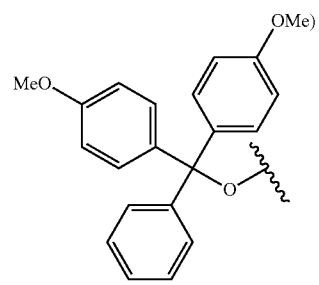

[Chem.3]

Bz: benzoyl
CE: cyanoethyl

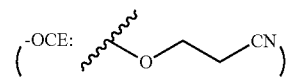

[Chem.4]

DEAD: diethyl azodicarboxylate
DIAD: diisopropyl azodicarboxylate
DCM: dichloromethane
DDTT: N,N-dimethyl-N'-(3-thioxo-3H-1,2,4-dithiazol-5-yl)formimidamide

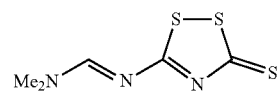

[Chem.5]

DMOCP: 2-chloro-5,5-dimethyl-1,3,2-dioxaphosphinane 2-oxide

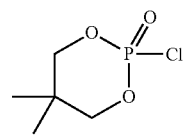

[Chem.6]

TBS: t-butyldimethylsilyl
3H-benzo[c][1,2]dithiol-3-one:

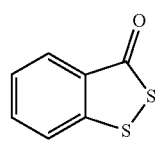

[Chem.7]

MTBE: methyl t-butyl ether
Powder X-Ray Diffraction

Each crystalline sample was placed on the sample stage of a powder X-ray diffractometer and the analysis was performed under one of the following conditions.

Transmission Method Conditions
Equipment: X'Pert Pro MPD or Empyrean (Spectris)
X-ray source: CuKα (45 kV, 40 mA)
Optical system: Focusing mirror
Soller slit: 0.02 or 0.04 radian
Detector: X'Celerator or PIXcel[1D] detector (semiconductor detection system)
Mode: Transmission
Scan range: from 3° or 5° to 350 or 40
Step size: 0.013, 0.017° or 0.033°
Scan step time: 9, 19, 305, 1976 or 2000 second
Sample holder: Kapton (registered trademark) film
Reflection Method Conditions
Equipment: RINT TTR-III (Rigaku)
X-ray source: CuKα (50 kV, 300 mA)
Detector: scintillation counter
Mode: Reflection
Slit: 0.5 mm (divergent slit), open (scattering slit), open (light-receiving slit)
Scan rate: 5° or 10°/minute
Sampling interval: 0.02
Scan range: from 3° or 5° to 350
Sample holder: aluminum holder
$^{1}$H NMR: Proton Nuclear Magnetic Resonance The coupling constant is recorded in hertz (Hz). The abbreviations of splitting patterns are as follows:

s: singlet, d: doublet, t: triplet, q: quartet, m: multiplex, bs: broad singlet, br s: broad singlet, dd: doublet of doublets, dt: doublet of triplets, br d: broad doublet, br t: broad triplet Unless indicated otherwise, $^{1}$H NMR spectra were taken on a Bruker 300 MHz or 400 MHz NMR.

Hygroscopicity

The obtained solid was weighed into a sampling cup and the sampling cup was placed inside an isothermal chamber at 25° C. The relative humidity (RH) was controlled from 0% to 95% using a gravimetric vapor sorption system and the sample weight at each RH stage was measured within a predetermined interval of time (e.g. every 2 minutes). The weight change at each RH stage was evaluated in a stepwise manner, and then was finally determined under the following criteria. The maximum weight change for each measurement is less than 0.01% (w/w) in 5 minutes or 0.002% (w/w) in 1 minute.

Production Example 1: Synthesis of Compound (I)

Step A

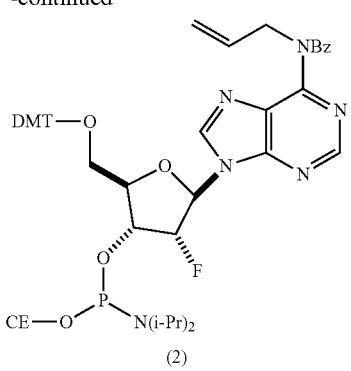

(2)

To a mixture of (2R,3R,4R,5R)-5-(6-benzamido-9H-purin-9-yl)-2-((bis(4-methoxyphenyl) (phenyl)methoxy) methyl)-4-fluorotetrahydrofuran-3-yl (2-cyanoethyl) diisopropylphosphoramidite (Compound (1)) (mixture of phosphorous diastereomers; 80.0 g, 91.332 mmol, 1 eq., ChemGenes Corporation catalog #ANP-9151), allyl alcohol (9.63 ml, 142 mmol, 1.55 eq) and triphenylphosphine (38.3 g, 146 mmol, 1.60 eq.) in THF (1.1 L) was added DEAD (40 wt % solution in toluene; 54.2 ml, 137 mmol, 1.5 eq.) at ambient temperature. Stirring was continued at ambient temperature and the reaction was monitored by LC/MS. Upon completion (19 h), the mixture was concentrated in vacuo (35° C.) and resultant mixture was purified by silica gel column chromatography (800 g×2 columns, 40 to 60% EtOAc in n-heptane buffered with 0.5% triethylamine) to give Compound (2) as a white foam (84.2 g, quantitative yield, mixture of phosphorous diastereomers).

$^{1}$H NMR (3:2 mixture of phosphorous diastereomers, 400 MHz, CDCl$_{3}$) δ1.14-1.21 (m, 12H), 2.40 (t, J=6.2 Hz, 1.2H), 2.59 (t, J=6.2 Hz, 0.8H), 3.27 (d, J=8.6 Hz, 1H), 3.52-3.66 (m, 5H), 3.78 (s 2.4H), 3.79 (s 3.6H), 4.28-4.34 (m, 1H), 4.84-4.96 (m, 0.4H), 4.99 (d, J=5.5 Hz, 2H), 4.95-5.10 (m, 0.6H), 5.05 (d, J=10.9 Hz, 1H), 5.22 (br d, J=17.6 Hz, 1H), 5.64 (br d, J=53.2 Hz, 0.6H), 5.70 (br d, J=51.6 Hz, 0.4H), 5.96-6.75 (m, 1H), 6.20 (d, J=16.0 Hz, 0.6H), 6.24 (d, J=17.2 Hz, 0.4H), 6.74-6.79 (m, 4H), 7.02-7.06 (m, 2H), 7.17-7.24 (m, 8H), 7.32-7.34 (m, 2H), 7.41-7.44 (m, 2H), 8.11 (s, 1H), 8.52 (s, 0.4H), 8.54 (s, 0.6H).

Step B

[Chem.8]

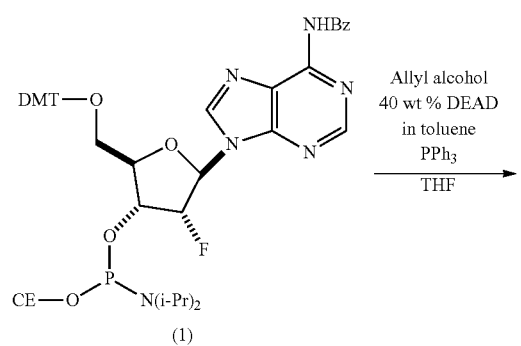

(1)

[Chem.9]

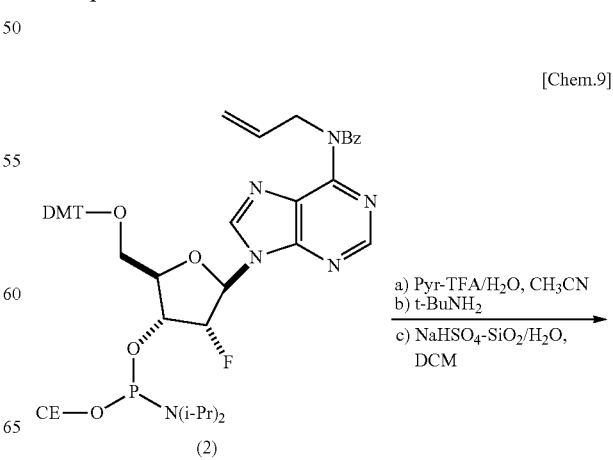

(2)

-continued

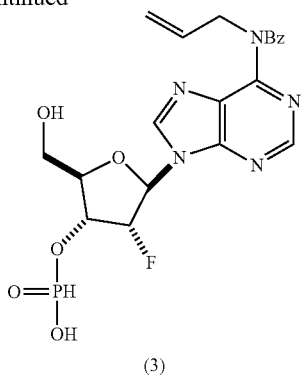

(3)

To a solution of Compound (2) (3.00 g, 3.28 mmol, 1 eq.) in acetonitrile (30 ml) was added water (0.118 ml, 6.55 mmol, 2.0 eq.) and pyridine trifluoroacetate salt (0.759 g, 3.93 mmol, 1.2 eq.). After stirring at ambient temperature for 1 minute, tert-butylamine (14.5 g, 21.0 ml, 0.20 mol, 60 eq.) was added. Upon complete cleavage of cyanoethyl group (monitored by LC/MS), the reaction mixture was concentrated in vacuo and azeotroped twice with acetonitrile. The crude mixture was dissolved in DCM (45.0 ml) and treated with water (0.118 ml, 6.55 mmol, 2.0 eq.) and $NaHSO_4$—$SiO_2$ (1.18 g, 6.55 mmol, 2 eq.) at ambient temperature. Upon complete cleavage of DMT group (monitored by LC/MS, approximately 1 hour), the reaction mixture was filtered and rinsed twice with DCM/MeOH (9/1, 20 ml). The combined filtrates were concentrated in vacuo and treated with 1:1 mixture of n-heptane/toluene (~30 ml). The top layer was removed by decantation. The same operation was repeated once more with n-heptane/toluene (1/1, 30 ml) and the bottom layer was azeotroped twice with acetonitrile to give Compound (3) (100% theoretical yield assumed). The product was used in the next step without further purification.

Step C

[Chem.10]

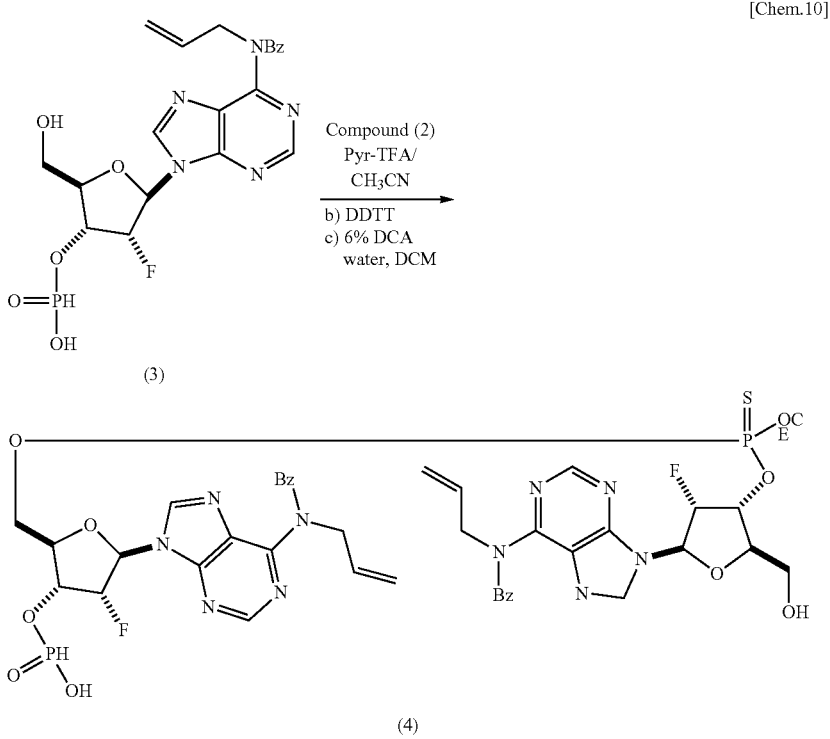

To a mixture of Compound (3) (1.56 g, 3.27 mmol, 1 eq.) and Compound (1) (3.00 g, 3.28 mmol, 1 eq.) in acetonitrile (30 ml) was added pyridine trifluoroacetate salt (azeotropically dried with pyridine; 0.760 g, 3.94 mmol, 1.25 eq.). After 5 minutes, DDTT (0.840 g, 4.09 mmol, 1.30 eq., ChemGenes Corporation catalog #RN-1588) was added and, upon complete sulfurization (monitored by LC/MS), the reaction mixture was concentrated in vacuo. The residue was dissolved in DCM (30 ml) and treated with water (0.57 ml, 32 mmol, 10 eq.) and 6% dichloroacetic acid (1.56 ml, 18.9 mmol, 6.0 eq.) in DCM (30 ml). After 20 minutes, the reaction was quenched with pyridine (20 ml) and concentrated in vacuo. The residue was azeotroped with pyridine to give Compound (4) (3.22 g, 100% theoretical yield assumed). The product was used in next the step without further purification.

Step D

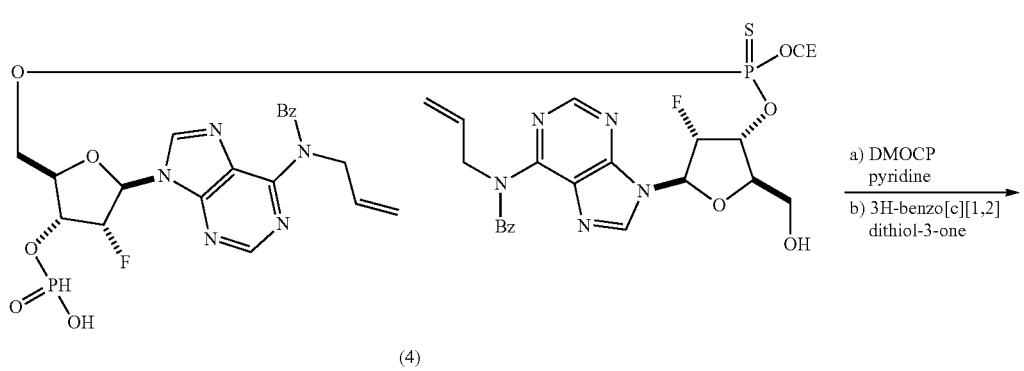

(4)

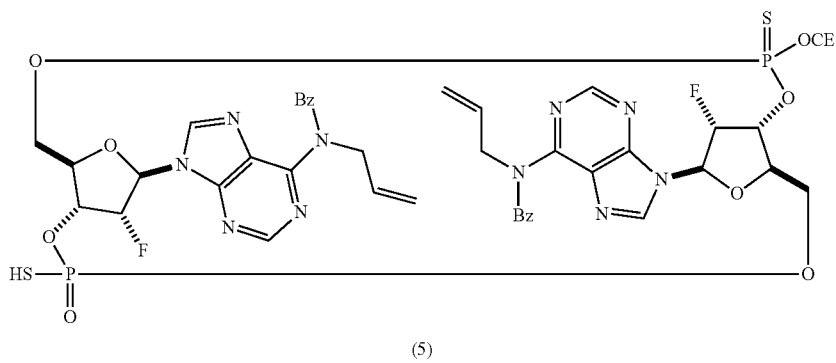

(5)

To a solution of Compound (4) (3.22 g, 3.15 mmol, 1 eq.) in pyridine (100 ml) was added DMOCP (1.45 g, 7.88 mmol, 2.50 eq.) at ambient temperature. Upon complete macrocyclization (monitored by LC/MS), water (1.7 ml, 94.5 mmol, ×10 fold relative to DMOCP) was added followed by 3H-benzo[c][1,2]dithiol-3-one (0.795 g, 4.73 mmol, 1.5 eq.). Upon complete sulfurization (approximately 40 minutes), the reaction mixture was partially concentrated in vacuo to approximately 15 ml and poured into a mixture of saturated aqueous NaHCO₃ (50 ml) and water (30 ml). After 10 min stirring at ambient temperature, the mixture was extracted with 1:1 mixture of EtOAc/MTBE (60 ml×3 times). The organic layers were combined, washed with brine (25 ml), dried over MgSO₄ and concentrated in vacuo. The residue was purified by silica gel column chromatography (0-20% MeOH in DCM) to give Compound (5) (3.31 g, 3.20 mmol, 100% theoretical yield assumed) as a brown oil. The product was used in the next step without further purification.

Step E

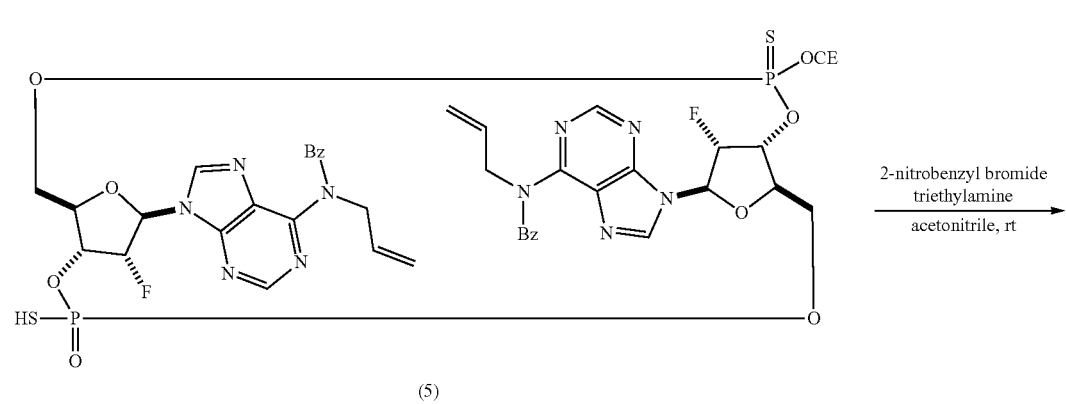

(5)

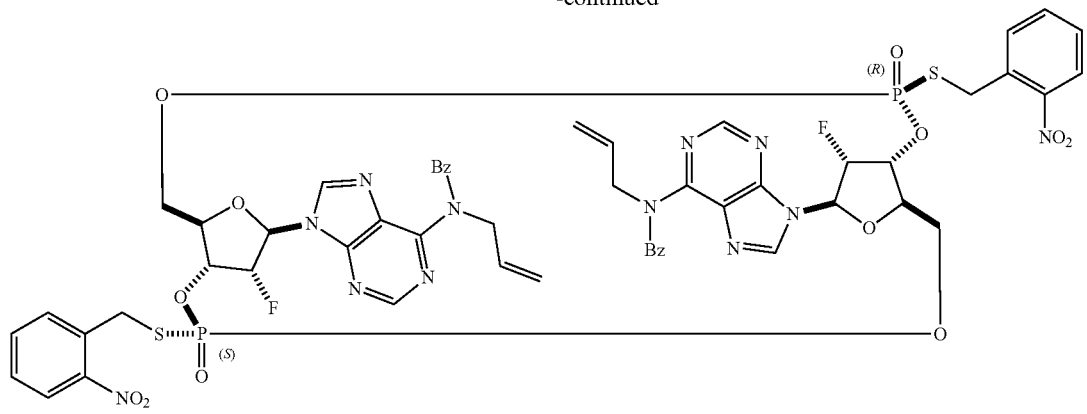

(6) (SpRp)

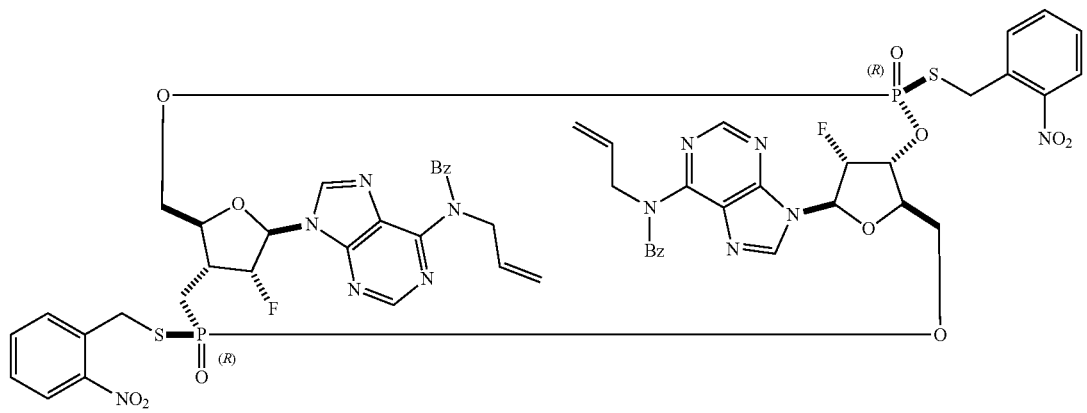

(7) (RpRp)

To a solution of Compound (5) (3.3 g, 3.20 mmol, 1 eq.) in acetonitrile (66.2 ml) was added 2-nitrobenzyl bromide (2.42 g, 11.2 mmol, 3.50 eq.) and triethylamine (1.78 ml, 12.8 mmol, 4.00 eq.). Upon complete reaction (monitored by LC/MS, approximately 20 hours at ambient temperature), the reaction mixture was concentrated in vacuo and purified by silica gel column chromatography (60% ethyl acetate/n-heptane to 100% ethyl acetate) to give 0.568 g product as a mixture of phosphorous diastereomers. Preparative HPLC separation of the diastereomers gave Compound (6) (SR isomer; 0.225 g, 0.180 mmol, 5.6% overall yield from Compound (2)) and Compound (7) (RR isomer; 0.187 g, 0.149 mmol, 4.7% overall yield from Compound (2)).

Compound (6) (SpRp) $^1$H NMR (400 MHz, CDCl$_3$) δ(ppm): 8.63 (s, 1H), 8.61 (s, 1H), 8.04-8.00 (m, 2H), 7.99 (s, 1H), 7.90 (s, 1H), 7.65-7.44 (m, 8H), 7.40-7.31 (m, 4H), 7.25-7.21 (m, 4H), 6.15-5.89 (m, 5H), 5.61 (dd, J=52.0, 5.1 Hz, 1H), 5.55 (ddd, J=51.2, 4.7, 2.7 Hz, 1H), 5.51-5.42 (m, 1H), 5.31-5.22 (m, 2H), 5.11 (dd, J=3.9, 9.8 Hz, 2H), 5.04-4.95 (m 4H), 4.55-4.37 (m 7H), 4.29-4.12 (m 3H).

Compound (7) (RpRp) $^1$H NMR (400 MHz, CDCl$_3$) δ(ppm): 8.65 (s, 2H), 8.06 (dd, J=1.4, 8.0 Hz, 2H), 7.98 (s, 2H), 7.57-7.52 (m, 6H), 7.47-7.32 (m, 6H), 7.25-7.21 (m, 4H), 6.15 (d, J=18.7 Hz, 2H), 6.09-5.99 (m, 2H), 5.82-5.76 (m, 2H), 5.60 (dd, J=51.8, 4.9 Hz, 2H), 5.27 (dd, J=1.2, 17.2 Hz, 2H), 5.12 (dd, J=1.0, 10.4 Hz, 2H), 5.06-4.96 (m, 4H), 4.55-4.40 (m, 4H), 4.36-4.24 (m, 4H), 4.21-4.02 (m, 2H).

TABLE 1

| Preparative HPLC conditions: | | | | | | |
|---|---|---|---|---|---|---|
| Instrument | | Agilent 1200 | | | | |
| HPLC column | | Waters Sunfire Prep C18 OBD column, 5 um, 30 × 250 mm, #186003969 | | | | |
| Flow rate | | 50 ml/min | | | | |
| mobile phase | | A: water, B: acetonitrile | | | | |
| Gradient | Time (min) | 0 | 8 | 9.9 | 10 | 12 |
| | B % | 50 | 99 | 99 | 50 | 50 |
| Run time | | 12 min | | | | |
| Injection volume | | 150 μl (0.08 g/ml in acetonitrile) | | | | |
| detection | | UV 254 nm | | | | |
| Retention time | Compound (6) (SpRp) | 7.7 min | | | | |
| | Compound (7) (RpRp) | 8.0 min | | | | |

Step F

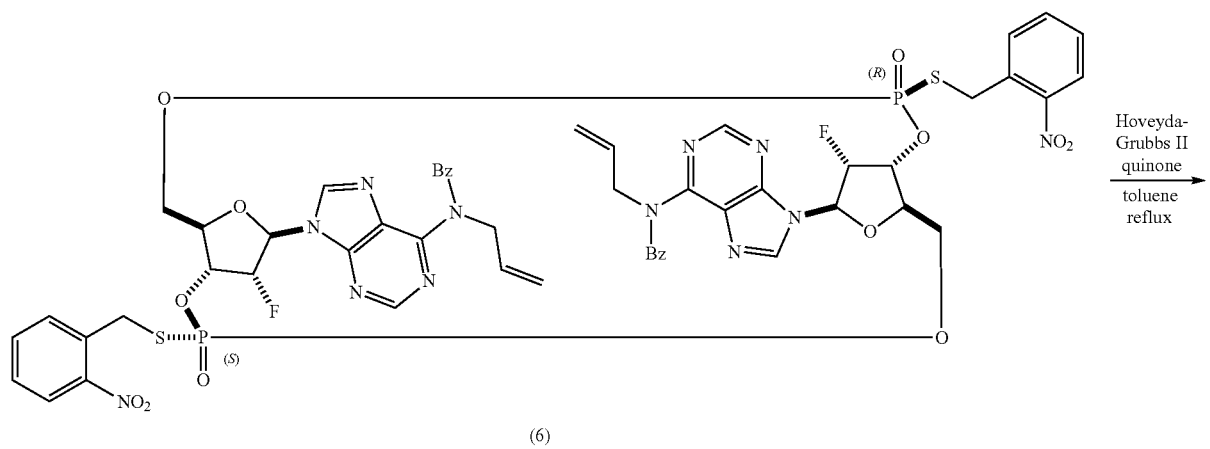

(6)

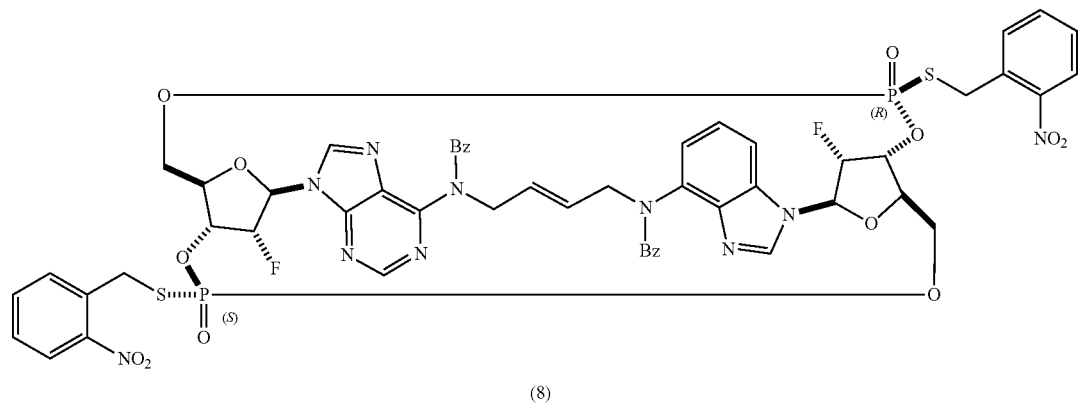

(8)

To a heated (90° C.) solution of Compound (6) (519 mg, 0.414 mmol, 1 eq.) in toluene (519 ml) was added Hoveyda-Grubbs Catalyst™ 2nd generation ((1,3-Bis-(2,4,6-trimethylphenyl)-2-imidazolidinylidene)dichloro (o-isopropoxyphenylmethylene)ruthenium; available at SIGMA-ALDRITCH (registered trademark) Catalog No. 569755; CAS 301224-40-8; 91 mg, 0.15 mmol, 0.35 eq.) and quinone (0.102 ml, 1.243 mmol, 3.0 eq.). The mixture was heated to reflux and reaction progress was monitored by LC/MS. After 3 hours an additional catalyst was added (91 mg, 0.15 mmol, 0.35 eq.) and the reaction was continued for additional 3 hours. After cooling down, the mixture was treated with DMSO (0.59 ml, 8.3 mmol, 20 eq.) at ambient temperature for 15 hours, concentrated in vacuo and purified by silica gel column chromatography ($SiO_2$ 25 g, 66% ethyl acetate in n-heptane to 100% ethyl acetate) to give Compound (8) (200 mg, 0.163 mmol, 39% yield) as a brown dry foam.

$^1$H NMR (400 MHz, $CDCl_3$) δ (ppm): 8.19 (s, 1H), 8.12 (dd, J=7.8 Hz, 1.9 Hz, 1H), 8.10 (s, 1H), 8.02 (d, J=8.2 Hz, 1H), 7.89 (s, 1H), 7.63 (br d, J=7.0 Hz, 1H), 7.53-7.41 (m, 10H), 7.35-7.30 (m, 2H), 7.25-7.20 (m, 4H), 6.23 (d, J=17.6 Hz, 1H), 6.14 (d, J=18.8 Hz, 1H), 5.86-5.75 (m, 1H), 5.75 (dt, J=15.3, 5.0 Hz, 1H), 5.67 (dt, J=15.3, 4.7 Hz, 1H), 5.60 (dd, J=52.0, 3.9 Hz. 1H), 5.48 (dd, J=50.4, 3.9 Hz. 1H), 5.50-5.39 (m, 1H), 4.91-4.64 (m, 4H), 4.57-4.25 (m, 9H), 4.15 (d, J=7.03 Hz, 1H), 4.11 (d, J=7.03 Hz, 1H).

Step G

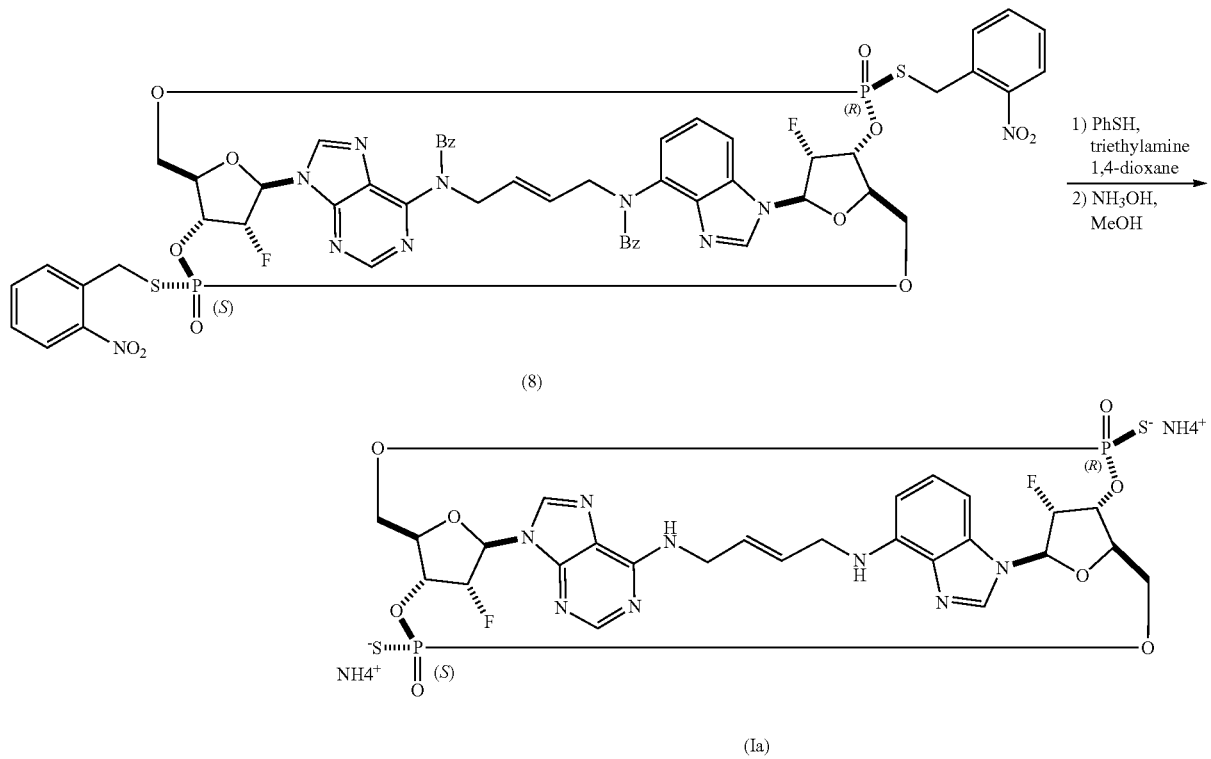

To a solution of Compound (8) (88 mg, 0.072 mmol, 1 eq.) in 1,4-dioxane (1.76 ml) was added thiophenol (0.88 mL, 8.55 mmol, 119 eq.) and triethylamine (0.88 mL, 6.31 mmol, 88 eq.). The resulting mixture was stirred at ambient temperature. Upon complete reaction (monitored by LC/MS, 13 hours), methanol (5.28 ml) and 28% ammonium hydroxide (3.52 ml) were added and resultant mixture was heated to 50° C. Upon complete reaction (monitored by LC/MS, 5 hours), the mixture was cooled to ambient temperature and the resultant brownish slurry was filtered and rinsed with water (15 ml). The filtrate was filtered again to remove additional solids. The final filtrate was extracted twice with a 1:1 mixture of toluene and n-heptane (30 ml). The aqueous layer was concentrated in vacuo and then re-suspended in water (6 ml). The resulting solid was filtered off and the filtrate was subjected to preparative HPLC to give di-ammonium salt of Compound (I) (also referred to as Compound (1a)) (39 mg, 0.050 mmol, 70% yield) as a white solid.

Compound (1a) (SpRp, trans) $^1$H NMR (400 MHz, CD$_3$OD) δ (ppm): 9.05 (s, 1H), 8.33 (s, 1H), 8.25 (s, 1H), 8.12 (s, 1H), 6.34 (br s, 2H), 5.88 (br s, 2H), 5.66 (br d, J=51.6 Hz, 1H), 5.59 (br d, J=52.2 Hz, 1H), 5.01 (br s, 2H), 4.68-4.34 (m, 6H), 4.07-3.82 (m, 2H), 3.79-3.55 (m, 2H);

$^{31}$P NMR (162 MHz, CD$_3$OD) δ(ppm): 55.48 (s, 1P), 55.16 (s, 1P).

TABLE 2

Compound (1a) Preparative HPLC conditions:

| Instrument | Agilent 1200/1260 AS/FC |
|---|---|
| HPLC column | Waters XBridge C18, 10 × 100 mm, #1413 |
| Flow rate | 3.0 ml/min |
| Column temperature | 35° C. |
| mobile phase | A: 0.1% NH$_4$OH in water, B: 0.1% NH$_4$OH in acetonitrile |
| Gradient (B%) | 0 → 50 |
| Run time | 20 min |
| Injection volume | 50 ul (4 mg/ml in water) |
| detection | UV 260 nm |
| Retention time | 6.5 min |

Production Example 2: (Alternative Synthesis for Compound (1a))

Stage 1

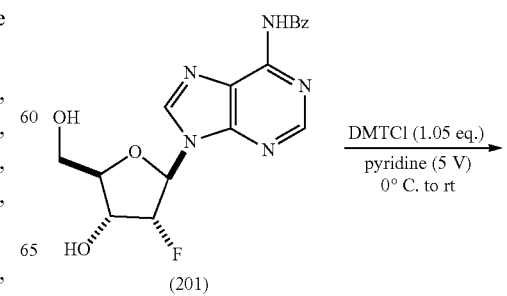

-continued

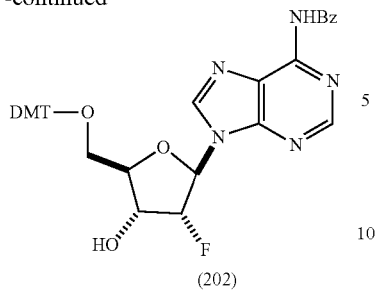

(202)

-continued

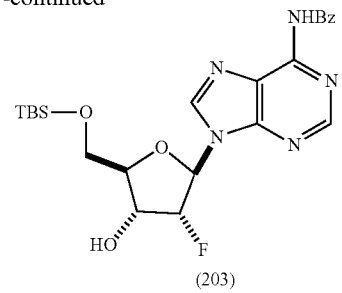

(203)

Compound (201) (570 g, 1.53 mol, 1 wt, 1 vol, 1 eq.) was dissolved in pyridine (2.85 L, 35.2 mol, 4.89 wt, 5.0 vols, 23 eq.). The mixture was cooled to 2.6° C. and treated with 4,4'-dimethoxytrityl chloride (DMTCl; 543 g, 1.60 mol, 0.953 wt, 1.05 eq.). The mixture was stirred at 0 to 5° C. for 2 h and then allowed to warm to ambient temperature. The reaction was monitored by LC/MS and complete conversion was confirmed after overnight stirring. The reaction mixture was cooled to below 5° C. and quenched by treatment with MeOH (124 ml, 3.05 mol, 0.172 wt, 0.217 vol, 2.0 eq.) for 15 minutes. The mixture was co-evaporated with toluene (2.00 L, 3.04 wt, 3.51 vol) under vacuum and then diluted with a mixture of EtOAc (2.850 L, 4.5 wt, 5.0 vol) and n-heptane (2.85 L, 3.42 wt, 5.0 vol). The organic layer was washed with saturated $NaHCO_3$ (9 wt % solution in water; 2.0 L, 3.5 vol). An additional EtOAc (2.85 L, 4.5 wt, 5.0 vol) was added to completely dissolve the crude product. After stirred for 5 minutes, the two layers were separated. The organic layer was washed with water (2.0 L, 3.5 wt, 3.5 vol). Solid began slowly precipitating out of the organic layer. The water layer was separated. The organic layer was then concentrated to approx. 1 vol. The crude product was slurried with a mixture of n-heptane (2.00 L, 2.40 wt, 3.51 vol) and toluene (0.50 L, 0.76 wt, 0.88 vol). After stirring for 15 minutes, the pale yellow solid was collected by vacuum filtration. The filter cake was sequentially rinsed with: (1) a mixture of n-heptane (0.60 L, 0.72 wt, 1.05 vol) and toluene (0.30 L, 0.46 wt, 0.53 vol), and then (2) n-heptane (3.00 L, 3.6 wt, 5.26 vol). The solid was dried with no heat for 30 minutes and then transferred to trays for drying at 50° C. in a vacuum oven overnight to give Compound (202) as pale yellow solid (996.7 g, 1.47 mol, 1.75 wt, 97% yield).

$^1$H NMR (400 MHz, CHLOROFORM-d) δ(ppm): 8.99 (s, 1H), 8.76 (s, 1H), 8.21 (s, 1H), 8.04-8.00 (m, 2H), 7.64-7.59 (m, 1H), 7.57-7.50 (m, 2H), 7.41-7.36 (m, 2H), 7.32-7.15 (m, 7H), 6.83-6.76 (m, 4H), 6.31 (dd, J=2.5, 17.0 Hz, 1H), 5.68 (ddd, J=2.3, 4.7, 52.7 Hz, 1H), 4.88-4.77 (m, 1H), 4.26-4.21 (m, 1H), 3.77 (s, 6H), 3.57 (dd, J=3.1, 10.9 Hz, 1H), 3.43 (dd, J=4.1, 10.7 Hz, 1H), 2.60 (br s, 1H).

Stage 1'

Compound (201) (430 g, 1.15 mol, 1 wt, 1 vol, 1 eq.) and imidazole (118 g, 1.73 mol, 0.274 wt, 1.50 eq.) were dissolved in DMF (1.72 L, 3.78 wt, 4.0 vol) and the resultant mixture was cooled to 5° C. TBS-Cl (191 g, 1.27 mol. 0.444 wt, 1.10 eq.) was added. The mixture was stirred at 0 to 11° C. for 2 h, allowed to slowly warm to ambient temperature (progress monitored by LCMS). The reaction was complete 6 h after TBS-Cl addition, yet allowed to stir at ambient temperature for an additional 20 h. The mixture was cooled to 2° C. and treated with methanol (93 ml, 74 g, 2.3 mol, 0.17 wt, 0.22 wt, 2.0 eq.) for 10 minutes. The reaction mixture was diluted with a mixture of MTBE (1.72 L, 1.23 kg, 2.96 wt, 4.0 vol) and EtOAc (1.72 L, 1.55 kg, 3.60 wt, 4.0 vol) followed by saturated $NH_4Cl$ (28 wt % solution in water; 2.15 L, 5.0 vol). Solids began slowly falling out of solution. The mixture was allowed to warm to 24° C. and water (1.08 L, 1.08 kg, 2.5 wt, 2.5 vol) was added to the (T-internal=22° C.). More solids began precipitating out of the mixture. An additional water (1.08 L, 1.08 kg, 2.5 wt, 2.5 vol) and MTBE (1.40 L, 1.04 kg, 2.4 wt, 3.3 vol) were added to the mixture. The off-white solid was collected by vacuum filtration. The reactor was rinsed with water (320 ml, 0.74 vol) and then MTBE (1.80 L, 1.33 kg, 3.10 wt, 4.19 vol) to transfer any remaining solid to the filter. The filter cake was rinsed sequentially with: (1) water (1.80 L, 1.80 kg, 4.2 wt, 4.2 vol), (2) water (1.80 L, 1.80 kg, 4.2 wt, 4.2 vol), (3) a mixture of MTBE (0.90 L, 0.67 kg, 1.5 wt, 2.1 vol) and n-heptane (0.90 L, 0.62 kg, 1.4 wt, 2.1 vol), (4) a mixture of MTBE (0.90 L, 0.67 kg, 1.5 wt, 2.1 vol) and n-heptane (0.90 L, 0.62 kg, 1.4 wt, 2.1 vol). The recovered solid was dried under vacuum at 40° C. over 2 days to give Compound (203) as white solid (483 g, 0.991 mol, 1.12 wt, 86% yield).

$^1$H NMR (400 MHz, CHLOROFORM-d) δ (ppm): 8.97 (s, 1H), 8.82 (s, 1H), 8.36 (s, 1H), 8.04-8.00 (m, 2H), 7.64-7.58 (m, 1H), 7.56-7.51 (m, 2H), 6.40 (dd, J=2.3, 16.0 Hz, 1H), 5.45 (ddd, J=2.7, 4.3, 53.1 Hz, 1H), 4.75-4.66 (m, 1H), 4.22-4.17 (m, 1H), 4.07 (dd, J=2.3, 11.7 Hz, 1H), 3.91 (dd, J=2.7, 11.7 Hz, 1H), 2.38 (dd, J=2.7, 7.0 Hz, 1H), 0.92 (s, 9H), 0.11 (s, 3H), 0.11 (s, 3H).

Stage 2

[Chem. 16]

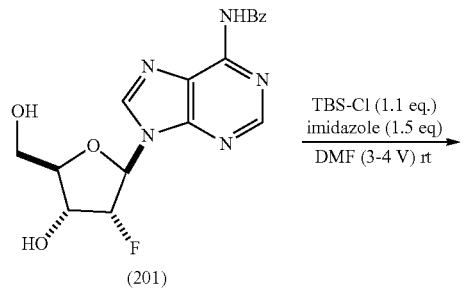

(201)

TBS-Cl (1.1 eq.)
imidazole (1.5 eq)
―――――――→
DMF (3-4 V) rt

[Chem. 17]

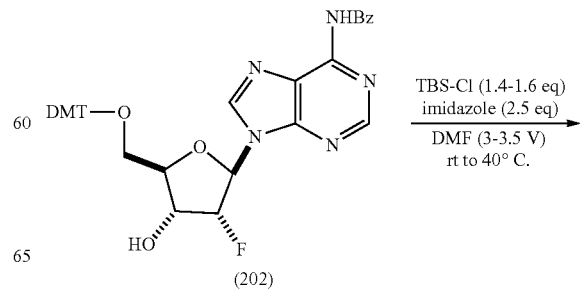

(202)

TBS-Cl (1.4-1.6 eq)
imidazole (2.5 eq)
―――――――→
DMF (3-3.5 V)
rt to 40° C.

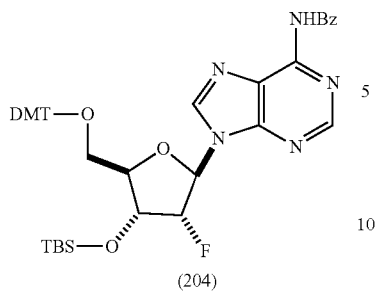

(204)

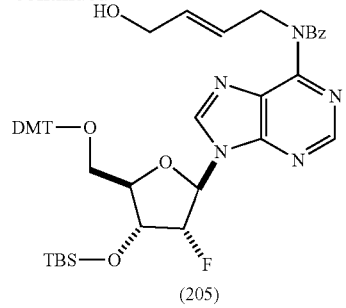

(205)

Compound (202) (993 g, 1.47 mol, 1 wt, 1 vol, 1 eq.) and imidazole (150 g, 2.20 mol, 0.151 wt, 1.5 eq.) were dissolved in DMF (3.48 L, 3.28 kg, 3.3 wt, 3.5 vol) and the mixture was cooled to 5° C. TBS-Cl (244 g, 1.62 mol, 0.245 wt, 1.10 eq.) was added. The reaction was stirred at 0 to 5° C. for 2 h, allowed to slowly warm to ambient temperature and monitored by LCMS. After 17 h, an additional imidazole (100 g, 1.47 mol, 0.10 wt, 1.0 eq.) and TBS-Cl (11 g, 735 mmol, 0.112 wt, 0.50 eq.) were added and stirring was continued at ambient temperature for 2 h and at 35° C. for 2 h. The resulting mixture was cooled to 13.6° C. and treated with MeOH (119 ml, 2.94 mol, 2 eq.) for 10 minutes. In a separate reactor was added ice (5 kg, 5 wt) and saturated NH$_4$Cl (28 wt % solution in water; 5.0 L, 5 vol). The reaction mixture was added to the ice/NH$_4$Cl mixture. An off white solid began precipitating out of solution immediately. An additional 2 kg of ice (2 kg, 2 wt) and water (3.0 L, 3 vol) were added to the mixture. The reaction flask was rinsed with water (0.50 L, 0.5 vol) and the rinsate was added to the mixture. n-Heptane (2.00 L, 2 vol) was added to the mixture and stirring was continued for 10 minutes. The off white solid was collected by vacuum filtration. The filter cake was rinsed with: (1) water (4.0 L, 4.0 vol), (2) water (4.0 L, 4.0 vol), (3) n-heptane (4.0 L, 4.0 vol), (4) n-heptane (4.0 L, 4.0 vol). The recovered solid was dried under vacuum at 45° C. for 4 days to give Compound (204) as off-white solid (1.095 kg, 1.39 mol, 1.10 wt, 94% yield).

$^1$H NMR (400 MHz, CHLOROFORM-d) δ (ppm): 9.09 (s, 1H), 8.78 (s, 1H), 8.28 (s, 1H), 8.02 (d, J=7.4 Hz, 2H), 7.63-7.59 (m, 1H), 7.55-7.50 (m, 2H), 7.37 (d, J=7.1 Hz, 2H), 7.29-7.17 (m, 7H), 6.79 (d, J=7.9 Hz, 4H), 6.29 (dd, J=2.9, 16.2 Hz, 1H), 5.60 (ddd, J=2.7, 3.9, 53.1 Hz, 1H), 4.78 (ddd, J=4.7, 6.4, 15.8 Hz, 1H), 4.26-4.22 (m, 1H), 3.77 (s, 6H), 3.58 (dd, J=3.1, 10.9 Hz, 1H), 3.26 (dd, J=3.7, 10.7 Hz, 1H), 0.85 (s, 9H), 0.10 (s, 3H), 0.02 (s, 3H).

Stage 3

[Chem. 18]

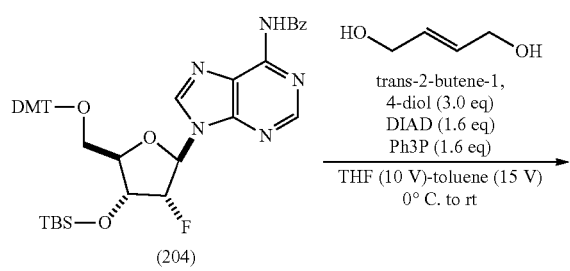

(204)

trans-2-butene-1,
4-diol (3.0 eq)
DIAD (1.6 eq)
Ph3P (1.6 eq)
——————————————→
THF (10 V)-toluene (15 V)
0° C. to rt Compound (204) (1000 g, 1.27 mol, 1 wt, 1 vol, 1 eq.) and trans-2-butene-1,4-diol (olefin geometry confirmed by $^1$H-NMR; 335 g, 3.80 mol. 0.335 wt, 3.0 eq.) were azeotroped twice with THF (3.0 L, 3.0 vol). The residue was dissolved in a mixture of THF (10 L, 10 vol) and toluene (15 L, 15 vol). Triphenylphosphine (432 g, 1.65 mol, 0.432 wt, 1.3 eq.) was added and then the reaction mixture was cooled to −5° C. DIAD (0.320 L, 1.65 mol, 333 g, 0.333 wt, 0.320 vol, 1.3 eq.) was added slowly over 20 minutes while keeping T-internal below 5° C. The reaction was stirred at 0-5° C. for 1 h and monitored by LCMS. The ice bath was removed and the mixture was allowed to warm up to rt. After overnight stirring (17 h), triphenylphosphine (83 g, 0.32 mol, 0.083 wt, 0.25 eq) and DIAD (62 ml. 0.32 mol. 64 g, 0.064 wt, 0.062 vol. 0.25 eq.) were added. After additional 1 h at rt, the reaction mixture was diluted with MTBE (10 L, 10 vol), washed twice with half-saturated NaCl (18 wt % solution in water; 2×4 L) and concentrated in vacuo to a thick oil. The mixture was re-dissolved in a mixture of MTBE (4.00 L, 4 vol) and n-heptane (0.50 L, 0.5 vol) and then cooled to 0° C. A seed crystal of triphenylphosphine oxide was added to the solution. Solids slowly began precipitating out of solution and was stirred overnight. The white solid was collected by vacuum filtration and rinsed with MTBE (2 L, 2 vol) to isolate 540 g of triphenylphosphine oxide. The filtrate was concentrated and purified via Biotage 150 L KP-Sil (SiO$_2$ 5 kg; pretreated with 1% TEA in heptane/EtOAc; eluents: n-heptane/EtOAc (48 L of 33% EtOAc with 1% TEA, 24 L of 50% EtOAc with 1% TEA, 24 L of 66% EtOAc with 1% TEA)→100% EtOAc with 1% TEA). The column was monitored by TLC (2:1 EtOAc/n-heptane). The clean product fractions were combined and concentrated under vacuum to give Compound (205) as pale white foam solid (634 g, contained 14 wt % DIAD derived co-product, net 545 g, 0.63 mol, 50% adjusted yield). The mixture fractions were combined and concentrated under vacuum to give pale yellow foam solid (750 g), which was subjected to repurification via Biotage 150M HP-Sphere (2.5 kg SiO$_2$; pretreated with 1% TEA in n-heptane/EtOAc; loaded sample with toluene eluents: n-heptane/EtOAc/1% TEA (12 L of 50% EtOAc with 1% TEA, 16 L 66% EtOAc with 1% TEA)->EtOAc with 1% TEA). The column was monitored by TLC (2/1/0.03 EtOAc/n-heptane/TEA). The clean product fractions were combined and concentrated under vacuum to give additional Compound (205) as pale white foam solid (206 g, 0.24 mol, 18% yield).

$^1$H NMR (400 MHz, CHLOROFORM-d) δ (ppm): 8.58 (s, 1H), 8.10 (s, 1H), 7.43-7.37 (m, 2H), 7.32-7.28 (m, 2H), 7.24-7.15 (m, 8H), 7.03-6.98 (m, 2H), 6.78-6.73 (m, 4H), 6.18 (dd, J=2.7, 17.2 Hz, 1H), 5.88 (td, J=5.5, 15.6 Hz, 1H), 5.77 (td, J=5.1, 15.6 Hz, 1H), 5.60 (ddd, J=2.7, 4.3, 53.1 Hz, 1H), 5.03-4.96 (m, 2H), 4.91 (ddd, J=4.5, 6.6, 16.6 Hz, 1H), 4.18-4.14 (m, 1H), 3.88-3.82 (m, 2H), 3.78 (s, 6H), 3.52 (dd, J=2.7, 10.9 Hz, 1H), 3.14 (dd, J=3.5, 10.9 Hz, 1H), 0.85 (s, 9H), 0.10 (s, 3H), 0.01 (s, 3H).

Stage 4

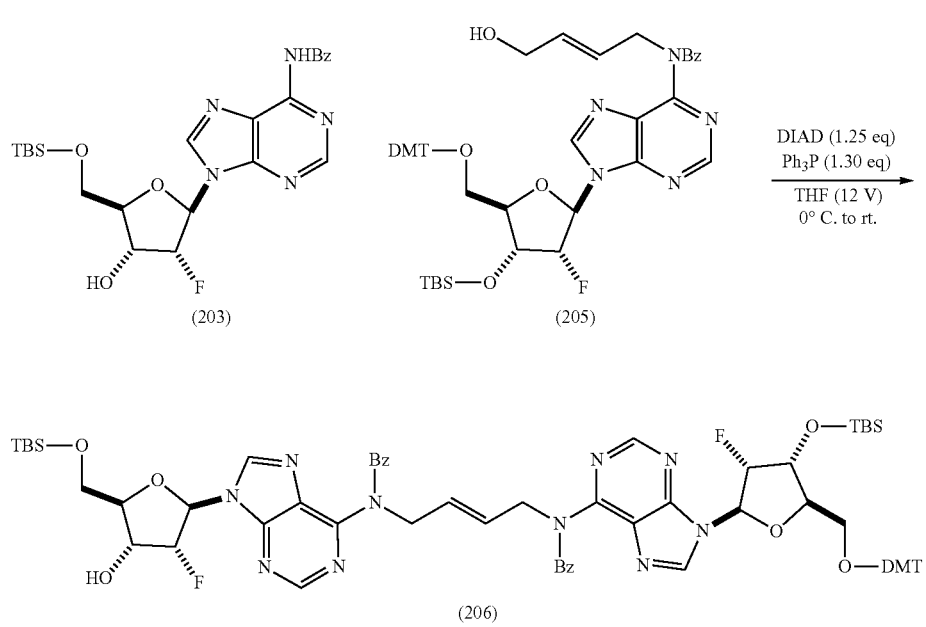

[Chem. 19]

Compound (205) (800 g, 0.930 mol, 1 wt, 1 vol, 1 eq.) and Compound (203) (522 g, 1.07 mol, 0.652 wt, 1.15 eq.) were azeotropically dried with THF (2×3 L, 2×3.8 vol) and re-dissolved in THF (9.60 L, 8.45 kg, 12.0 vol) at rt. Triphenylphosphine (317 g, 1.21 mol, 0.396 wt, 1.30 eq.) was added and the mixture was cooled below −5° C. DIAD (226 ml, 1.16 mol, 235 g, 0.294 wt, 0.283 vol, 1.25 eq.) was added T-internal below 7° C. The reaction was allowed to warm to rt slowly. The reaction was monitored by LCMS. After 21 h, the reaction mixture was concentrated in vacuo to a thick oil, azeotroped with n-heptane (2.00, 1.37 kg, 1.71 wt, 2.50 vol) and then re-dissolved in a mixture of MTBE (2.40 L, 1.78 kg, 2.2 wt, 3.0 vol) and n-heptane (800 ml, 547 g, 0.68 wt, 1.0 vol). The solution was seeded with triphenylphosphine oxide and cooled to 5° C., diluted with n-heptane (400 ml, 274 g, 0.34 wt, 0.50 vol) and stirred at 5° C. for 30 minutes. The white solid precipitate was collected by vacuum filtration and rinsed with 2:1 (v/v) mixture of MTBE and n-heptane (1.8 L) to give triphenylphosphine oxide (455 g). The filtrate was concentrated under vacuum and purified via Biotage 150 L KP-Sil (SiO$_2$ 5 kg; pretreated with 1% TEA; loaded sample by dissolving in toluene eluents: 9:1 n-heptane/EtOAc (16 L) and 1% TEA, 3.6:1 (46 L), 2:1 (20 L) and 1% TEA, 1:1 (30 L) and 1% TEA, and 100% EtOAc (16 L) and 1% TEA). The combined clean product fractions were concentrated under vacuum to give Compound (206) as off white solid foam (662.2 g). The mixture fractions were combined and concentrated under vacuum (480 g). A white insoluble solid formed by dilution with toluene (300 ml) prior to loading on Biotage 150 L was removed by vacuum filtration. The material soluble in toluene was purified via Biotage 150M HP-Sphere (SiO$_2$ 2.5 kg (pretreated with 1% TEA); sample loading with toluene; eluents: 2:1 n-heptane/EtOAc (26 L) w/1% TEA, 1:1 (25 L) w/1% TEA, 1:4 (34 L) w/1% TEA). The column was monitored by TLC (1:1 n-heptane/EtOAc). The combined clean product fractions were concentrated under vacuum to give additional Compound (206) as off white solid foam (165.5 g. Total 662.2+165.5 g=827.7 g, 930 mmol, 1.03 wt, 67% yield).

$^1$H NMR (400 MHz, CHLOROFORM-d) δ (ppm): 8.47 (s, 1H), 8.39 (s, 1H), 8.20 (s, 1H), 8.01 (s, 1H), 7.38-7.31 (m, 5H), 7.27-7.19 (m, 6H), 7.14-7.06 (m, 3H), 6.93-6.87 (m, 2H), 6.76 (d, J=8.6 Hz, 4H), 6.26 (dd, J=2.0, 16.0 Hz, 1H), 6.15 (dd, J=2.7, 17.2 Hz, 1H), 5.86 (dd, J=4.7, 15.2 Hz, 1H), 5.80 (dd, J=4.7, 15.2 Hz, 1H), 5.51 (ddd, J=2.7, 4.3, 52.8 Hz, 1H), 5.31 (ddd, J=2.0, 4.3, 52.8 Hz, 1H), 4.87 (d, J=4.7 Hz, 2H), 4.85-4.81 (m, 1H), 4.79 (d, J=4.3 Hz, 2H), 4.71-4.59 (m, 1H), 4.20-4.13 (m, 2H), 4.06 (dd, J=2.7, 11.3 Hz, 1H), 3.90 (dd, J=2.7, 11.7 Hz, 1H), 3.77 (s, 6H), 3.52 (dd, J=3.1, 10.9 Hz, 1H), 3.18 (dd, J=3.9, 10.9 Hz, 1H), 0.92 (s, 9H), 0.84 (s, 9H), 0.10 (s, 3H), 0.09 (s, 6H), 0.07 (s, 3H).

Stage 5-6

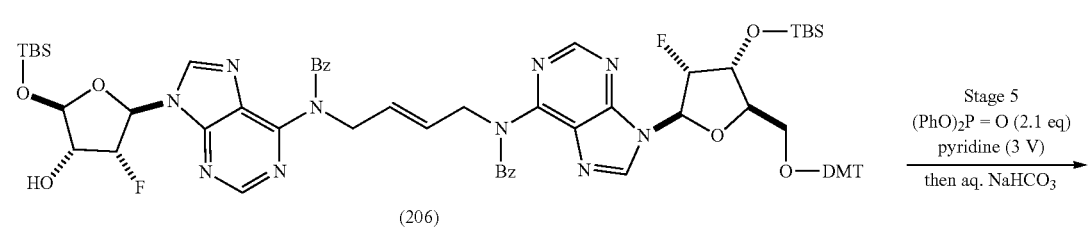

[Chem. 20]

Stage 5
(PhO)$_2$P=O (2.1 eq)
pyridine (3 V)
then aq. NaHCO$_3$

-continued

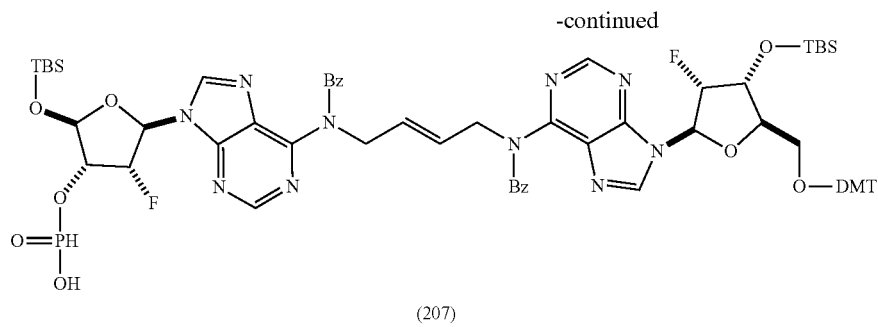

(207)

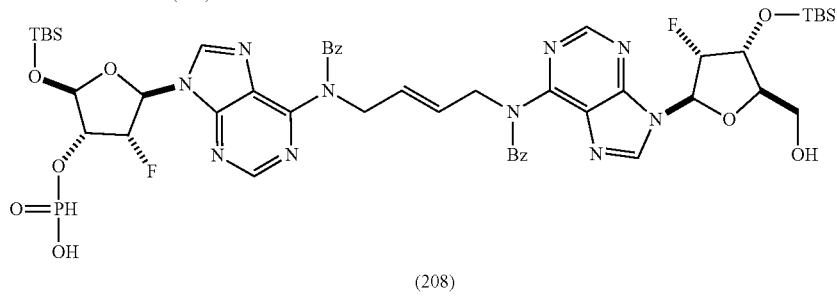

(208)

To a solution of Compound (206) (410.7 g, 309 mmol, 1 wt, 1 vol, 1 eq.) in pyridine (1.23 L, 1.21 kg, 15.2 mol, 2.9 wt, 3.0 vol, 49 eq.) was added diphenyl phosphite (90 ml, 109 g, 0.46 mol, 0.26 wt, 0.22 vol, 1.5 eq.). The reaction was stirred at rt and was monitored by LCMS. After 2 h (80% conversion) an additional diphenyl phosphite (29.9 ml, 36.2 g, 155 mmol, 0.088 wt, 0.073 vol, 0.50 eq.) was added. After an additional 1 h an extra diphenyl phosphite (6.0 ml, 7.2 g, 31 mmol, 0.018 wt, 0.015 vol, 0.10 eq.) was added and the reaction was continued for an additional 0.5 h (98% conversion). The reaction mixture was added to a mixture of saturated NaHCO₃ (9 wt % solution in water; 2.1 L, 5 vol) and water (1.0 mL, 2.5 vol) while keeping T-internal 4.7 to 12° C. The reactor was rinsed with a small volume of EtOAc. Stirring was continued at rt for 30 minutes and monitored the reaction by LCMS (100% conversion). The reaction mixture was extracted twice with 1:1 mixture of EtOAc and MTBE (2×8.2 L, 2×20 vol). The combined organic layers were washed with water (4.1 L, 10 vol), concentrated in vacuo and azetroped with toluene (3×4.1 L, 3×10 vol; continuous feeding) for removal of pyridine to give Compound (207) (0.55 eq. pyridine remained).

Stage 6

The crude Compound (207) was dissolved in dichloromethane (3.08 L, 4.07 kg, 9.9 wt, 7.5 vol) at ambient temperature. Water (55.7 ml, 0.136 vol, 10 eq.) was added followed by a solution of dichloroacetic acid (77 ml, 120 g, 0.93 mol, 0.29 wt, 0.19 vol, 3.0 eq.) in DCM (3.08 L, 7.5 vol) while keeping the internal T below 25° C. (Turned into an orange solution). After 30 min, triethylsilane (Et₃SiH; 494 ml, 359 g, 3.09 mol, 0.875 wt, 1.20 vol, 10.0 eq.) (T-internal went from 18.2° C. to 17° C.) was added and stirring was continued for 20 min. Triethylamine (431 ml, 313 g, 3.09 mol, 0.762 wt, 1.05 vol, 10.0 eq.) was added (T-internal went from 17.8° C. to 22° C.). The mixture was concentrated to 1.55 kg (3.8 wt), redissolved in EtOAc (6.2 L, 5.5 kg, 14 wt, 15 vol), sequentially washed with: (1) water (1.0 L, 2.5 vol) and saturated NaHCO₃ (9 wt % solution in water, 0.82 L, 2.0 vol). The crude product EtOAc solution was stored at −20° C. overnight; 0.82 L, 2.0 vol) and in next day, the solution was concentrated in vacuo at 25° C. The crude mixture thus obtained (654 g) was triturated with: (1) n-heptane (3.01 L, 7.5 vol), (2) a mixture of n-heptane (2.46 L, 6.0 vol) and toluene (0.82 L, 2.0 vol). The solution part (supernatant) was decanted off and the solid remained at the bottom was dissolved in acetonitrile (4.1 L, 10 vol). The mixture was concentrated in vacuo at 25° C. and azeotroped with acetonitrile twice to give Compound (208). The product was used for the subsequent stage without purification (theoretical 100% yield assumed).

Stage 7

[Chem. 21]

Stage 7a

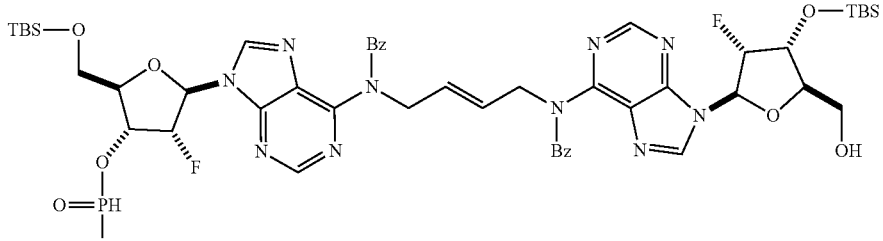

(208)

-continued

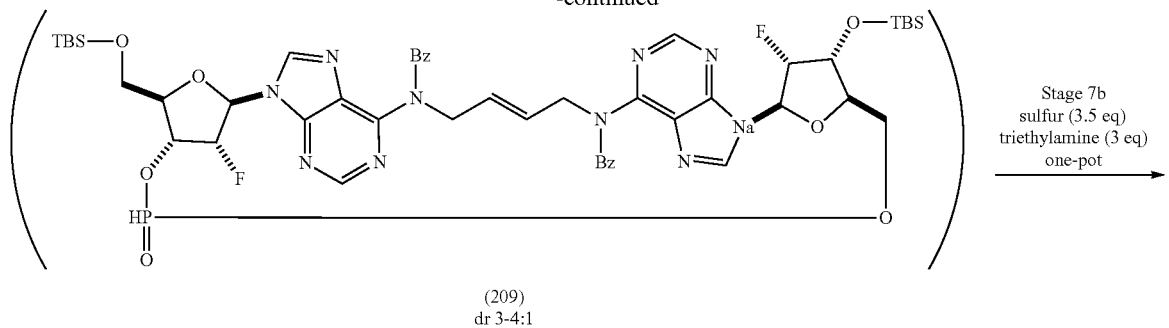

(209)
dr 3-4:1

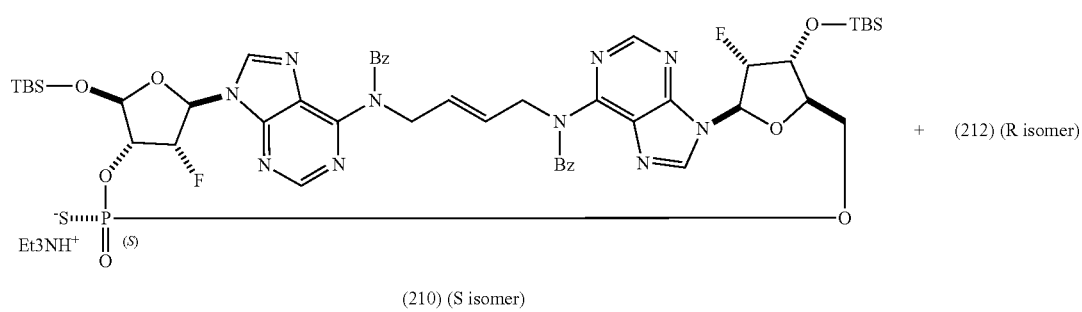

(210) (S isomer)

+ (212) (R isomer)

Stage 7a

Compound (208) (337 g, 309 mmol, 1 wt, 1 vol, 1 eq.) was dissolved in anhydrous pyridine (13.5 L, 13.2 kg, 39 wt, 40 vol) at rt. Triethylamine (129 ml, 927 mmol, 94 g, 0.28 wt, 0.38 vol, 3.0 eq.) was added followed by 2-chloro-5,5-dimethyl-1,3,2-dioxaphosphinane 2-oxide (DMOCP; 103 g, 556 mmol, 0.31 wt, 1.80 eq.). The resultant mixture was stirred at ambient temperature for 30 minutes and monitored by LCMS (100% conversion) to generate Compound (209).

Stage 7b TEA (129 ml, 927 mmol, 94 g, 0.28 wt, 0.38 vol, 3.0 eq.), water (100 ml, 5.56 mol, 0.30 wt, 0.30 wt, 18 eq) and sulfur (34.7 g, 1.08 mol, 0.10 wt, 3.5 eq) were added to the above mixture of Compound (209). After 90 minutes (100% conversion), NaHCO$_3$ (9 wt % solution in water; 3.37 L, 10 vol) was added while keeping T-internal below 30° C. (16.6° C. to 27° C.). The resultant mixture was filtered for removal of salts. The filtrate was concentrated the mixture in vacuo, diluted with MTBE (5.1 L, 15 vol), and wash twice with NaCl (30 wt % solution in water; 2×1.35 L, 2×4 vol). Insoluble solids were filtered off and the filtrate was concentrated in vacuo and azeotroped with toluene (4.0 L, 12 vol). The resulting solid was removed by filtration and the crude mixture was dissolved in toluene and purified via Biotage 150 L KP-Sil (SiO$_2$ 5 kg; pretreated with n-heptane/EtOAc/TEA (1.5/1.5/0.03 CV); eluted with: EtOAc/TEA (3/0.03 CV), EtOAc/MeOH/TEA (4/0.2/0.04 CV), EtOAC/MeOH/TEA (2/0.2/0.02CV). The column was monitored by TLC (EtOAC/MeOH/TEA=9/1/0.1). Fractions containing the Sp isomer were combined and concentrated under vacuum to give Compound (210) as light pink foam solid (Sp isomer; 154 g, 128 mmol, 0.46 wt, 41.3% yield). Fractions containing the Rp isomer were combined and concentrated under vacuum to give Compound (212) as light pink foam solid (Rp isomer; 64 g, 53 mmol, 0.19 wt, 17% yield).

Compound (210) (Sp isomer):

$^1$H NMR (400 MHz, CHLOROFORM-d) δ (ppm): 8.51 (s, 1H), 8.50 (s, 1H), 8.22 (s, 1H), 8.14 (s, 1H), 7.49-7.44 (m, 2H), 7.38-7.27 (m, 4H), 7.25-7.21 (m, 2H), 7.14 (t, J=7.1 Hz, 2H), 6.44 (dd, J=2.5, 13.9 Hz, 1H), 6.18 (d, J=15.2 Hz, 1H), 5.78 (td, J=6.3, 15.6 Hz, 1H), 5.69 (td, J=4.7, 15.6 Hz, 1H), 5.56 (dd, J=3.9, 50.8 Hz, 1H), 5.20-5.06 (m, 1H), 4.95-4.79 (m, 4H), 4.69 (dd, J=4.3, 16.0 Hz, 1H), 4.54-4.38 (m, 3H), 4.35 (d, J=5.5 Hz, 1H), 4.32-4.29 (m, 1H), 4.05 (dd, J=1.6, 11.7 Hz, 1H), 3.91 (dd, J=3.1, 11.7 Hz, 1H), 3.14-3.06 (m, 6H), 1.30 (t, J=7.4 Hz, 9H), 0.91 (s, 9H), 0.90 (s, 9H), 0.12 (s, 3H), 0.08 (s, 3H), 0.06 (s, 3H), 0.05 (s, 3H)

Compound (212) (Rp isomer):

$^1$H NMR (400 MHz, CHLOROFORM-d) δ(ppm): 8.54 (s, 1H), 8.38 (s, 1H), 8.33 (s, 1H), 8.01 (s, 1H), 7.39-7.09 (m, 10H), 6.39 (dd, J=2.3, 14.1 Hz, 1H), 6.13 (d, J=17.2 Hz, 1H), 5.72 (d, J=3.1 Hz, 2H), 5.68 (dd, J=4.3, 51.2 Hz, 1H), 5.43-5.29 (m, 1H), 5.10-4.96 (m, 3H), 4.90-4.83 (m, 2H), 4.78-4.72 (m, 1H), 4.52 (ddd, J=3.9, 6.6, 17.2 Hz, 1H), 4.44-4.35 (m, 2H), 4.31-4.26 (m, 1H), 4.20-4.12 (m, 2H), 3.87 (dd, J=3.5, 11.7 Hz, 1H), 3.79-3.77 (m, 1H), 3.15-3.09 (m, 6H), 1.33 (t, J=7.4 Hz, 9H), 0.94 (s, 9H), 0.89 (s, 9H), 0.13 (s, 3H), 0.12 (s, 3H), 0.10 (s, 3H), 0.09 (s, 3H).

Stage 8

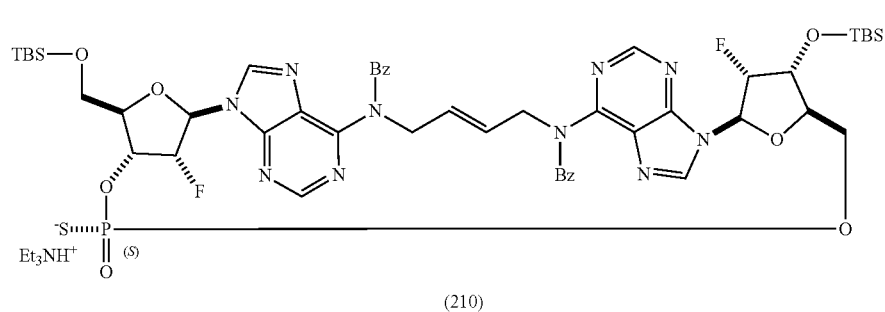

(210)

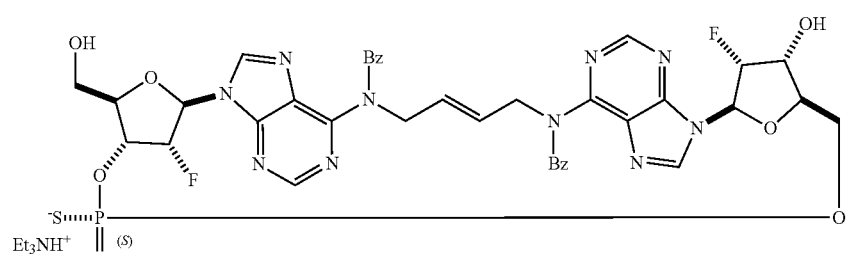

(211)

Compound (210) (221 g, 183 mmol, 1 wt, 1 vol, 1 eq) was dissolved in a mixture of pyridine (530 ml, 6.56 mol, 519 g, 2.3 wt, 2.4 vol) and TEA (2.65 L, 19.0 mol, 1.93 kg, 8.7 wt, 12 vol, 104 eq.). Triethylamine trihydrofluoride (264 ml, 1.62 mol, 262 g, 1.2 wt, 1.2 vol, 8.9 eq. as complex, 27 eq. HF) was added and the mixture was stirred at rt while the conversion was monitored by LCMS. After 3 h (97% conversion), methoxytrimethylsilane (TMSOMe; 1.40 L, 10.2 mol, 1.06 kg, 4.8 wt, 6.3 vol, 55 eq.) was added and stirring was continued for 30 minutes. A sticky solid coated the reactor. The solution part (supernatant) was decanted off. The solid was triturated twice with toluene (2×2.2 L, 2×10 vol; supernatant decanted off). The crude solid remained in the reactor was dissolved in dichloromethane (2.2 L, 10 vol) and washed with NH$_4$Cl (28 wt % solution in water; 2.2 L, 10 vol). The aqueous layer was back-extracted with dichloromethane (2.2 L, 10 vol). The combined organic layers were washed with a mixture of NaCl (36 wt % solution in water; 1.1 L, 5 vol) and water (1.1 L, 5 vol), and then concentrated under vacuum to give Compound (211) as tan dry foam (152 g, 155 mmol, 0.70 wt, 85% yield). The crude product was taken onto the next step without purification.

Stage 9

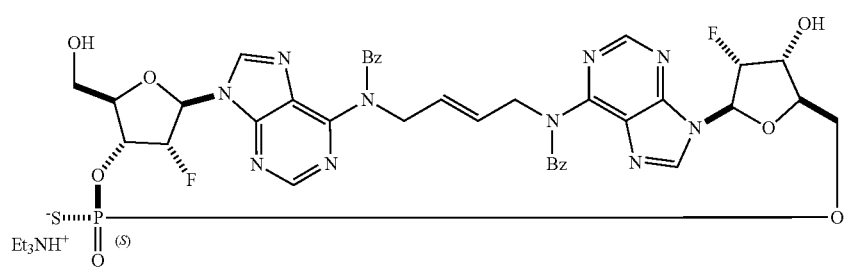

(211)

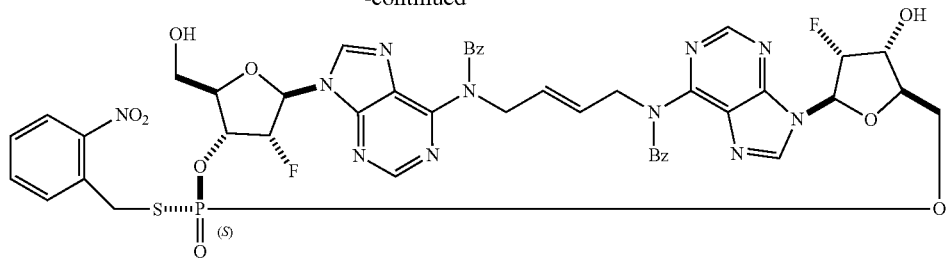

(212)

Compound (211) (150 g, 153 mmol, 1 wt, 1 vol, 1 eq.) was azeotroped with acetonitrile (4 L, 27 vol) and then re-dissolved in acetonitrile (1.05 L, 0.83 kg, 5.5 wt, 7.0 vol) at rt. 2-Nitrobenzyl bromide (44.4 g, 205 mmol, 0.30 wt, 1.34 eq) was added at rt and the reaction was monitored by LCMS. After 23 h (100% conversion), EtOAc (1.50 L, 10 vol), NH$_4$Cl (28 wt % solution in water; 300 ml, 2 vol) and water (300 ml, 2 vol) were added (pH=6) and the resultant mixture was partially concentrated under vacuum at 25° C. to a weight of 1.11 kg. EtOAc (2.25 L, 15 vol) was added and the mixture was stirred for 5 minutes. The two layers were separated. The aqueous layer was extracted with ethyl acetate (750 ml, 5 vol). The combined organic layers were sequentially washed with: (1) a mixture of NaCl (36 wt % solution in water; 300 ml, 2 vol) and water (300 ml, 2 vol) and (2) water (600 ml, 4 vol). The organic layer was then concentrated under vacuum and azeotroped with n-heptane (1.50 L, 10 vol). MTBE (0.95 L, 6.3 vol) was added to the crude solid and the mixture was heated at 40° C. The mixture was diluted with EtOAc (300 ml, 2 vol) and slowly cooled to 0° C. The dense solid was allowed to settle and the supernatant was pumped off through a filter frit tube. The solid was rinsed twice with MTBE (2×300 ml, 2×2 vol; supernatant pumped off through the filter frit tube each time) and dried under vacuum at 40° C. overnight to give Compound (212) as pale yellow solid (156 g). The filtrate was concentrated under vacuum yielding a brown oil (17.8 g), which was subjected to purification via Biotage Snap-Ultra 340 g (eluents: 0 to 5% MeOH in EtOAc) to give additional Compound (212) as pale yellow solid (5.8 g). Total 156 g+5.8 g=161.8 g (net 152 mmol, 95% pure, 99% yield) $^1$H NMR (400 MHz, CHLOROFORM-d) δ (ppm); 8.46 (s, 1H), 8.15 (s, 1H), 8.10 (s, 1H), 8.09-8.06 (m, 1H), 7.89 (s, 1H), 7.54-7.51 (m, 1H), 7.49-7.45 (m, 4H), 7.37-7.28 (m, 3H), 7.24-7.19 (m, 3H), 7.16-7.11 (m, 2H), 6.22 (d, J=16.8 Hz, 1H), 6.14 (dd, J=2.7, 17.2 Hz, 1H), 5.83-5.61 (m, 3H), 5.60-5.48 (m, 1H), 5.07 (dd, J=3.5, 51.6 Hz, 1H), 5.06-4.96 (m, 1H), 4.79 (dd, J=4.9, 15.8 Hz, 1H), 4.69 (d, J=5.9 Hz, 2H), 4.67-4.56 (m, 1H), 4.48-4.40 (m, 3H), 4.37-4.30 (m, 1H), 4.27 (d, J=5.9 Hz, 2H), 4.19-4.13 (m, 1H), 3.93-3.85 (m, 1H), 3.85-3.78 (m, 1H)

Stage 10-11

[Chem. 24]

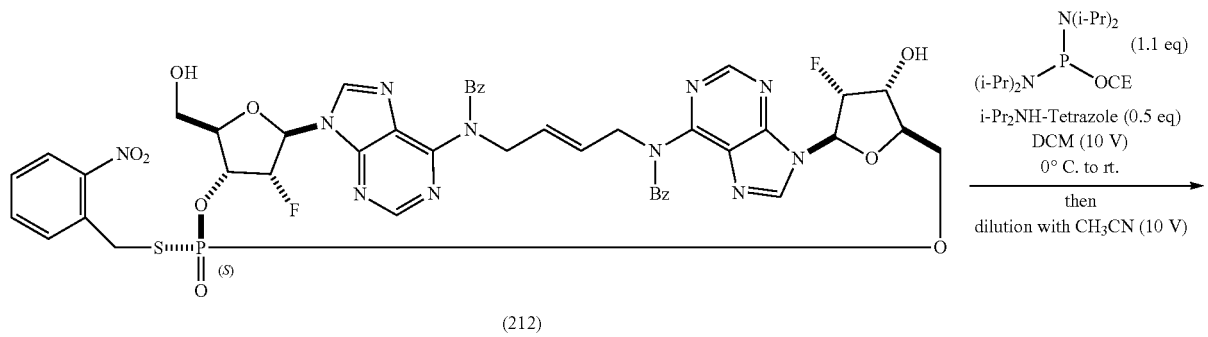

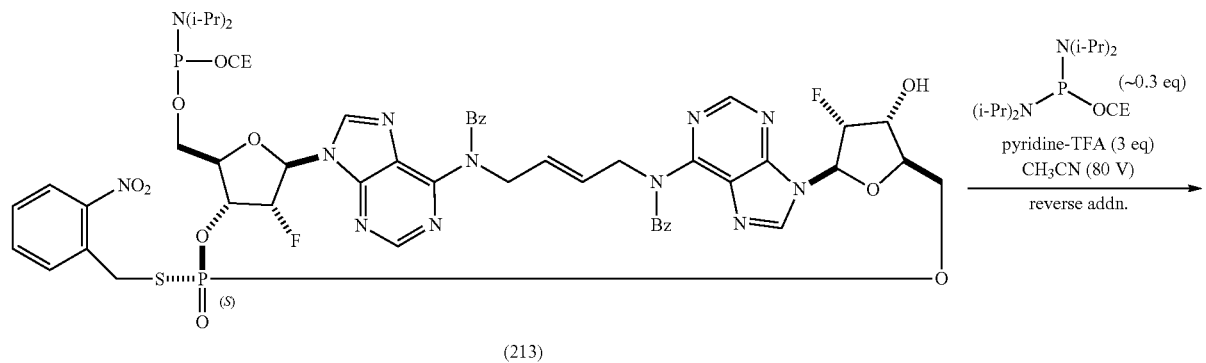

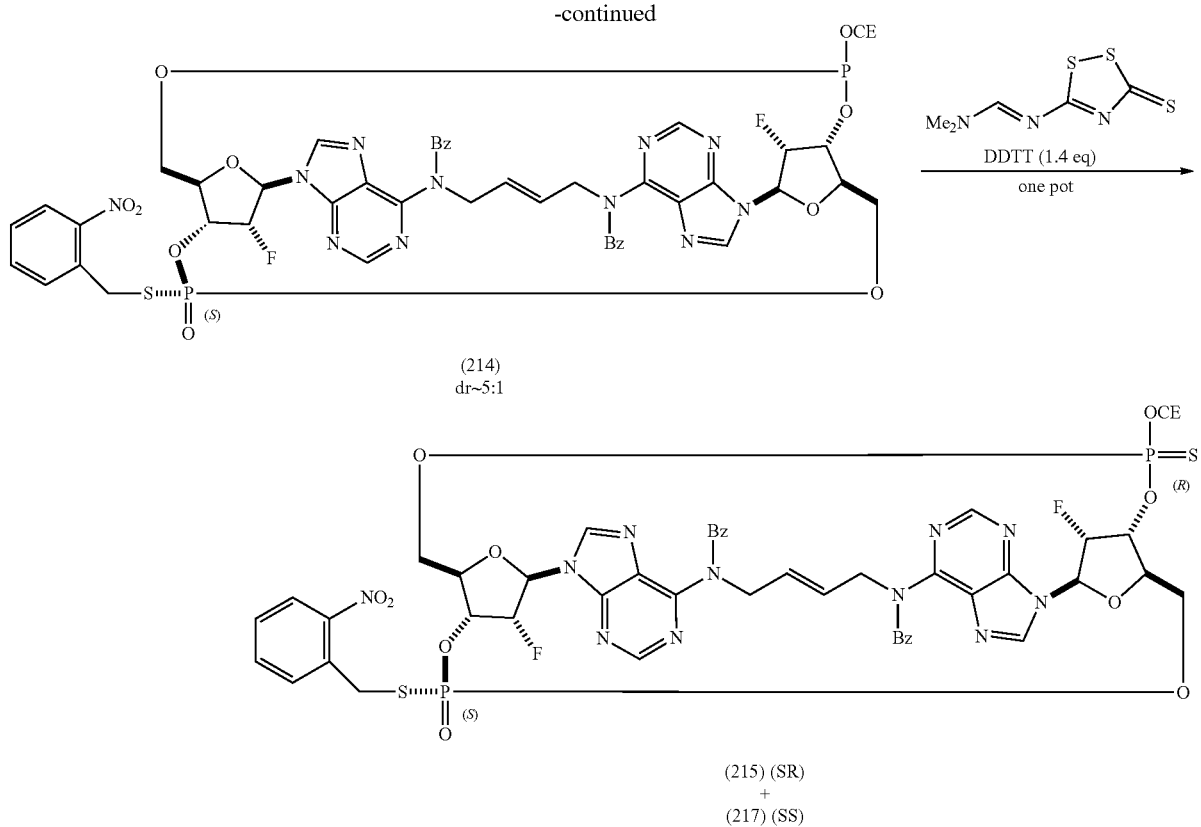

(214)
dr~5:1

(215) (SR)
+
(217) (SS)

Stage 10

Compound (212) (95% pure, net 73.2 g, 72.3 mmol, 1 wt, 1 vol, 1 eq.) and 2-cyanoethyl N,N,N',N'-tetraisopropylphosphorodiamidite (25.3 ml, 79.5 mmol, 0.33 wt, 0.35 vol, 1.10 eq.) were azeotroped with anhydrous acetonitrile three times (3×2 L), re-dissolved in dichloromethane (0.73 L, 10 vol) and cooled to 0-5° C. Diisopropylammonium tetrazolide (6.19 g, 36.1 mmol, 0.085 wt, 0.50 eq.) was added. The resulting reaction mixture was stirred at 0° C. for 10 h, warmed to 10° C. over 2 h, held at 10° C. for 10 h and warmed up to rt over 2 h. The reaction was monitored by LCMS and TLC (EtOAc with 0.5% TEA). After 18 h, anhydrous acetonitrile (0.73 L, 10 vol) was added and the mixture was stored at −20° C. over 3 days.

Stage 11a

The mixture from Stage 10 was warmed to ambient temperature and added via a dropping funnel in portions (100 mL every 30 minutes, over 9 h) into a mixture of pyridine trifluoroacetate salt (azetroped in advance with pyridine twice; 41.9 g, 217 mmol, 0.57 wt, 3.0 eq.) and acetonitrile (5.85 L, 80 vol). The reaction was monitored by LCMS. After 13 h, a solution of 2-cyanoethyl N,N,N',N'-tetraisopropylphosphorodiamidite (5.8 mL, 18 mmol, 0.25 eq.) in acetonitrile (24 mL) was added over 4 h. Amount of the additional reagent was determined based on the remaining Compound (212) (~30% based on LCMS). More conversion of the diol was observed after 6 h.

Stage 11b ((Dimethylaminomethylidene)amino)-3H-1,2,4-dithiazoline-3-thione (DDTT; 20.8 g, 101 mmol, 0.28 wt, 1.4 eq.) was added and stirring was continued for 1 h. The reaction mixture was partially concentrated to ~800 mL and diluted with MTBE (1.46 L, 20 vol), NaHCO$_3$ (9 wt % solution in water; 1.1 L, 15 vol) and water (0.37 L, 5 vol). pH=8. The layers were separated and the aqueous layer was extracted with a mixture of MTBE (1.46 L, 20 vol) and EtOAc (1.10 L, 15 vol). The combined organic layers were washed twice with 30% aq. NaCl (2×0.73 L, 2×10 vol), concentrated under vacuum at 35° C. and azeotroped with toluene (1.46 L, 20 vol). LCMS and TLC (EtOAc) indicated Compound (215) (SpRp, desired): Compound (217) (SpSp)=5:1

The crude product was purified via Biotage 150M KP-Sil, (SiO$_2$ 2.5 kg; eluents: EtOAc/n-heptane: 2:1 (4 CV), 3:1 (2.5 CV), 4:1 (2.5 CV), 100% EA (3 CV), 5-10% MeOH in EA 4 CV) to give Compound (215) (36 g, 31.5 mmol, 44% yield).

Compound (215) (SpRp): $^1$H NMR (400 MHz, CHLOROFORM-d) δ(ppm): 8.59 (s, 1H), 8.10 (s, 1H), 8.03-7.99 (m, 1H), 7.91 (s, 1H), 7.56-7.53 (m, 2H), 7.49-7.40 (m, 5H), 7.35-7.28 (m, 2H), 7.24-7.16 (m, 4H), 6.92 (s, 1H), 6.29 (d, J=14.9 Hz, 1H), 6.08 (d, J=20.7 Hz, 1H), 5.97-5.83 (m, 1H), 5.76 (td, J=4.7, 15.6 Hz, 1H), 5.61-5.51 (m, 2H), 5.40 (d, J=4.3 Hz, 1H), 5.29-5.17 (m, 1H), 4.91 (dd, J=7.4, 14.9 Hz, 1H), 4.86-4.75 (m, 3H), 4.63 (dd, J=3.7, 9.2 Hz, 1H), 4.58-4.43 (m, 5H), 4.34-4.19 (m, 4H), 2.79 (td, J=5.9, 16.8 Hz, 1H), 2.66 (td, J=6.3, 16.8 Hz, 1H).

Compound (217) (SpSp)$^1$H NMR (400 MHz, CHLOROFORM-d) δ (ppm): 8.11 (s, 1H), 8.03 (d, J=8.2 Hz, 1H), 7.94 (s, 1H), 7.90 (s, 1H), 7.61 (s, 1H), 7.56-7.40 (m, 7H), 7.33-7.28 (m, 2H), 7.23-7.17 (m, 4H), 6.22 (d, J=17.6 Hz, 1H), 6.15 (d, J=18.8 Hz, 1H), 5.85 (dd, J=3.5, 51.2 Hz, 1H), 5.75-5.45 (m, 5H), 4.95-4.23 (m, 14H), 2.82 (t, J=6.1 Hz, 2H).

Stage 12

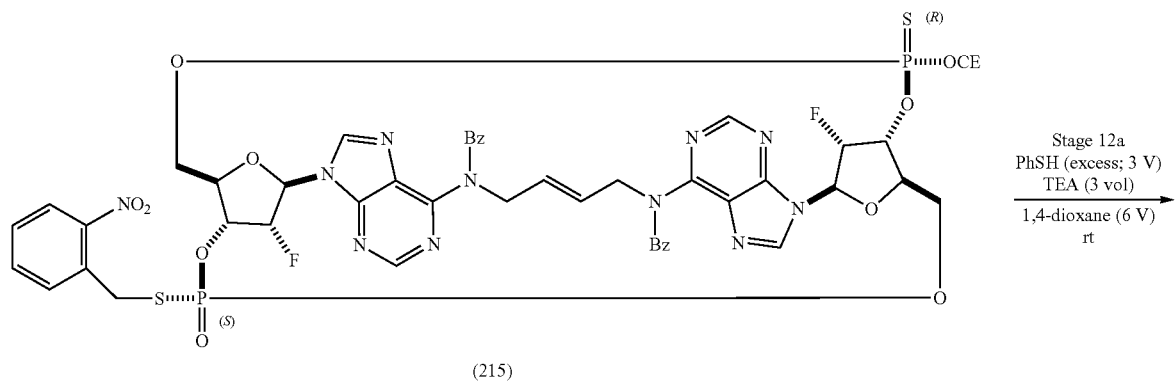

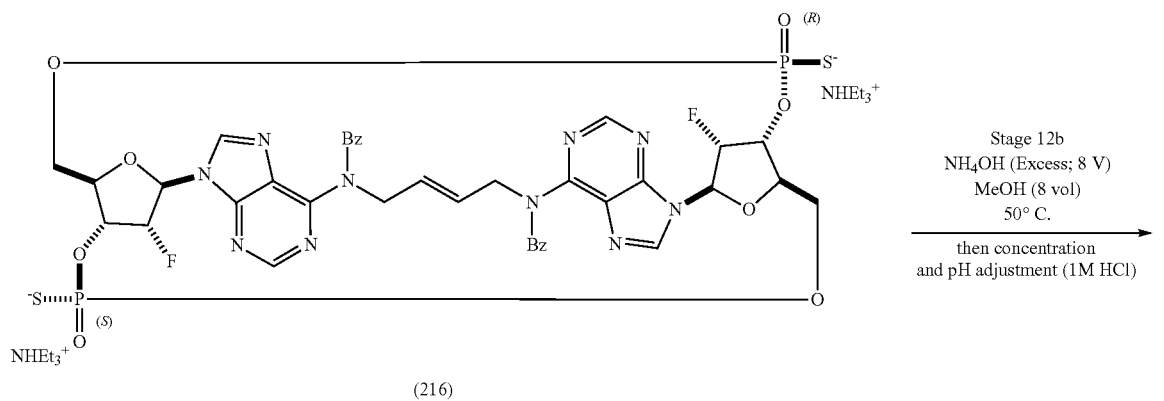

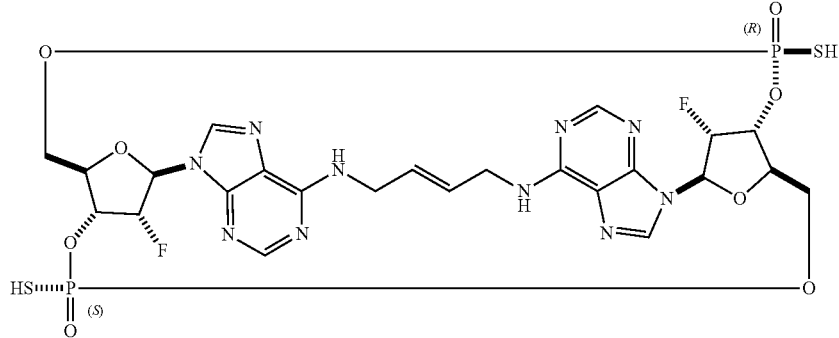

Compound (I)

Compound (215) (71.6 g, 62.6 mmol, 1 wt, 1 vol, 1 eq.) was dissolved in 1,4-dioxane (0.43 L, 6 vol). Thiophenol (215 ml, 2.09 mol, 230 g, 3.2 wt, 3 vol, >30 eq.) was added followed by triethylamine (215 ml, 1.54 mol, 156 g, 2.2 wt, 3 vol). Some exotherm was observed (T-internal increased by ~7° C.), therefore, water/ice bath was used to cool and control T-internal below 27° C. The reaction was monitored by LCMS. After 2 h, MeOH (0.57 L, 8 vol) and NH$_4$OH (28 wt %; 15 mol, 0.57 L, 8 vol, >200 eq.) were added. The resulting mixture was heated at 50° C. for 5 h, cooled to rt and stirred overnight. After 14 h, water (0.72 L, 10 vol) was added (no solid observed) and the mixture was extracted three times with 1:1 (v/v) mixture of n-heptane and toluene (3×0.86 L, 3×12 vol), followed by with toluene (0.57 L, 8 vol). The aqueous layer was concentrated in vacuo at 40-50° C. and diluted with water (1.07 L, 15 vol). The resulting slurry was kept overnight at rt. The resulting solid was filtered off, rinsing with water (0.36 L, 5 vol). The filtrate was still cloudy and filtered through celite and a Kuno filter. Cloudiness was still present. HCl (1.0 M solution in water; 132 ml, 132 mmol, 2.1 eq.) was added over 1 h and pH was checked (pH <2). Stirring was continued at rt for 1 h and the mixture was filtered. The filter cake was rinsed with water (8×0.20 L), dried in a vacuum oven at 35° C. for 2 days and with no heat for 1 day to give Compound (I) as pale orange solid (44.88 g, 60.1 mmol, 0.63 wt, 96% yield).

Stage 13

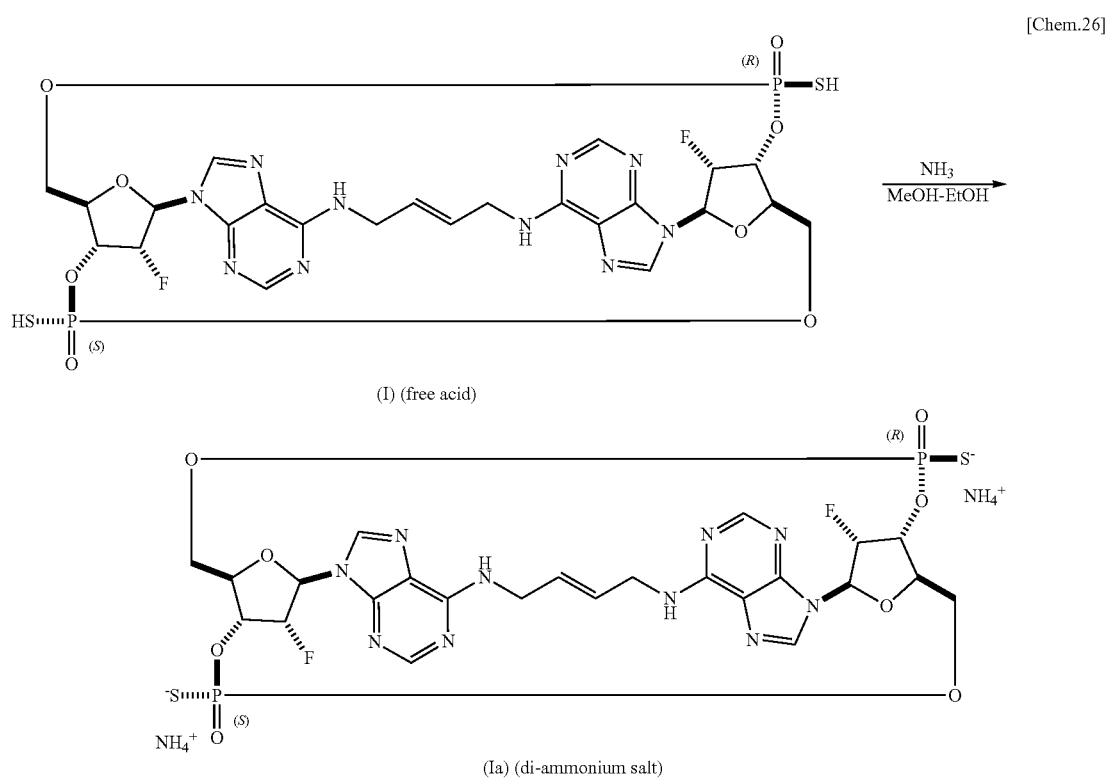

To the free acid Compound (I) (22.42 g, 30.03 mmol, 1 wt, 1 vol, 1 eq.) was added ammonia (2.0M solution in MeOH; 220 ml, 440 mmol, 10 vol, 15 eq.). EtOH (55 ml, 2.5 vol) was added and the resulting solution was filtered through a Kuno filter (0.45 micron; PTFE), rising with 1:1 (v/v) mixture of MeOH and EtOH (90 mL, 4 vol). The filtrate was concentrate in vacuo at 30° C. yielding an off white solid, which was dried at rt overnight, grinded with a spatular (easy to break) and dried further in vacuum at rt. The isolated solid was then suspended in toluene (250 ml) and stirred at rt for 30 minutes. The solid was then collected by vacuum filtration and rinsed with toluene twice (2×50 ml). The solid was then dried under vacuum in a vacuum oven to give 22.4 g of Compound (1a) (Compound (I) di-ammonium salt).

Recrystallization:

Compound (1a) (Compound (I) di-ammonium salt) (22.14 g, 28.36 mmol, 1 wt, 1 vol, 1 eq.) was dissolved in a mixture of water (664 ml, 30 vol) and ammonium hydroxide (28 wt %; 2.5 ml, 18 mmol, 0.63 eq.) (pH=9-10) and extracted with toluene three times (3×300 ml, 3×14 vol), EtOAc three times (3×200 ml, 3×9 vol) and toluene three times (3×300 ml, 3×14 vol). The resulting aqueous layer was treated with HCl (1.0M solution in water; 90 ml, 90 mmol, 3.2 eq.) over a period of 3.5 hours (pH 2 or less). The mixture stirred for 30 minutes and then the solid precipitate was collected by vacuum filtration. The filter cake was washed with water three times (3×200 ml, 3×9 vol) and dried in vacuo overnight. Ammonia (2.0M solution in MeOH; 250 ml, 500 mmol, 17.6 eq.) and ethanol (100 ml) were added to the solid and the resulting mixture was concentrated in vacuo until crystals appeared (~100 ml), at which time concentration was stopped and the mixture was stirred for 20 minutes. Ethanol (45 mL) was added and the mixture was partially concentrated (45 mL removed). The same operation was repeated two more times, and then the mixture was cooled to 0° C. and stirred for 3.5 h. The white solid was collected by vacuum filtration and washed with cold ethanol (20 ml) followed by ethyl acetate (2×50 mL). The white solid was dried under vacuum at rt for 3 days to give Compound (1a) (Compound (I) di-ammonium salt) as white solid (16.6 g, 21.3 mmol, 0.75 wt, 75% yield). The filtrate was concentrated under vacuum and dried under vacuum at rt for 3 days to give Compound (1a) (Compound (I) di-ammonium salt) as off white solid (4.16 g, 5.3 mmol, 18% yield).

Analysis Example 1.2—$^1$H NMR Analysis of Compound (I) ammonium salt

An $^1$H NMR spectrograph of Compound (I) ammonium salt is shown in FIG. 1. The resulting spectrum was:

$^1$H-NMR Spectrum (400 MHz, DMSO-$d_6$, $\delta_H$ 2.49 ppm, 80° C.)

δ(ppm): 8.59 (1H, br s), 8.36 (1H, br s), 8.14 (1H, s), 8.13 (1H, s), 6.29 (1H, m), 6.26 (1H, m), 5.78 (1H, m), 5.76 (2H, s), 5.22 (1H, m), 4.53-4.68 (2H, m), 4.38 (1H, m), 4.28 (1H, m), 4.21-4.24 (2H, m), 3.78 (1H, dd, J=12, 4 Hz), 3.70 (1H, dd, J=13, 5 Hz), 3.05-3.13 (4H, m).

Analysis Example 1.3—X-Ray Analysis of Compound (I) ammonium salt About 2 mg of Compound (I) ammonium salt was dissolved in 600 μL of water. 120 μL of this solution was put in another glass vial and then this vial was stored in fixed container with 3 mL of MeCN at room temperature for 1 week. This is the H$_2$O/MeCN vapor diffusion method of sample preparation.

A colorless block single crystal (0.1×0.1×0.1 mm) found in crystallization solution was dispersed in liquid Parabar 10312 and was mounted on a Dual-Thickness Micro-Mounts™ (MiTeGen). Diffraction data was collected at −160° C. on XtaLAB PRO P200 MM007HF (Rigaku) with ω axis oscillation method using multi-layer mirror monochromated Cu-Kα radiation.

FIG. 2A shows an ORTEP figure of a crystal of Compound (I) ammonium salt, where two molecules are present in an asymmetric unit, along with a number of disordered water molecules. FIG. 2B shows an ORTEP figure of one of the two molecules in the asymmetric unit from FIG. 2A. FIG. 2C shows an ORTEP figure of the other molecule in the asymmetric unit from FIG. 2A.

The crystal structure of Compound (I) ammonium salt was solved with a final R-factor of 0.1354. The Flack parameter was nearly zero (0.083 (17)), indicating that the absolute configuration of Compound (I) ammonium salt is (R, S). The crystal structure analysis also indicated that several water molecules were present in the large channel of Compound (I) ammonium salt, which indicated that water molecules were able to easily slip out from the channel. The analysis also confirmed that the conformations of both crystallographically independent molecules in the asymmetric unit were almost the same.

TABLE 3

| Further parameters of the X-ray analysis are shown below: | |
|---|---|
| Temperature | 113K |
| Wavelength | 1.54184 Å |
| Crystal system, Space group | Monoclinic, P2$_1$ |
| Lattice parameter | a = 8.1584(3) Å |
|  | b = 35.451(2) Å |
|  | c = 15.9146(6) Å |
|  | β = 91.313(3) ° |
| Volume | 4601.7(4) Å$^3$ |
| Z value, calculated density | 4, 1.127 g/cm$^3$ |
| Crystal size | 0.1 × 0.1 × 0.1 mm |
| Total number of reflections/ number of unique reflections | 52006/17198 [R(intensity) = 0.0876] |
| Completeness | 92.2% |
| Phase determination | Direct methods (SHELXT Version 2014/5) |
| Refinement method | Full-matrix least-squares on F$^2$ (SHELXL Version 2014/7) |
| Data/parameter | 17198/1116 |
| Goodness of fit indicator | 1.545 |
| Residuals: R(I > 2σ(I)) | 0.1354 |
| Residuals: Rw | 0.3886 |
| Flack parameter | 0.083(17) |
| Maximum and Minimum peak difference | 1.17 and −0.88 e$^-$/Å$^3$ |

Example 1

Preparation of Crystal (Form 1) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To a suspension of Compound (I)(138.5 mg) in isopropyl acetate (2.769 mL) was added a mixture of 28% ammonia aqueous solution (62xL), isopropyl acetate (0.693 mL) and 2-propanol (0.138 mL), and the resulting slurry was stirred at room temperature overnight. The precipitates were cropped by filtration, rinsed with isopropyl acetate (0.8 mL), and the solid obtained was dried under reduced pressure at room temperature for 2 hours to give the titled crystal (126.8 mg). The titled crystal was identified as a hydrate.

Example 1-2

Preparation of Crystal (Form 1) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To a suspension of Compound (I) (900 mg) in isopropyl acetate (18.0 mL) was added a mixture of 28% ammonia aqueous solution (400 μL), isopropyl acetate (4.5 mL) and 2-propanol (0.90 mL), and the resulting slurry was stirred at room temperature overnight. The precipitates were cropped by filtration, rinsed with isopropyl acetate (4.5 mL), and the solid obtained was dried under reduced pressure at room temperature for 5 hours and successively absorbed moisture by keeping under 50% relative humidity at room temperature overnight to give the titled crystal (942 mg). The titled crystal was identified as a hydrate.

Example 2

Preparation of Crystal (Form 2) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To Compound (I) (143.6 mg) were added 28% ammonia aqueous solution (1.724 mL) and ethanol (1.718 mL), and the resulting solution was concentrated down to about 0.86 mL under reduced pressure at 40° C. To the residue was added ethanol (1 mL), and the solution was concentrated down to about 0.86 mL under reduced pressure at 40° C. To the residue was added ethanol (1 mL), and the resulting solution was concentrated down to 0.89 g under reduced pressure at 40° C. The residue solution was stirred at room temperature for 0.5 hours and the precipitates fell out of the solution. To the slurry was gradually added isopropyl acetate (1.2 mL) dropwise for 10 minutes, and the resulting slurry was stirred at room temperature overnight. The precipitates were cropped by filtration and the solid obtained was dried under reduced pressure at room temperature for 3.3 hours to give the titled crystal (144 mg). The titled crystal was identified as a hydrate.

Example 3

Preparation of Crystal (Form 3) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt Approximately 10 mg of crystal (Form 1) of Compound (I) di-ammonium salt was placed in a desiccator inside a 25° C. incubator, where the humidity condition was controlled at 94% RH using a saturated potassium nitrate solution. The solid sample was stored for 4 days to give the titled crystal (Approximately 10 mg). The titled crystal was identified as a hydrate.

Example 4

Preparation of Crystal (Form 4) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To a solution of Compound (I) (217.22 mg) in 2 mol/L ammonia in methanol (2.152 mL) was added ethanol (0.869 mL), and the solution was concentrated down to about 1.1 g under reduced pressure at 50° C. The residue was stirred at room temperature for 0.8 hours and the precipitates fell out of the solution. To the slurry was added ethanol (0.434 mL), and the mixture was concentrated down to about 0.8 g under reduced pressure at 50° C. To the residue was added ethanol (0.434 mL), and the mixture was concentrated down to about 1.2 g under reduced pressure at 50° C. To the resulting slurry was added water (40 L), and the mixture was stirred at room temperature for 1 hour and with ice-cooling for 1.8 hours. The precipitates were cropped by filtration, rinsed successively with ethanol (0.2 mL) and ethyl acetate (0.2 mL), and the solid obtained was dried under reduced pressure at room temperature for 1 hour to give the titled crystal (21.22 mg).

Example 5

Preparation of Crystal (Form 5) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To a suspension of Compound (I) (201.62 mg) in 2-propanol (5 mL) was added 28% ammonia aqueous solution (36 L), and the resulting solution was stirred at 60° C. To the solution was added 28% ammonia aqueous solution (108 L) and the precipitates fell out of the solution. After the temperature was spontaneously decreased to room temperature, the precipitates were cropped by filtration to give the titled crystal (160 mg).

Example 6

Preparation of Crystal (Form 6) of (1R,3R,15E, 28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$,39$\lambda^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt To Compound (I) di-ammonium salt obtained in Example 5 (85.24 mg) was added ethanol (4 mL), and the resulting slurry was stirred at room temperature overnight. Then, the precipitates were cropped by filtration to give the titled crystal (40.93 mg).

Example 7

Preparation of crystal of sodium salt of (1R,3R, 15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34$\lambda^5$, 39$\lambda^5$-diphosphaoctacyclo[28.6.4.1$^{3,36}$.1$^{28,31}$.0$^{4,8}$. 0$^{7,12}$.0$^{19,24}$.0$^{23,27}$]dotetraconta-5,7,9,11,15,19,21,23, 25-nonaene-34,39-dione To Compound (I) (201.58 mg) was added methanol (5 mL), and the resulting slurry was stirred at room temperature. To the slurry was added 1 mol/L aqueous sodium hydroxide solution (0.54 mL), and the resulting solution was stirred at 60° C. for around an hour. After the temperature was spontaneously decreased to room temperature, the solution was concentrated down under nitrogen gas flow with stirring. Crystallization was initiated as the solvent was gradually removed. The solid obtained was dried under reduced pressure at room temperature to give the titled crystal (227 mg).

Example 8

Preparation of Crystal of (1R,3R,15E,28R,29R,30R, 31R,34R,36R,39S,41R)-29,41-Difluoro-34,39-bis (sulfanyl)-2,33,35,38,40,42-hexaoxa-4,6,9,11,13,18, 20,22,25,27-decaaza-34$\lambda^5$,39$\lambda^5$-diphosphaoctacyclo [28.6.4.1$^{3,36}$.1$^{28,31}$.0$^{4,8}$.0$^{7,12}$.0$^{19,24}$.0$^{23,27}$] dotetraconta-5,7,9,11,15,19,21,23,25-nonaene-34,39-dione To a solution of Compound (I) (500 mg) in a mixture of ethanol (2.5 mL), 2 mol/L ammonia in ethanol (2.5 mL) and water (2.5 mL) was added acetic acid (0.572 mL) dropwise, and the solution was stirred at room temperature. To the solution was added a seed crystal of compound (I) obtained in a similar way to the following Example 8-2. Then the mixture was stirred at room temperature for 10 minutes and the precipitates fell out of the solution. To the slurry was gradually added acetic acid (1.144 mL) dropwise for 45 minutes, and the resulting slurry was stirred at room temperature overnight. The precipitates were cropped by filtration, and rinsed successively with cold 67% aqueous ethanol (3.0 mL) and tert-butyl methyl ether (2.0 mL). The solid obtained was dried under reduced pressure at room temperature for 5 hours to give the titled crystal (417 mg) in 83.4% yield.

Example 8-2

Preparation of Crystal of (1R,3R,15E,28R,29R,30R, 31R,34R,36R,39S,41R)-29,41-Difluoro-34,39-bis (sulfanyl)-2,33,35,38,40,42-hexaoxa-4,6,9,11,13,18, 20,22,25,27-decaaza-34$\lambda^5$,39$\lambda^5$-diphosphaoctacyclo [28.6.4.1$^{3,36}$.1$^{28,31}$.0$^{4,8}$.0$^{7,12}$.0$^{19,24}$.0$^{23,27}$] dotetraconta-5,7,9,11,15,19,21,23,25-nonaene-34,39-dione To Compound (I) (497.5 mg) were added ethanol (1.0 mL) and 2 mol/L ammonia in ethanol (2.0 mL), and the mixture was stirred at room temperature and dissolved. The resulting solution was filtered through a cotton pad and the pad was rinsed with 2 mol/L ammonia in ethanol (0.5 mL) and ethanol (1.5 mL), and the solution was added water (2.5 mL). To the resulting solution was gradually added acetic acid (0.57 mL) dropwise at room temperature for 30 minutes and the precipitates fell out of the solution, and the slurry was stirred at room temperature for 37 minutes. To the slurry was gradually added acetic acid (0.85 mL) dropwise for 32 minutes, and the resulting slurry was stirred at room temperature overnight. The precipitates were cropped by filtration, and rinsed successively with cold 67% aqueous ethanol (4.0 mL) and water (4.0 mL). The solid obtained was dried under reduced pressure at room temperature overnight and at 30° C. for 3 hours to give the titled crystal (432.4 mg) in 86.9% yield.

Example 9

Thermogravimetry and Differential Thermal Analysis (TG-DTA) for the Crystal (Form 1)

Approximately 5 mg of the crystal (Form 1) sample was accurately weighed into an aluminum pan and then the analysis was performed under the following conditions. In the TG thermogram, weight loss due to dehydration was observed in the range from room temperature to 130° C.
Measurement Conditions
Atmosphere: nitrogen gas flow of 100 mL/minute
Reference pan: empty aluminum pan
Heating rate: 10° C./minute
Sampling interval: 1 second
Temperature range: room temperature to 300° C.

Example 10

Powder X-Ray Diffraction at Various Temperatures

The crystal (Form 1) sample was placed on the sample stage of a powder X-ray diffractometer and the analysis was performed at room temperature and above 60° C., where significant weight loss due to dehydration was observed in the TG-DTA thermogram of the crystal (Form 1). The measurement conditions are as follows.
Reflection Method Conditions
Equipment: RINT TTR-III (Rigaku)
X-ray source: CuKα (50 kV, 300 mA)
Detector: scintillation counter
Mode: Reflection
Slit: 0.5 mm (divergent slit), open (scattering slit), open (light-receiving slit)
Scan rate: 10°/minute
Sampling interval: 0.02
Scan range: 5° to 350
Sample holder: aluminum holder In the TG-DTA thermogram of the crystal (Form 1) (FIG. 21), significant weight loss due to dehydration was observed in the temperature range up to 130° C., accompanied with endothermic peaks. When the crystal (Form 1) is heated, a significant change was found in the powder X-ray diffraction (PXRD) pattern above 60° C. (FIG. 22). As shown in FIG. 23, the changed PXRD pattern was comparable to that of the crystal (Form 2). Then, the PXRD pattern of the crystal (Form 2) was further changed to another pattern at or above 125° C. (FIG. 24). These findings indicated that the crystal (Form 1) and the crystal (Form 2) would be hydrates.

Example 11

In hygroscopicity measurement of the crystal (Form 1) in the RH range from 30% to 95% at 25° C., a hysteresis loop between adsorption and desorption processes was observed as shown in FIG. 25. In the adsorption process, the weight change level was gradually increased to 1.7% up to 80% RH, and then finally reached approximately 19% at 95% RH. No change was observed in the PXRD patterns before and after the hygroscopicity measurement. In contrast, the PXRD pattern of the crystal (Form 1) sample stored at 25° C. and 94% RH for 4 days was different from the initial pattern as described in FIG. 26. The crystal form of the changed PXRD pattern was defined as Form 3. These findings prove that the crystal (Form 3) is a hydrate.

PHARMACOLOGICAL TEST EXAMPLES

The following test examples were carried out to examine the pharmacological effects of the Compound (1a).

Pharmacological Test Example 1: HAQ STING Agonist Activity Reporter Assay

THP1-Dual™ Cells (InvivoGen, Cat #thpd-nfis) were applied for $EC_{50}$ (determination. THP1 Dual™ Cells have been characterized to carry the HAQ STING genotype by the vendor Invivogen (Insight 201402-1). Cells were grown and maintained under conditions as recommended by manufacturer. The interferon regulatory factor (IRF) pathway induction described in manufacturer's manual was followed for $EC_{50}$ (determination. In brief, cells were seeded and treated with different concentrations of compound for 20 hrs while incubated at 37° C., 5% $CO_2$. Cells were resuspended and QUANTI-Luc™ solution (Cat. #: rep-qlc1) was added. Resulting light emission was measured by luminometer (Envision, Perkin Elmer). Obtained signals were plotted and $EC_{50}$ was calculated with GraphPad Prism7 software. $EC_{50}$ value is reported in Table 1 below.

TABLE 4

| Table 1 | |
| --- | --- |
| Compound No. | Human STING HAQ EC50 (µM) |
| 1a | 4.1 |

Human STING EC50 (µM) of Compound (1a) was measured in Table 1.

Pharmacological Test Example 2: STING Variant Specific Reporter Assay

Human STING has 4 major variants, including WT, HAQ, REF, and AQ variants. REF-STING, also referred to as R232H, for example, occurs in about 14% of the human population. Compared to the wild-type allele, R232H has decreased response to bacterial and metazoan cyclic dinucleotides. Details of these 4 major variants as well as other rare variants are reported by Yi G, et al., "Single nucleotide polymorphisms of human STING can affect innate immune response to cyclic dinucleotides" PLoS One 2013; 8:e77846. STING variant specific reporter cell lines were established by using THP1-Dual™ KO-STING cells (InvivoGen, Cat #thpd-kostg) and three STING variant protein expression vectors. The expression vector map for WT STING is shown in FIG. 16. For the other two expression vectors, different STING variant sequences were used in that vector, with the WT STING replaced by the appropriate nucleotide sequence.

STING variant-expressing vectors for WT-STING, REF-STING, and AQ-STING were prepared and stably transfected into THP1-Dual™ KO-STING cells to prepare STING variant-specific reporter assays for WT-STING, REF-STING and AQ-STING, respectively. $EC_{50}$ values were determined as described above in Pharmacological Test Example 1 for the HAQ STING agonist activity reporter assay. Results are shown below in Table 2. The DNA sequences used for these STING variants are shown in SEQ ID NO: 1 (Nucleotide Sequence of WT Human STING), SEQ ID NO: 2 (Nucleotide Sequence of REF Human STING), and SEQ ID NO: 3 (Nucleotide Sequence of AQ Human Sting).

WT Human STING:
(SEQ ID NO: 1)
atgccccactccagcctgcatccatccatcccgtgtcccaggggtcacggggcccagaaggcagccttggttctgctgag tgcctgctggtgacccttgggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca agggcctggccccagctgagatctctgcagtgtgtgaaaaagggaatttcaacgtggcccatgggctggcatggtcatatta catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccggtgaccgggctggcatcaaggatcgggtttacagcaacagcatctatgag cttctggagaacgggcagcgggcgggcacctgtgtcctggagtacgccaccccttgcagactttgtttgccatgtcacaat acagtcaagctggcttagccggaggataggcttgagcaggccaaactcttctgccggacacttgaggacatcctggcag atgcccctgagtctcagaacaactgccgcctcattgcctaccaggaacctgcagatgacagcagcttctcgctgtcccagga ggttctccggcacctgcggcaggaggaaaaggaagaggttactgtgggcagcttgaagacctcagcggtgcccagtacct ccacgatgtcccaagagcctgagctcctcatcagtggaatggaaaagcccctccctctccgcacggatttctcttga.

REF Human STING:
(SEQ ID NO: 2)
atgccccactccagcctgcatccatccatcccgtgtcccaggggtcacggggcccagaaggcagccttggttctgctgag tgcctgctggtgacccttgggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca agggcctggccccagctgagatctctgcagtgtgtgaaaaagggaatttcaacgtggcccatgggctggcatggtcatatta catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccggtgaccatgctggcatcaaggatcgggtttacagcaacagcatctatgagc ttctggagaacgggcagcgggcgggcacctgtgtcctggagtacgccaccccttgcagactttgtttgccatgtcacaata cagtcaagctggcttagccggaggataggcttgagcaggccaaactcttctgccggacacttgaggacatcctggcagat gcccctgagtctcagaacaactgccgcctcattgcctaccaggaacctgcagatgacagcagcttctcgctgtcccaggag gttctccggcacctgcggcaggaggaaaaggaagaggttactgtgggcagcttgaagacctcagcggtgcccagtacctc cacgatgtcccaagagcctgagctcctcatcagtggaatggaaaagcccctccctctccgcacggatttctcttga AQ Human STING:
(SEQ ID NO: 3)
atgccccactccagcctgcatccatccatcccgtgtcccaggggtcacggggcccagaaggcagccttggttctgctgag tgcctgctggtgacccttgggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca -continued

```
agggcctggcccagctgagatctctgcagtgtgtgaaaaagggaatttcaacgtggcccatgggctggcatggtcatatta catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccgctgaccgagctggcatcaaggatcgggtttacagcaacagcatctatgag cttctggagaacgggcagcgggcgggcacctgtgtcctggagtacgccacccccttgcagactttgtttgccatgtcacaat acagtcaagctggctttagccgggaggataggcttgagcaggccaaactcttctgccagacacttgaggacatcctggcag atgccctgagtctcagaacaactgccgcctcattgcctaccaggaacctgcagatgacagcagcttctcgctgtcccagga ggttctccggcacctgcggcaggaggaaaaggaagaggttactgtgggcagcttgaagacctcagcggtgcccagtacct ccacgatgtcccaagagcctgagctcctcatcagtggaatggaaaagcccctccctctccgcacggatttctcttga
```

Pharmacological Test Example 3: Mouse STING Agonist Activity Reporter Assay

RAW-Lucia™ ISG Cells (InvivoGen, Cat #rawl-isg) were used for a mouse STING agonist reporter assay. $EC_{50}$ values were determined as described above in Pharmacological Test Example 1 in the HAQ STING agonist activity reporter assay. Results are shown below in Table 2.

TABLE 5

Table 2 Compound (1a) in vitro characterization

| Compound | Human STING EC50(µM) | | | Mouse STING AQ EC50 (µM) | DSF WT STING ΔTm (° C.) |
|---|---|---|---|---|---|
| | WT | HAQ | REF | | |
| 1a | 0.9 | 4.1 | 4.8 | 1.2 | 3.4 | 17.6 |

Pharmacological Test Example 4: Differential Scanning Fluorimetry (DSF) Assay A DSF assay was employed to measure the physical interaction between compound and recombinant STING protein. Truncated recombinant STING protein (a.a.155-341) (SEQ ID NO: 4) was expressed in E. coli and isolated for the assay, as described below. Assay matrix was prepared in 384-well plates to a final volume of 10 µL per well consisting of 1 µM recombinant STING protein (a.a. 155-341) (SEQ ID NO: 4), 100 mM PBS pH 7.4, supplemented with 100 mM KCl, 5×SYPRO orange dye and 50 µM compound (final DMSO conc. 0-1%). Assays were performed on a QuantStudio 12K Flex Real-Time PCR System using a temperature gradient from 25° C. to 95° C. at a rate of 0.05° C./min, and excitation and emission filters at 470 and 586 nm, respectively. According to the fluorescence derivative curves assigned by the Applied Biosystems (registered trademark) Protein Thermal Shift software (algorithm version 1.3.), the thermal melt (Tm) of the unbound and ligand bound recombinant STING protein and the difference in thermal melt (dTm D) was calculated.

In general, compounds with ΔTm values larger than 0 are considered to have a physical interaction with the tested protein, and the value of ΔTm is positively associated with compound binding affinity. Here, Compound (1a) showed the ΔTm of 17.6 (Table 2 shown above), indicating physical interaction with STING protein.

Pharmacological Test Example 5: Ex Vivo Human PBMC Stimulation Assay

Human blood from 5 healthy donors was collected using 10.0 mL BD Vacutainer Sodium heparin tubes (cat #367874). Peripheral blood mononuclear cell (PBMC) isolation was done using SIGMA ACCUSPIN 50 ml Tubes (cat #A2055) and sigma ACCUSPIN System-HISTOPAQUE-1077 (cat #A7054) using protocol provided by manufacturer. PBMC layer was harvested and washed with 1× Phosphate Buffered Saline (PBS) as suggested by Sigma. PBMC were counted and finally suspended at 1×10e6/ml in RPMI (corning cat #10-041-CV) supplemented with 10% fetal bovine serum (FBS) (Gibco cat #20140.79). 1 ml of cell (1×10e6) were transferred into Falcon 5 mL Round Bottom Polypropylene Test Tube (cat #352063) and stimulated with different concentrations (0, 0.1, 1, 10 M) for 24 hours in 5% $CO_2$ incubator at 37° C. After 24 hours of incubation the tubes were centrifuged at 1400 rpm for 5 minutes and supernatants were harvested. Supernatant were stored in −80° C. for subsequent IFN measurement. IFNβ measurement was done using Human IFN-β Base Kit (Meso Scale Diagnostics cat #K151ADA) and protocol provided by manufacturer was used. IFN-beta estimation was done by reading assay plate at MESO SECTOR Imager 2400 and using MSD Discovery Workbench 4.0 program. After 24 hours IFNβ protein was analyzed. The results showed that Compound (1a) can induce primary human PBMC IFNβ protein production in a dose-dependent manner. Results shown in Table 3 reflect an average of measurements conducted using five different donors.

TABLE 6

Table 3 Ex vivo human PBMC stimulation assay

| | PBS (Control) | Compound (1a) | | |
|---|---|---|---|---|
| | | 0.1 µM | 1 µM | 10 µM |
| IFNβ (pg/mL) | 0 | 21.3 ± 17.8 | 227.5 ± 62.4 | 540.2 ± 215.0 |

For IFNβ mRNA quantification, total RNA was isolated using the RNeasy Mini Kit (Qiagen, Germany) according to the manufacturer's protocol. IFNβ mRNA was quantified by qPCR assay. In brief, total RNA (400 ng to 1000 ng) was converted to cDNA in a 60 µl reaction volume using SuperScript VILO MasterMix (Life Technologies, USA). Obtained cDNAs (10 ng) were subsequently amplified using Applied Biosystems TaqMan expression assays using RNA-specific primers for IFNB1 (Hs01077958_s1), and GAPDH (Hs99999905_m1). A qPCR analysis was performed with TaqMan Fast Advanced Master Mix (Life Technologies, USA) on the Applied Biosystems Quantstudio 12K Flex Real-Time PCR System, with an initial 2-min step at 50° C. followed by 95° C. for 2 s and 40 cycles of 95° C. for is and 60° C. for 20 s. Relative gene expression was calculated after normalization against the reference gene GAPDH using the 2-ΔΔCT method. Calculations were done using the Applied Biosystems Quantstudio 12K Flex software v1.2.2. IFNβ mRNA fold changes vs. vehicle treated samples are summarized in Table 4. The results showed that Compound (1a) can induce IFNβ mRNA in primary PBMC in a dose- and time-dependent manner. Table 4 shows an average calculated from five different donors.

TABLE 7

Table 4 Ex vivo human PBMC 3-hr & 24-hr stimulation assay (mRNA)

| IFNβ mRNA (fold changes vs. vehicle treated samples) | Compound (1a) | | |
|---|---|---|---|
| | 0.1 μM | 1 μM | 10 μM |
| 3-hr treatment | 51.0 ± 21.7 | 219.8 ± 69.8 | 1973.3 ± 1023.0 |
| 24-hr treatment | 28.1 ± 28.9 | 10652.3 ± 4992.4 | 24157.3 ± 9224.2 |

Pharmacological Test Example 6: Anti-Cancer Effect of Compound (1a) on the CT26 Dual Tumor Model Compound (1a) was tested for its anti-cancer activity in CT26 dual tumor model, which is a mouse colon cancer model. Female of 5-6 week old Balb/cJ mice (Jackson Labs, Bar Harbor, Me.) were implanted subcutaneously with CT26 tumor cells on both sides of each animal, $10^5$ cells for each side. For study A, treatment was started 5 days (1.25 mg/kg, 2.5 mg/kg and 5 mg/kg) after the tumor implantation, when the average tumors reached approximately 100 mm$^3$. For study B, treatment was started 8 days (0.6 mg/kg, and 10 mg/kg) after the tumor implantation, when the average tumors reached approximately 120 mm$^3$. The treatment scheme is described in Table 5 and Table 6.

TABLE 8

Table 5 Dosing scheme for study A

| Group | No. of Animals | Treatment | Route and Schedule |
|---|---|---|---|
| A | 6 | Vehicle (1 × PBS) | I.T.*; single dose |
| B | 6 | 5 mg/kg Compound (1a) | I.T.; single dose |
| C | 6 | 2.5 mg/kg Compound (1a) | I.T.; single dose |
| D | 6 | 1.25 mg/kg Compound (1a) | I.T.; single dose |

*I.T. is intratumoral.

TABLE 9

Table 6 Dosing scheme for study B

| Group | No. of Animals | Treatment | Route and Schedule |
|---|---|---|---|
| A | 5 | Vehicle (1 × PBS) | I.T*; single dose |
| B | 5 | 10 mg/kg Compound (1a) | I.T.; single dose |
| C | 5 | 0.6 mg/kg Compound (1a) | I.T.; single dose |

*I.T. is intratumoral.

All the mice in the study have two subcutaneous CT26 tumors. The "treated tumor" indicates the tumor with compound direct administration, while "untreated tumor" indicates the tumor without direct compound administration. Tumor volume was followed throughout the experiment. Tumor volume is measured two times weekly after the start of treatment. Tumor burden is calculated from caliper measurements by the formula for the volume of a prolate ellipsoid $(L \times W^2)/2$ where L and W are the respective orthogonal length and width measurements (mm).

Compound (1a) showed potent and curative activity in CT26 dual tumor model (FIG. 17 and FIG. 18). For treated tumors, a cure rate of 20% was detected even at the lowest dose tested in the study (FIG. 18, 0.6 mg/kg dose). At the same time, the highest dose (10 mg/kg) cured 100% of animals of that tumor at the end of study. For the untreated tumors, a dose-dependent anti-tumor effect was also evident. The top dose group (10 mg/kg) showed 80% curative effects; all the lower doses also showed tumor growth inhibition activity. Hence, a therapeutic window of 0.6 mg/kg to 10 mg/kg for Compound (1a) was observed, with anti-tumor activity seen not only locally but also systemically, based on effects at the non-injected distal tumor site. In conclusion, these results indicate that local administration of Compound (1a) can induce both local and systemic (abscopal) anti-cancer activity.

Pharmacological Test Example 7: Anti-Cancer Effect of Compound (1a) on the CT26 Liver Metastatic Model Compound (1a) was tested for its anti-cancer activity in a CT26 liver metastatic model. Anesthetized female 5-6 week-old BALB/cJ mice (Jackson Labs, Bar Harbor, Me.) were implanted intra-splenically with luciferase-expressing CT26 tumor cells ($5 \times 10^1$ cells per mouse). A subsequent ten minutes waiting period allowed tumor cells to circulate into the animals' livers. Spleens were then removed and animals were sutured and allowed to recover. Three days later, CT26 tumor cells ($10^1$ cells per mouse) were again implanted, this time subcutaneously (sc) under the right forelimb area, to enable development of a tumor mass for compound administration. Nine days after intra-splenic injection, compound (10 mg/kg) was administered intratumorally, a single time, into the sc tumor.

The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse liver. Compound (1a) showed both potent activity towards the local sc tumors and also curative systemic activity in 9 of 10 treated animals (FIG. 19). These results indicate that local administration of Compound (1a) can induce both local and systemic (abscopal) anti-cancer activity including deep lesion such as in the liver.

Pharmacological Test Example 8: Anti-Cancer Effect of Compound (1a) on the GL261 Brain Orthotopic Model Compound (1a) was tested for its anti-cancer activity in a GL261 brain orthotopic model. GL261 is a murine glioma cell line. Luciferase expressing GL261 mouse glioma cells ($2 \times 10^4$ cells/mouse) were intra-cranially implanted into female 5-6 week-old B6 albino mice (Jackson Labs, Bar Harbor, Me.). Three to 4 days later, GL261 cells were implanted subcutaneously ($10^6$ cells/mouse) under the right forelimb area to allow development of a tumor mass for compound administration. Ten days after intracranial tumor cell implantation, compound (10 mg/kg) was administered intratumorally, a single time, into the sc tumor.

The local anti-cancer effect of compound was measured through its effect on the sc tumor, while the compound's abscopal effect was assessed by the overall survival of treated mice compared with vehicle-treated control mice, based on the detrimental effect of the growing tumor mass in each mouse brain. Compound (1a) showed both potent activity at local sc tumors and showed curative systemic activity in 5 of 8 treated animals (FIG. 20). These results indicate that local administration of Compound (1a) can induce both local and systemic (abscopal) anti-cancer activity including deep lesion such as in the brain.

```
SEQUENCE LISTINGS
SEQ ID NO: 1 (WT Human STING):
    atgccccactccagcctgcatccatccatcccgtgtcccaggggtcacggggcccagaaggcagccttggttctgctgag tgcctgctggtgacccttTggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca agggcctggccccagctgagatctctgcagtgtgtgaaaaagggaatttcaacgtggcccatgggctggcatggtcatatta catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccggtgaccgggctggcatcaaggatcgggtttacagcaacagcatctatgag cttctggagaacgggcagcgggcgggcacctgtgtcctggagtacgccaccccttgcagactttgtttgccatgtcacaat acagtcaagctggctttagccgggaggataggcttgagcaggccaaactcttctgccggacacttgaggacatcctggcag atgcccctgagtctcagaacaactgccgcctcattgcctaccaggaacctgcagatgacagcagcttctcgctgtcccagga ggttctccggcacctgcggcaggaggaaaaggaagaggttactgtgggcagcttgaagacctcagcggtgcccagtacct ccacgatgtcccaagagcctgagctcctcatcagtggaatggaaaagcccctccctctccgcacggatttctcttga SEQ ID NO: 2 (REF Human STING):
    atgccccactccagcctgcatccatccatcccgtgtcccaggggtcacggggcccagaaggcagccttggttctgctgag tgcctgctggtgacccttTggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca agggcctggccccagctgagatctctgcagtgtgtgaaaaagggaatttcaacgtggcccatgggctggcatggtcatatta catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccggtgaccatgctggcatcaaggatcgggtttacagcaacagcatctatgagc ttctggagaacgggcagcgggcgggcacctgtgtcctggagtacgccaccccttgcagactttgtttgccatgtcacaata cagtcaagctggctttagccgggaggataggcttgagcaggccaaactcttctgccggacacttgaggacatcctggcagat gcccctgagtctcagaacaactgccgcctcattgcctaccaggaacctgcagatgacagcagcttctcgctgtcccaggag gttctccggcacctgcggcaggaggaaaaggaagaggttactgtgggcagcttgaagacctcagcggtgcccagtacctc cacgatgtcccaagagcctgagctcctcatcagtggaatggaaaagcccctccctctccgcacggatttctcttga SEQ ID NO: 3 (AQ Human STING):
    Atgccccactccagcctgcatccatccatcccgtgtcccaggggtcacggggcccagaaggcagccttggttctgctgagt gcctgctggtgacccttTggggctaggagagccaccagagcacactctccggtacctggtgctccacctagcctccctg cagctgggactgctgttaaacggggtctgcagcctggctgaggagctgcgccacatccactccaggtaccggggcagcta ctggaggactgtgcgggcctgcctgggctgcccccctccgccgtggggccctgttgctgctgtccatctatttctactactccct cccaaatgcggtcggcccgcccttcacttggatgcttgccctcctgggcctctcgcaggcactgaacatcctcctgggcctca agggcctggccccagctgagatctctgcagtgtgtgaaaaagggaatttcaacgtggcccatgggctggcatggtcatatta
```

-continued catcggatatctgcggctgatcctgccagagctccaggcccggattcgaacttacaatcagcattacaacaacctgctacgg ggtgcagtgagccagcggctgtatattctcctcccattggactgtggggtgcctgataacctgagtatggctgaccccaacatt cgcttcctggataaactgccccagcagaccgctgaccgagctggcatcaaggatcgggtttacagcaacagcatctatgag cttctggagaacgggcagcgggcgggcacctgtgtcctggagtacgccacccccttgcagactttgtttgccatgtcacaat acagtcaagctggctttagccggggaggataggcttgagcaggccaaactcttctgccagacacttgaggacatcctggcag atgcccctgagtctcagaacaactgccgcctcattgcctaccaggaacctgcagatgacagcagcttctcgctgtcccagga ggttctccggcacctgcggcaggaggaaaaggaagaggttactgtgggcagcttgaagacctcagcggtgcccagtacct ccacgatgtcccaagagcctgagctcctcatcagtggaatggaaaagcccctccctctccgcacggatttctcttga SEQ ID NO: 4 (WT STING residues 155-341):
VAHGLAWSYYIGYLRLILPELQARIRTYNQHYNNLLRGAVSQRLYILLPLDCG

VPDNLSMADPNIRFLDKLPQQTGDRAGIKDRVYSNSIYELLENGQRAGTCVLE

YATPLQTLFAMSQYSQAGFSREDRLEQAKLFCRTLEDILADAPESQNNCRLIAY

QEPADDSSFSLSQEVLRHLRQEEKEEV

---

The invention claimed is:

1. A crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) di-ammonium salt (Form 1), Compound (I)

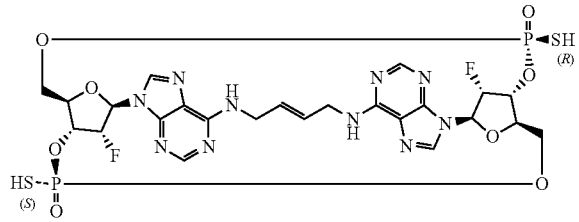

having powder X-ray diffraction peaks at diffraction angles (2θ±0.2°) of 6.4°, 8.3°, 12.7°, 16.6° and 25.4° in a powder X-ray diffraction.

2. The crystal (Form 1) according to claim 1, which is a hydrate.

3. A crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) di-ammonium salt (Form 2), Compound (I)

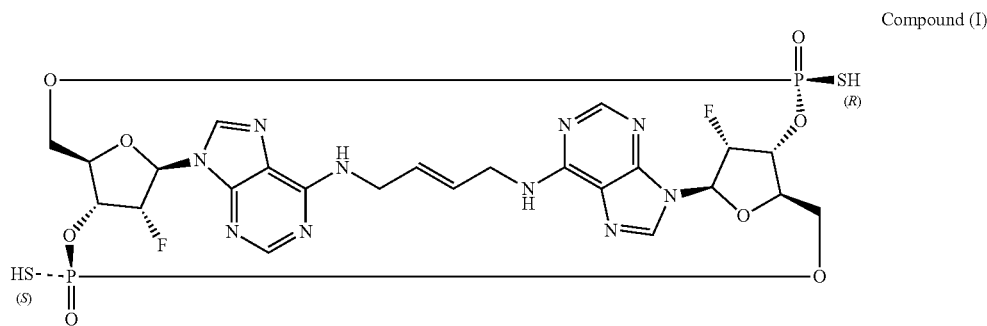

having powder X-ray diffraction peaks at diffraction angles (2θ±0.2°) of 9.0°, 15.4°, 20.8°, 24.0° and 30.0° in a powder X-ray diffraction.

4. The crystal (Form 2) according to claim 3, which is a hydrate.

5. A crystal of (1R,3R,15E,28R,29R,30R,31R,34R,36R,39S,41R)-29,41-Difluoro-34,39-bis(sulfanyl)-2,33,35,38,40,42-hexaoxa-4,6,9,11,13,18,20,22,25,27-decaaza-34λ$^5$,39λ$^5$-diphosphaoctacyclo[28.6.4.1$^{3,36}$.1$^{28,31}$.0$^{4,8}$.0$^{7,12}$.0$^{19,24}$.0$^{23,27}$]dotetraconta-5,7,9,11,15,19,21,23,25-nonaene-34,39-dione (Compound (I)) di-ammonium salt (Form 3), Compound (I)

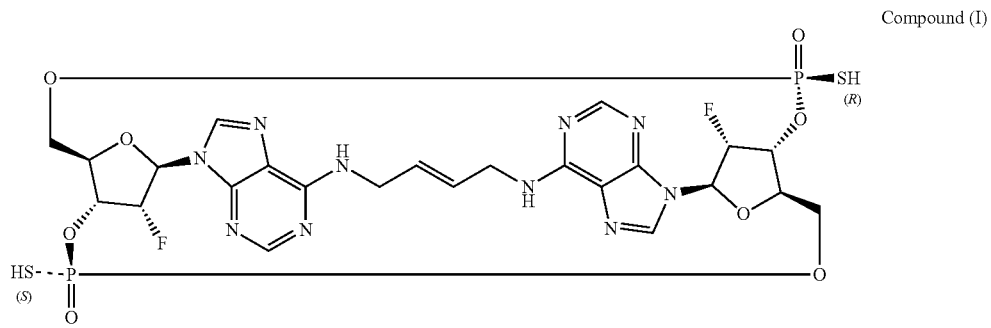

having powder X-ray diffraction peaks at diffraction angles (2θ±0.2°) of 6.0°, 7.4°, 9.3°, 16.0° and 21.4° in a powder X-ray diffraction.

6. The crystal (Form 3) according to claim 5, which is a hydrate.

7. A crystal of (1R,3R,15E,28R,29R,30R,31R,34R,36R, 39S,41R)-29,41-Difluoro-34,39-bis(sulfanyl)-2,33,35,38, 40,42-hexaoxa-4,6,9,11,13,18,20,22,25,27-decaaza-34λ$^5$, 39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt (Form 4),

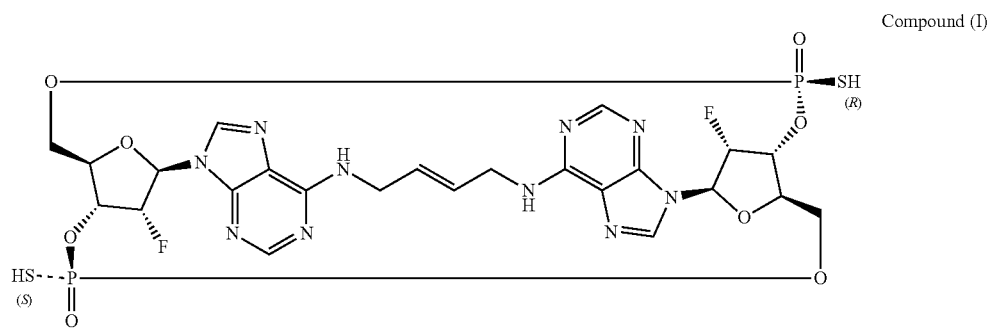

Compound (I)

having powder X-ray diffraction peaks at diffraction angles (2θ±0.2°) of 9.7°, 14.0°, 17.4°, 22.3° and 26.9° in a powder X-ray diffraction.

8. A crystal of (1R,3R,15E,28R,29R,30R,31R,34R,36R, 39S,41R)-29,41-Difluoro-34,39-bis(sulfanyl)-2,33,35,38, 40,42-hexaoxa-4,6,9,11,13,18,20,22,25,27-decaaza-34λ$^5$, 39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) di-ammonium salt (Form 5),

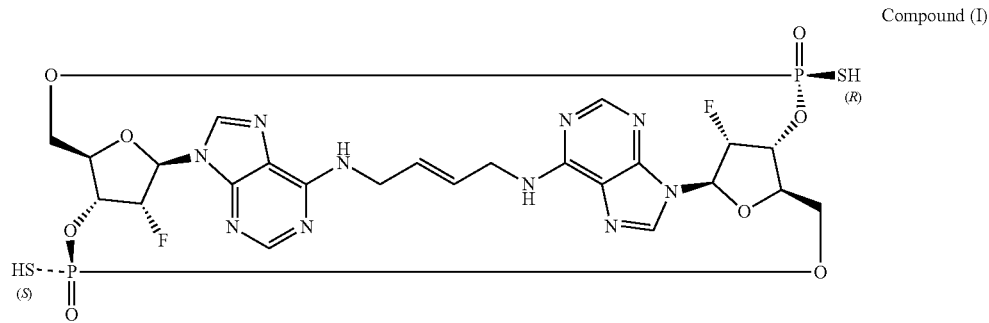

Compound (I)

having powder X-ray diffraction peaks at diffraction angles (2θ±0.2°) of 10.9°, 17.7°, 18.9°, 20.0° and 23.6° in a powder X-ray diffraction.

9. A crystal of (1R,3R,15E,28R,29R,30R,31R,34R,36R, 39S,41R)-29,41-Difluoro-34,39-bis(sulfanyl)-2,33,35,38, 40,42-hexaoxa-4,6,9,11,13,18,20,22,25,27-decaaza-34λ$^5$, 39λ$^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) mono-ammonium salt (Form 6),

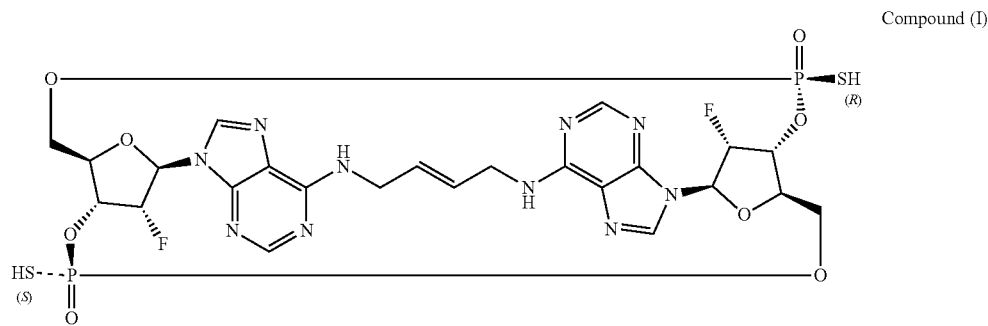

Compound (I)

having powder X-ray diffraction peaks at diffraction angles (2θ±0.2°) of 15.1°, 16.4°, 17.0°, 21.6° and 25.9° in a powder X-ray diffraction.

10. A crystal of (1R,3R,15E,28R,29R,30R,31R,34R,36R, 39S,41R)-29,41-Difluoro-34,39-bis(sulfanyl)-2,33,35,38, 40,42-hexaoxa-4,6,9,11,13,18,20,22,25,27-decaaza-34$\lambda^5$, 39$\lambda^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)) sodium salt,

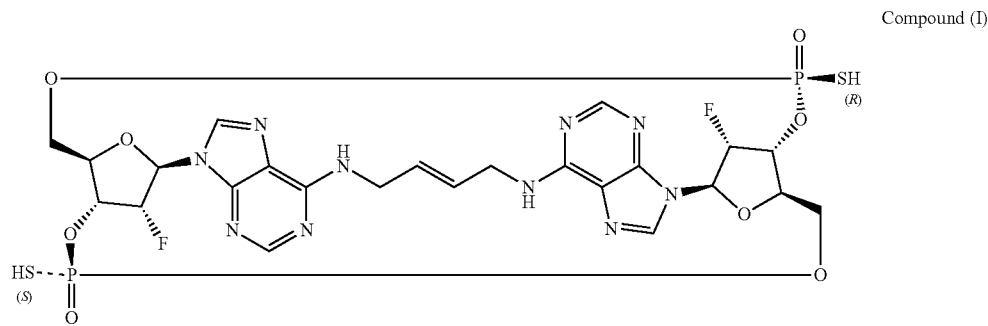

Compound (I)

having powder X-ray diffraction peaks at diffraction angles (2θ±0.2°) of 6.1°, 9.3°, 15.9°, 16.6° and 22.3° in a powder X-ray diffraction.

11. A crystal of (1R,3R,15E,28R,29R,30R,31R,34R,36R, 39S,41R)-29,41-Difluoro-34,39-bis(sulfanyl)-2,33,35,38, 40,42-hexaoxa-4,6,9,11,13,18,20,22,25,27-decaaza-34$\lambda^5$, 39$\lambda^5$-diphosphaoctacyclo[28.6.4.1$^{3,36}$.1$^{28,31}$.0$^{4,8}$.0$^{7,12}$. 0$^{19,24}$.0$^{23,27}$]dotetraconta-5,7,9,11,15,19,21,23,25-nonaene-34,39-dione (Compound (I)),

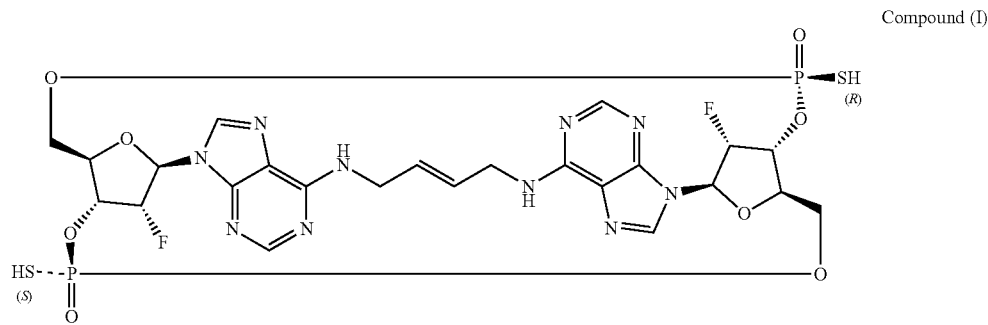

Compound (I)

having powder X-ray diffraction peaks at diffraction angles (2θ±0.2°) of 5.6°, 8.9°, 11.4°, 13.9° and 16.8° in a powder X-ray diffraction.

12. A pharmaceutical composition comprising the crystal according to any one of claims 1, 2, 3, 4, 5, 6, 7, 8, 9, 10 and 11.

* * * * *